US012650432B2

(12) United States Patent
Brosens

(10) Patent No.: US 12,650,432 B2
(45) Date of Patent: Jun. 9, 2026

(54) SCARA5 AND DIO2 AS BIOMARKERS FOR MISCARRIAGE AND IMPLANTATION FAILURE

(71) Applicant: The University of Warwick, Coventry (GB)

(72) Inventor: Jan Brosens, Coventry (GB)

(73) Assignee: The University of Warwick, Coventry (GB)

( * ) Notice: Subject to any disclaimer, the term of this patent is extended or adjusted under 35 U.S.C. 154(b) by 1021 days.

(21) Appl. No.: 17/636,396

(22) PCT Filed: Aug. 19, 2020

(86) PCT No.: PCT/GB2020/051979
§ 371 (c)(1),
(2) Date: Feb. 18, 2022

(87) PCT Pub. No.: WO2021/032973
PCT Pub. Date: Feb. 25, 2021

(65) Prior Publication Data
US 2022/0299520 A1 Sep. 22, 2022

(30) Foreign Application Priority Data
Aug. 20, 2019 (GB) .................................... 1911947

(51) Int. Cl.
*G01N 33/68* (2006.01)
*C12N 15/10* (2006.01)

(52) U.S. Cl.
CPC ....... *G01N 33/689* (2013.01); *C12N 15/1096* (2013.01); *C12N 2320/10* (2013.01); *G01N 2800/368* (2013.01); *G01N 2800/50* (2013.01); *G01N 2800/52* (2013.01)

(58) Field of Classification Search
None
See application file for complete search history.

(56) References Cited

FOREIGN PATENT DOCUMENTS

| EP | 2333107 B1 | | 4/2014 | |
| WO | WO 2014/013079 | * | 1/2014 | ............. G01N 33/68 |
| WO | 2018/096375 A2 | | 5/2018 | |

OTHER PUBLICATIONS

Feng et al., Cancer 2005; 104: 2409-16 (Year: 2005).*
Zeng et al, Journal of Reproductive Immunology 155 (2023) 103776 (Year: 2023).*
Founds et al. (Placenta 30 (2009) 15-24 (Year: 2009).*
Duncan et al. (PLoS ONE 6(8): e23595. doi:10.1371/journal.pone. 0023595 (Year: 2011).*
Rai, R. & Regan, L. Recurrent miscarriage. Lancet 368, 601-611, doi:10.1016/S0140-6736(06)69204-0 (2006).

Hardy, K., Hardy, P. J., Jacobs, P. A., Lewallen, K. & Hassold, T. J. Temporal changes in chromosome abnormalities in human spontaneous abortions: Results of 40 years of analysis. Am J Med Genet A 170, 2671-2680, doi:10.1002/ajmg.a.37795 (2016).
Hassold, T. et al. A cytogenetic study of 1000 spontaneous abortions. Ann Hum Genet 44, 151-178 (1980).
Ogasawara, M., Aoki, K., Okada, S. & Suzumori, K. Embryonic karyotype of abortuses in relation to the number of previous miscarriages. Fertility and sterility 73, 300-304 (2000).
Stephenson, M. D., Awartani, K. A. & Robinson, W. P. Cytogenetic analysis of miscarriages from couples with recurrent miscarriage: a case-control study. Hum Reprod 17, 446-451 (2002).
Sullivan, A. E., Silver, R. M., LaCoursiere, D. Y., Porter, T. F. & Branch, D. W. Recurrent fetal aneuploidy and recurrent miscarriage. Obstet Gynecol 104, 784-788, doi:10.1097/01.AOG.0000137832. 86727.e2 (2004).
Carp, H. et al. Karyotype of the abortus in recurrent miscarriage. Fertil Steril 75, 678-682 (2001).
Robberecht, C. et al. Cytogenetic and morphological analysis of early products of conception following hystero-embryoscopy from couples with recurrent pregnancy loss. Prenat Diagn 32, 933-942, doi:10.1002/pd.3936 (2012).
Eshre. Recurrent Pregnancy Loss: A Guideline of the European Society of Human Reproduction and Embryology. (2017).
Practice Committee of the American Society for Reproductive, M. Evaluation and treatment of recurrent pregnancy loss. Fertility and Sterility 5, 1103-1111 (2012).
Cha, J., Sun, X. & Dey, S. K. Mechanisms of implantation: strategies for successful pregnancy. Nature medicine 18, 1754-1767, doi:10.1038/nm.3012 (2012).
Moraes, J. G. N. et al. Uterine influences on conceptus development in fertility-classified animals. Proc Natl Acad Sci U S A 115, E1749-E1758, doi: 10.1073/pnas.1721191115 (2018).
Salker, M. S. et al. Disordered IL-33/ST2 activation in decidualizing stromal cells prolongs uterine receptivity in women with recurrent pregnancy loss. PLoS One 7, e52252, doi:10.1371/journal.pone. 0052252 (2012).
Gellersen, B. & Brosens, J. J. Cyclic decidualization of the human endometrium in reproductive health and failure. Endocrine reviews 35, 851-905, doi:10.1210/er.2014-1045 (2014).
Brighton, P. J. et al. Clearance of senescent decidual cells by uterine natural killer cells in cycling human endometrium. eLife 6, doi:10. 7554/eLife.31274 (2017).
Nancy, P. et al. Chemokine gene silencing in decidual stromal cells limits T cell access to the maternal-fetal interface. Science 336, 1317-1321, doi:10.1126/science.1220030 (2012).

(Continued)

*Primary Examiner* — Christina M Borgeest
(74) *Attorney, Agent, or Firm* — Dorf Nelson & Zauderer LLP; Scott D. Locke, Esq.

(57) ABSTRACT

The invention relates to methods for assessing the risk of miscarriage or embryo implantation failure, and also for monitoring or evaluating the effect of a treatment to reduce the risk of miscarriage or embryo implantation failure using specific biomarkers. The invention also relates to the use of these biomarkers in methods of diagnosing a reproductive disorder in an individual, and also to methods of treating a reproductive disorder. In addition, the biomarkers can further be used in methods of selecting patients for treatment to reduce risk of embryo implantation failure or miscarriage. The invention also relates to kits for use in any of the methods described herein.

12 Claims, 20 Drawing Sheets

Specification includes a Sequence Listing.

(56)　　　　　References Cited

OTHER PUBLICATIONS

Macosko, E. Z. et al. Highly Parallel Genome-wide Expression Profiling of Individual Cells Using Nanoliter Droplets. Cell 161, 1202-1214, doi:10.1016/j.cell.2015.05.002 (2015).

Al-Sabbagh, M. et al. NADPH oxidase-derived reactive oxygen species mediate decidualization of human endometrial stromal cells in response to cyclic AMP signaling. Endocrinology 152, 730-740, doi:10.1210/en.2010-0899 (2011).

Erkenbrack, E. M. et al. The mammalian decidual cell evolved from a cellular stress response. PLoS Biol 16, e2005594, doi:10.1371/journal.pbio.2005594 (2018).

Kuroda, K. et al. Elevated periimplantation uterine natural killer cell density in human endometrium is associated with impaired corticosteroid signaling in decidualizing stromal cells. The Journal of clinical endocrinology and metabolism 98, 4429-4437, doi:10.1210/jc.2013-1977 (2013).

Song, J. J. et al. Role of glutaredoxin in metabolic oxidative stress. Glutaredoxin as a sensor of oxidative stress mediated by H2O2. J Biol Chem 277, 46566-46575, doi:10.1074/jbc.M206826200 (2002).

Zuo, R. J. et al. Crystallin alphaB acts as a molecular guard in mouse decidualization: regulation and function during early pregnancy. FEBS Lett 588, 2944-2951, doi:10.1016/j.febslet.2014.05.045 (2014).

Latini, F. R. et al. ABI3 ectopic expression reduces in vitro and in vivo cell growth properties while inducing senescence. BMC Cancer 11, 11, doi:10.1186/1471-2407-11-11 (2011).

Michishita, E., Garces, G., Barrett, J. C. & Horikawa, I. Upregulation of the KIAA1199 gene is associated with cellular mortality. Cancer Lett 239, 71-77, doi:10.1016/j.canlet.2005.07.028 (2006).

Petropoulou, C., Trougakos, I. P., Kolettas, E., Toussaint, O. & Gonos, E. S. Clusterin/apolipoprotein J is a novel biomarker of cellular senescence that does not affect the proliferative capacity of human diploid fibroblasts. FEBS Lett 509, 287-297 (2001).

Trougakos, I. P. The molecular chaperone apolipoprotein J/clusterin as a sensor of oxidative stress: implications in therapeutic approaches—a mini-review. Gerontology 59, 514-523, doi:10.1159/000351207 (2013).

Bianco, A. C. & Kim, B. W. Deiodinases: implications of the local control of thyroid hormone action. J Clin Invest 116, 2571-2579, doi:10.1172/JCI29812 (2006).

Altmae, S. et al. Meta-signature of human endometrial receptivity: a meta-analysis and validation study of transcriptomic biomarkers. Sci Rep 7, 10077, doi:10.1038/s41598-017-10098-3 (2017).

Vento-Tormo, R. et al. Single-cell reconstruction of the early maternal-fetal interface in humans. Nature 563, 347-353, doi:10.1038/s41586-018-0698-6 (2018).

Drury, J. A., Tang, A. W., Turner, M. A. & Quenby, S. A rapid, reliable method for uNK cell density estimation. J Reprod Immunol 97, 183-185, doi:10.1016/j.jri.2012.12.002 (2013).

Lucas, E. S. et al. Loss of Endometrial Plasticity in Recurrent Pregnancy Loss. Stem Cells 34, 346-356, doi:10.1002/stem.2222 (2016).

Ramsey, E. M., Houston, M. L. & Harris, J. W. Interactions of the trophoblast and maternal tissues in three closely related primate species. American journal of obstetrics and gynecology 124, 647-652 (1976).

Emera, D., Romero, R. & Wagner, G. The evolution of menstruation: a new model for genetic assimilation: explaining molecular origins of maternal responses to fetal invasiveness. Bioessays 34, 26-35, doi:10.1002/bies.201100099 (2012).

Evans, J. & Salamonsen, L. A. Inflammation, leukocytes and menstruation. Rev Endocr Metab Disord 13, 277-288, doi:10.1007/s11154-012-9223-7 (2012).

Evans, J. & Salamonsen, L. A. Decidualized human endometrial stromal cells are sensors of hormone withdrawal in the menstrual inflammatory cascade. Biol Reprod 90, 14, doi:10.1095/biolreprod.113.108175 (2014).

O'Leary, M. A. et al. The placental mammal ancestor and the post-K-Pg radiation of placentals. Science 339, 662-667, doi:10.1126/science.1229237 (2013).

Marcais, A. et al. The metabolic checkpoint kinase mTOR is essential for IL-15 signaling during the development and activation of NK cells. Nat Immunol 15, 749-757, doi:10.1038/ni.2936 (2014).

Mokhtar, N. M. et al. Progestin regulates chemokine (C-X-C motif) ligand 14 transcript level in human endometrium. Molecular human reproduction 16, 170-177, doi:10.1093/molehr/gap100 (2010).

Kane, N., Kelly, R., Saunders, P. T. & Critchley, H. O. Proliferation of uterine natural killer cells is induced by human chorionic gonadotropin and mediated via the mannose receptor. Endocrinology 150, 2882-2888, doi:10.1210/en.2008-1309 (2009).

Kao, L. C. et al. Global gene profiling in human endometrium during the window of implantation. Endocrinology 143, 2119-2138, doi:10.1210/endo.143.6.8885 (2002).

Gibson, D. A., Greaves, E., Critchley, H. O. & Saunders, P. T. Estrogen-dependent regulation of human uterine natural killer cells promotes vascular remodelling via secretion of CCL2. Hum Reprod 30, 1290-1301, doi:10.1093/humrep/dev067 (2015).

Ewington, L. J., Tewary, S. & Brosens, J. J. New insights into the mechanisms underlying recurrent pregnancy loss. J Obstet Gynaecol Res 45, 258-265, doi:10.1111/jog.13837 (2019).

Santamaria, X., Mas, A., Cervello, I., Taylor, H. & Simon, C. Uterine stem cells: from basic research to advanced cell therapies. Hum Reprod Update 24, 673-693, doi:10.1093/humupd/dmy028 (2018).

Murakami, K et al. Deficiency in clonogenic endometrial mesenchymal stem cells in obese women with reproductive failure—a pilot study. PloS one 8, e82582, doi:10.1371/journal.pone.0082582 (2013).

Castellana, B. et al. Maternal obesity alters uterine NK activity through a functional KIR2DL1/S1 imbalance. Immunol Cell Biol 96, 805-819, doi:10.1111/imcb.12041 (2018).

Perdu, S. et al. Maternal obesity drives functional alterations in uterine NK cells. JCI Insight 1, e85560, doi:10.1172/jci.insight.85560 (2016).

Boots, C. E., Bernardi, L. A. & Stephenson, M. D. Frequency of euploid miscarriage is increased in obese women with recurrent early pregnancy loss. Fertil Steril 102, 455-459, doi:10.1016/j.fertnstert.2014.05.005 (2014).

Leitao, B. et al. Silencing of the JNK pathway maintains progesterone receptor activity in decidualizing human endometrial stromal cells exposed to oxidative stress signals. FASEB journal : official publication of the Federation of American Societies for Experimental Biology 24, 1541-1551 (2010).

Leitao, B. B., Jones, M. C. & Brosens, J. J. The SUMO E3-ligase PIAS1 couples reactive oxygen species-dependent UNK activation to oxidative cell death. FSAEB J 25, 3416-3425, doi:10.1096/fj.11-186346 (2011).

Salker, M. S. et al. Deregulation of the serum- and glucocorticoid-inducible kinase SGK1 in the endometrium causes reproductive failure. Nature medicine 17, 1509-1513, doi:10.1038/nm.2498 (2011).

Kajihara, T. et al. Differential expression of FOXO1 and FOXO3a confers resistance to oxidative cell death upon endometrial decidualization. Mol Endocrinol 20, 2444-2455, doi:10.1210/me.2006-0118 (2006).

Muter, J. et al. Progesterone-Dependent Induction of Phospholipase C-Related Catalytically Inactive Protein 1 (PRIP-1) in Decidualizing Human Endometrial Stromal Cells. Endocrinology 157, 2883-2893, doi:10.1210/en.2015-1914 (2016).

Weyemi, U. et al. ROS-generating NADPH oxidase NOX4 is a critical mediator in oncogenic H-Ras-induced DNA damage and subsequent senescence. Oncogene 31, 1117-1129, 10 doi:10.1038/onc.2011.327 (2012).

Van Deursen JM. Senolytic therapies for healthy longevity. Science, 364, 6441:636-7 (2019).

Zhong J, Rajagopalan S. Dipeptidyl Peptidase-4 Regulation of SDF-1/CXCR4 Axis: Implications for Cardiovascular Disease. Front Immunol. 2015;6:477.

Imai K, Maeda M, Fujiwara H, Kariya M, Takakura K, Kanzaki H, et al. Dipeptidyl peptidase IV as a differentiation marker of the human endometrial glandular cells. Hum Reprod. 1992;7(9):1189-94.

Suhorutshenko M, Kukushkina V, Velthut-Meikas A, Altmae S, Peters M, Magi R, et al. Endometrial receptivity revisited: endometrial transcriptome adjusted for tissue cellular heterogeneity. Hum Reprod. 2018;33(11):2074-86.

(56)        References Cited

OTHER PUBLICATIONS

Wang X, Mamillapalli R, Mutlu L, Du H, Taylor HS. Chemoattraction of bone marrow-derived stem cells towards human endometrial stromal cells is mediated by estradiol regulated CXCL12 and CXCR4 expression. Stem Cell Res. 2015;15(1):14-22.

Yi KW, Mamillapalli R, Sahin C, Song J, Tal R, Taylor HS. Bone marrow-derived cells or C-X-C motif chemokine 12 (CXCL 12) treatment improve thin endometrium in a mouse model. Biol Reprod. 2018.

Deacon CF. A review of dipeptidyl peptidase-4 inhibitors. Hot topics from randomized controlled trials. Diabetes Obes Metab. 2018;20 Suppl 1:34-46.

Barros FS, Brosens, J. J., Brighton, P. J. Isolation and Primary Culture of Various Cell Types from Whole Human Endometrial Biopsies. Bio-protocol. 2016;6:e2028.

Masuda H, Anwar SS, Buhring HJ, Rao JR, Gargett CE. A novel marker of human endometrial mesenchymal stem-like cells. Cell Transplant. 2012;21(10):2201-14.

Turco MY, Gardner L, Hughes J, Cindrova-Davies T, Gomez MJ, Farrell L, et al. Long-term, hormone-responsive organoid cultures of human endometrium in a chemically defined medium. Nat Cell Biol. 2017.

Lash GE, Bulmer JN, Li TC, Innes BA, Mariee N, Patel G, et al. Standardisation of uterine natural killer (uNK) cell measurements in the endometrium of women with recurrent reproductive failure. J Reprod Immunol. 2016;116:50-9.

Murakami K, Bhandari H, Lucas ES, Takeda S, Gargett CE, Quenby S, et al. Deficiency in clonogenic endometrial mesenchymal stem cells in obese women with reproductive failure—a pilot study. PLoS One. 2013;8(12):e82582.

Wang W, Choi BK, Li W, Lao Z, Lee AY, Souza SC, et al. Quantification of intact and truncated stromal cell-derived factor-1alpha in circulation by immunoaffinity enrichment and tandem mass spectrometry. J Am Soc Mass Spectrom. 2014;25(4):614-25.

Du H, Taylor HS. Contribution of bone marrow-derived stem cells to endometrium and endometriosis. Stem Cells. 2007;25(8):2082-6.

Morelli SS, Rameshwar P, Goldsmith LT. Experimental evidence for bone marrow as a source of nonhematopoietic endometrial stromal and epithelial compartment cells in a murine model. Biol Reprod. 2013;89(1):7.

Taylor HS. Endometrial cells derived from donor stem cells in bone marrow transplant recipients. JAMA. 2004;292(1):81-5.

Schachinger V, Erbs S, Elsasser A, Haberbosch W, Hambrecht R, Holschermann H, et al. Intracoronary bone marrow-derived progenitor cells in acute myocardial infarction. N Engl J Med. 2006;355(12):1210-21.

Brenner C, Adrion C, Grabmaier U, Theisen D, von Ziegler F, Leber A, et al. Sitagliptin plus granulocyte colony-stimulating factor in patients suffering from acute myocardial infarction: A double-blind, randomized placebo-controlled trial of efficacy and safety (SITAGRAMI trial). Int J Cardiol. 2016;205:23-30.

Santamaria X, Cabanillas S, Cervello I, Arbona C, Raga F, Ferro J, et al. Autologous cell therapy with CD133+ bone marrow-derived stem cells for refractory Asherman's syndrome and endometrial atrophy: a pilot cohort study. Hum Reprod. 2016;31(5):1087-96.

Alba M, Sheng D, Guan Y, Williams-Herman D, Larson P, Sachs JR, et al. Sitagliptin 100 mg daily effect on DPP-4 Inhibition and compound-specific glycemic improvement. Curr Med Res Opin. 2009;25(10):2507-14.

Farag SS, Nelson R, Cairo MS, O'Leary HA, Zhang S, Huntley C, et al. High-dose sitagliptin for systemic inhibition of dipeptidylpeptidase-4 to enhance engraftment of single cord umbilical cord blood transplantation. Oncotarget. 2017;8(66):110350-7.

Lucas ES, Vrljicak p. Muter J, Diniz-da-Costa M, Brosens JJ, Ott S. "Aberrant specification of endometrial stromal cells into distinct decidual subpopulations in recurrent pregnancy loss", 66th Annual Meeting of the Society for Reproductive Investigation, vol. 26, 2019, p. 198A.

Lucas ES, Vrljicak P, Muter J, Diniz-da-Costa MM, Brighton PJ, Kong CS, Lipecki J, Fishwick KJ, Odendaal J, Ewington LJ, Quenby S, Ott S, Brosens JJ. Recurrent pregnancy loss is associated with a pro-senescent decidual response during the peri-implantation window. Commun Biol. Jan. 21, 2020;3(1):37.

Tewary S, Lucas ES, Fujihara R, et al. Impact of sitagliptin on endometrial mesenchymal stem-like progenitor cells: A randomised, double-blind placebo-controlled feasibility trial. EBioMedicine. 2020;51:102597.

Colombo, A. R., Elias, H. K. & Ramsingh, G. Senescence induction universally activates transposable element expression. Cell Cycle, 1-12, doi:10.1080/15384101.2018.1502576 (2018).

Van Deursen, J. M. The role of senescent cells in ageing. Nature 509, 439-446, doi:10.1038/nature13193 (2014).

Uhlen, M. et al. Proteomics. Tissue-based map of the human proteome. Science 347, 1260419, doi:10.1126/science.1260419 (2015).

The United Kingdom Intellectual Property Office, UK Search Report, Application No. GB1911947.8, dated May 18, 2020.

World Intellectual Property Organization, International Bureau, WO2021/032973 A1, Feb. 25, 2021.

Tewary, Shreeya, Does the DPP4 Inhibitor Sitagliptin Increase the Endometrial Mesenchymal Stem Cell Count in Those with Recurrent Pregnancy Loss?, University of Warwick (2017).

European Patent Office, Communication pursuant to Rule 164(2)(b) and Article 94(3) EPC, European Application Serial No. 20 764 437.8, Aug. 25, 2025.

* cited by examiner

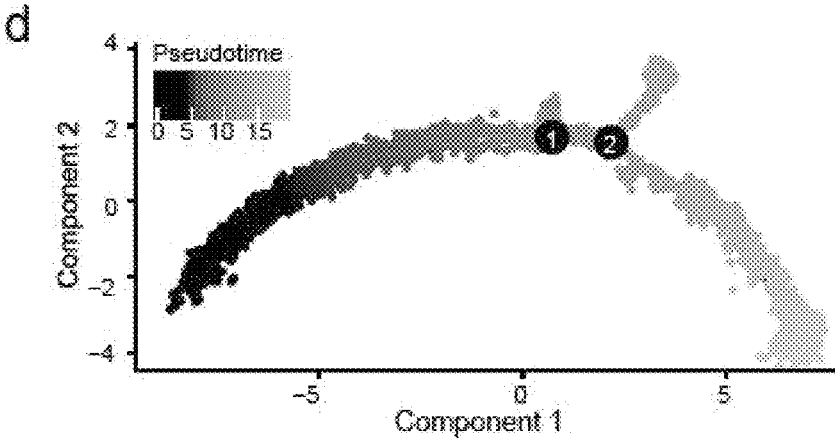
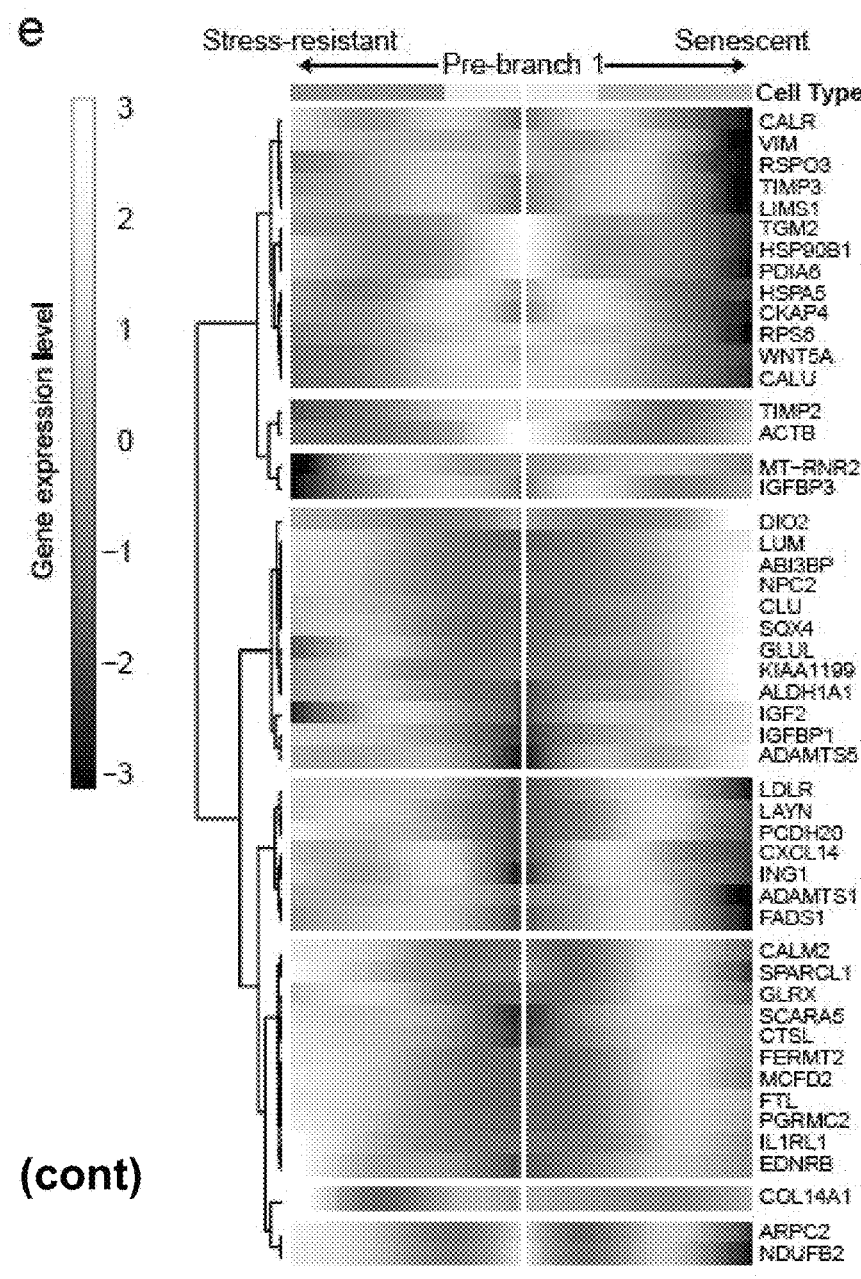
Figure 1 (cont)

a
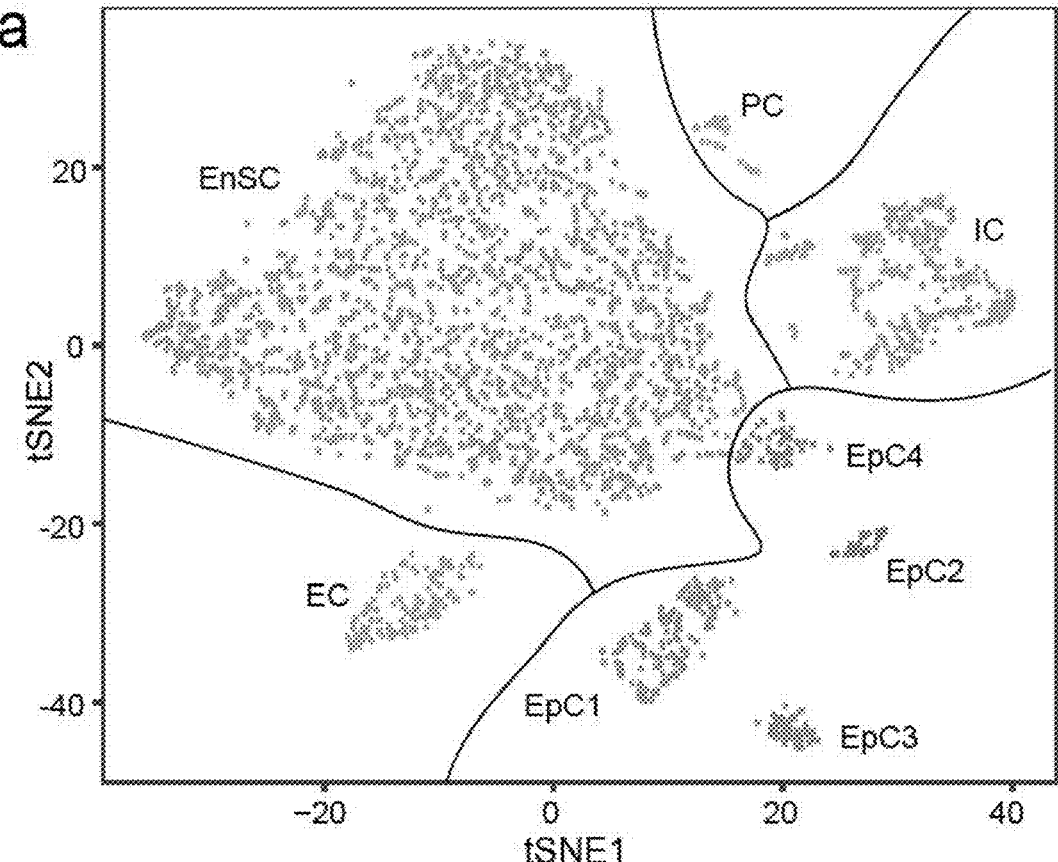
b
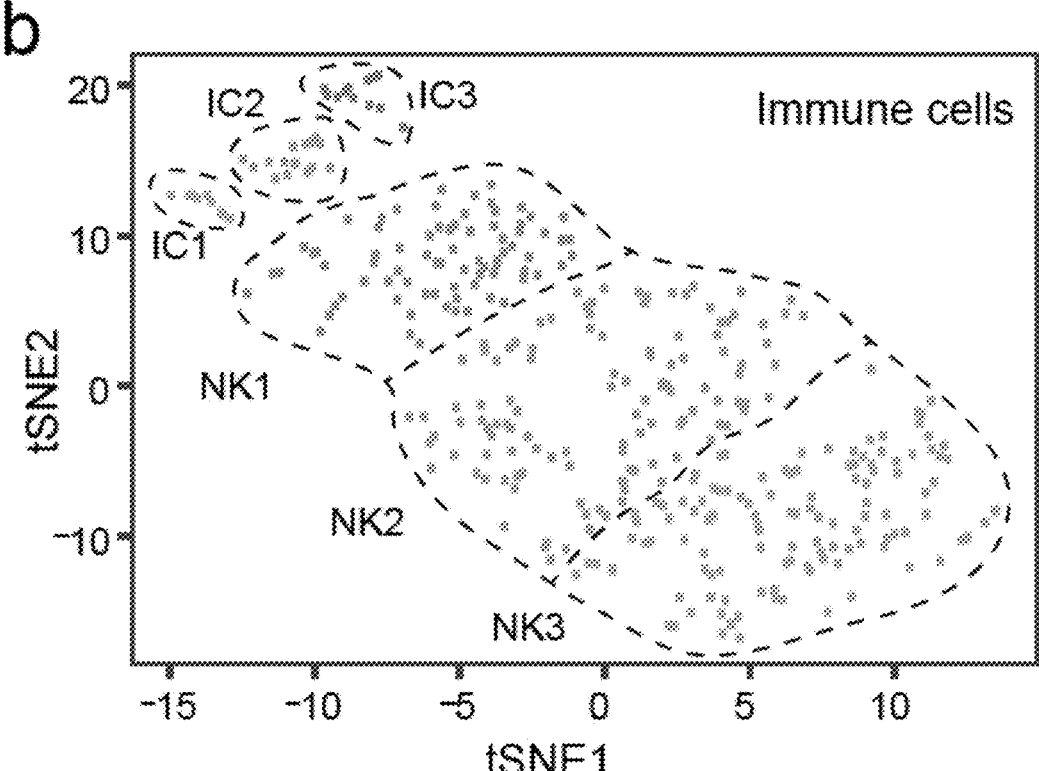
Figure 8

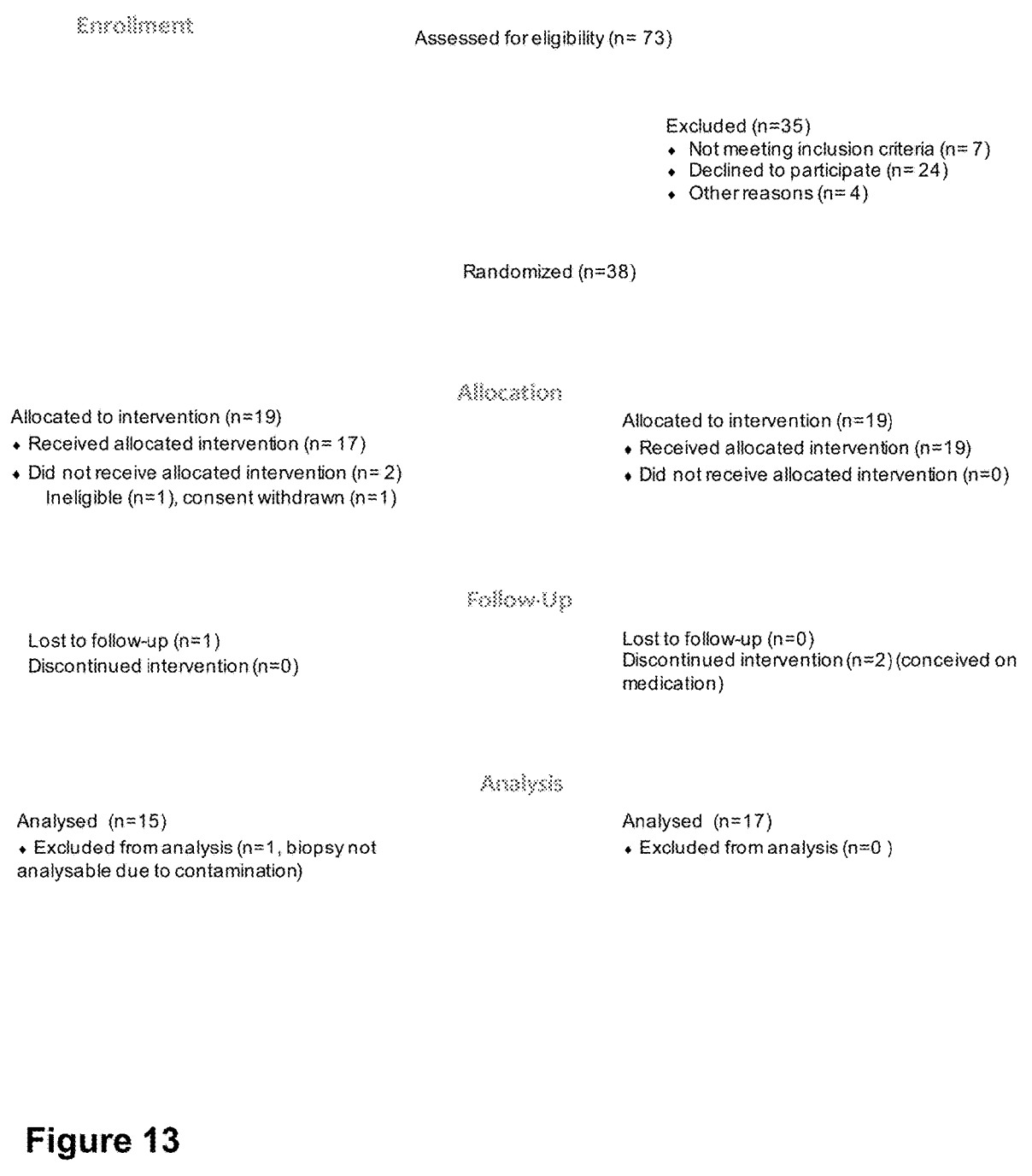

Enrollment

Assessed for eligibility (n= 73)

Excluded (n=35)
♦ Not meeting inclusion criteria (n= 7)
♦ Declined to participate (n= 24)
♦ Other reasons (n= 4)

Randomized (n=38)

Allocation

Allocated to intervention (n=19)
♦ Received allocated intervention (n= 17)
♦ Did not receive allocated intervention (n= 2)
　Ineligible (n=1), consent withdrawn (n=1)

Allocated to intervention (n=19)
♦ Received allocated intervention (n=19)
♦ Did not receive allocated intervention (n=0)

Follow-Up

Lost to follow-up (n=1)
Discontinued intervention (n=0)

Lost to follow-up (n=0)
Discontinued intervention (n=2) (conceived on medication)

Analysis

Analysed (n=15)
♦ Excluded from analysis (n=1, biopsy not analysable due to contamination)

Analysed (n=17)
♦ Excluded from analysis (n=0 )

Figure 13

A
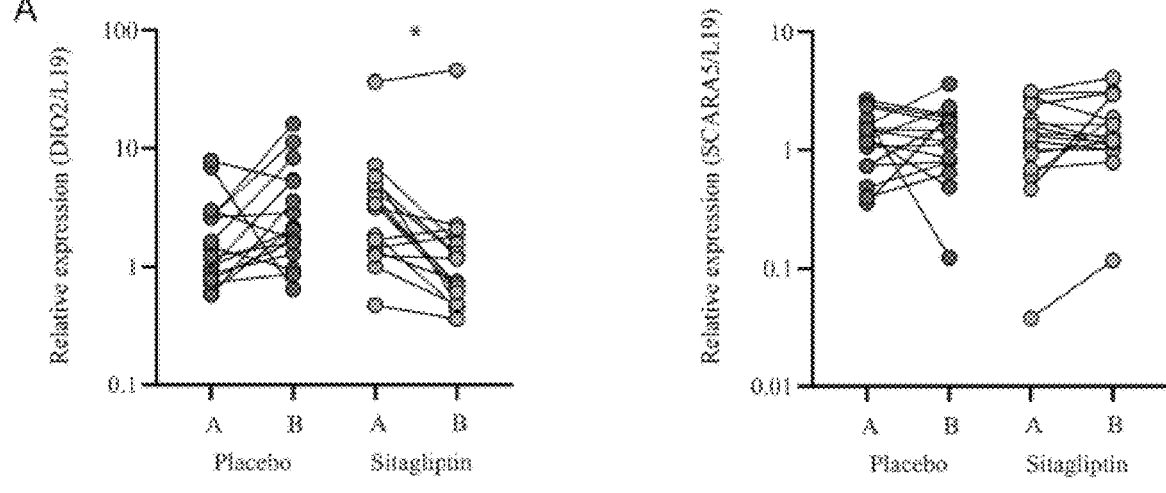
B
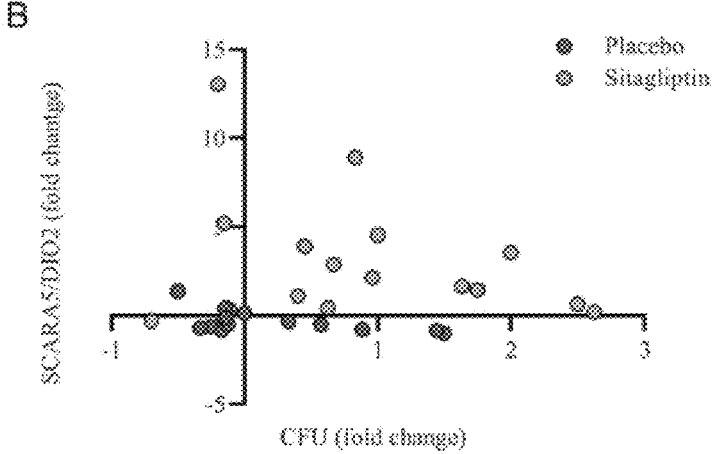
Figure 18

```
                          SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: SCARA5 forward primer

<400> SEQUENCE: 1
catgcgtggg ttcaaaggtg                                          20

<210> SEQ ID NO 2
<211> LENGTH: 20
<212> TYPE: DNA
<213> ORGANISM: Artificial Sequence
<220> FEATURE:
<223> OTHER INFORMATION: SCARA5 reverse primer

<400> SEQUENCE: 2
ccattcacca ggcggatcat                                          20

<210> SEQ ID NO 3
<211> LENGTH: 19
<212> TYPE: DNA
<213> ORGANISM: Artificial Sequence
<220> FEATURE:
<223> OTHER INFORMATION: DIO2 forward primer

<400> SEQUENCE: 3
actcggtcat tctgctcaa                                           19

<210> SEQ ID NO 4
<211> LENGTH: 18
<212> TYPE: DNA
<213> ORGANISM: Artificial Sequence
<220> FEATURE:
<223> OTHER INFORMATION: DIO2 reverse primer

<400> SEQUENCE: 4
ttccagacgc agcgcagt                                            18

<210> SEQ ID NO 5
<211> LENGTH: 19
<212> TYPE: DNA
<213> ORGANISM: Artificial Sequence
<220> FEATURE:
<223> OTHER INFORMATION: L19 forward primer

<400> SEQUENCE: 5
gcggaagggt acagccaat                                           19

<210> SEQ ID NO 6
<211> LENGTH: 14
<212> TYPE: DNA
<213> ORGANISM: Artificial Sequence
<220> FEATURE:
<223> OTHER INFORMATION: L19 reverse primer
```

```
<400> SEQUENCE: 6
gcagccggcg caaa                                              14

<210> SEQ ID NO 7
<211> LENGTH: 25
<212> TYPE: DNA
<213> ORGANISM: Artificial Sequence
<220> FEATURE:
<223> OTHER INFORMATION: PRL forward primer

<400> SEQUENCE: 7
aagctgtaga gattgaggag caaac                                  25

<210> SEQ ID NO 8
<211> LENGTH: 22
<212> TYPE: DNA
<213> ORGANISM: Artificial Sequence
<220> FEATURE:
<223> OTHER INFORMATION: PRL reverse primer

<400> SEQUENCE: 8
tcaggatgaa cctggctgac ta                                     22

<210> SEQ ID NO 9
<211> LENGTH: 20
<212> TYPE: DNA
<213> ORGANISM: Artificial Sequence
<220> FEATURE:
<223> OTHER INFORMATION: DPP4 forward primer

<400> SEQUENCE: 9
ccaaagactg tacgggttcc                                        20

<210> SEQ ID NO 10
<211> LENGTH: 26
<212> TYPE: DNA
<213> ORGANISM: Artificial Sequence
<220> FEATURE:
<223> OTHER INFORMATION: DPP4 reverse primer

<400> SEQUENCE: 10
acaaagaact ttacagttgg attcac                                 26

<210> SEQ ID NO 11
<211> LENGTH: 21
<212> TYPE: DNA
<213> ORGANISM: Artificial Sequence
<220> FEATURE:
<223> OTHER INFORMATION: IGFBP1 forward primer

<400> SEQUENCE: 11
cgaaggctct ccatgtcacc a                                      21

<210> SEQ ID NO 12
<211> LENGTH: 23
<212> TYPE: DNA
<213> ORGANISM: Artificial Sequence
<220> FEATURE:
<223> OTHER INFORMATION: IGFBP1 reverse primer

<400> SEQUENCE: 12
tgtctcctgt gccttggcta aac                                    23
```

SCARA5 AND DIO2 AS BIOMARKERS FOR MISCARRIAGE AND IMPLANTATION FAILURE

FIELD OF THE INVENTION

The invention relates to methods for assessing the risk of miscarriage or embryo implantation failure, and also for monitoring or evaluating the effect of a treatment to reduce the risk of miscarriage or embryo implantation failure using specific biomarkers. The invention also relates to the use of these biomarkers in methods of diagnosing a reproductive disorder in an individual, and also to methods of treating a reproductive disorder. In addition, the biomarkers can further be used in methods of selecting patients for treatment to reduce risk of embryo implantation failure or miscarriage. The invention also relates to kits for use in any of the methods described herein.

BACKGROUND TO THE INVENTION

Approximately 15% of clinical pregnancies result in miscarriage[1], most often during the first trimester. Fetal chromosomal abnormalities account for 50-60% of miscarriages[2,3], and the incidence of aneuploid pregnancies is increasing in developed countries, paralleling the demographic shift towards older maternal age[2]. Aneuploid miscarriage is less prevalent in recurrent pregnancy loss (RPL)[4-8], defined as two or more losses[9,10]. With each additional miscarriage, the frequency of a euploid loss increases whereas the likelihood of a successful pregnancy decreases 4. While these observations indicate that maternal factors drive higher-order miscarriages, few interventions improve live-birth rates in RPL[9], reflecting that in many cases the underlying mechanism is unknown.

Mounting evidence from animal studies suggests that dysregulated interactions between the conceptus and endometrium at implantation cause ripple effects that ultimately result in pregnancy failure[11-13]. Implantation requires intense remodeling of the endometrial stroma, driven by the postovulatory progesterone surge and rising intracellular cyclic adenosine monophosphate levels[14]. This process, termed decidualization, is initiated during the midluteal phase of each cycle and involves differentiation and polarization of endometrial stromal cells (EnSC) into stress-resistant and stressed/senescent decidual subpopulations[15]. In parallel, uterine natural killer (uNK) cells accumulate in the stroma and, in response to IL-15 activation, target stressed decidual cells for elimination. Upon implantation, embryo-derived chorionic gonadotrophin rescues the corpus luteum and sustained progesterone signaling promotes the formation of a tightly connected, immune-privileged decidual matrix around the conceptus[16]. Thus, a critical challenge at implantation is to simultaneously avoid imminent endometrial breakdown while transforming the cycling endometrium into a semi-permanent tissue, the decidua, maintained throughout pregnancy.

Pre-pregnancy screening and intervention may reduce the burden of miscarriage.

SUMMARY OF THE INVENTION

In the present invention, the inventors surprisingly found that aberrant levels of markers of decidual cells and/or senescent decidual cells were associated with reproductive defects such as miscarriage. The inventors employed high-throughput single-cell droplet barcoding to profile the transcriptome changes along the decidual pathway in vitro, to characterize the diverging decidual subpopulations, and to define cellular responses to withdrawal of the differentiation signal. The scRNA-seq analysis was extended to luteal-phase endometrial biopsies and genes such as SCARA5 and DIO2 were identified as selective marker genes for decidual (stress-resistant) cells and senescent decidual cells, respectively. Based on analysis of uNK cells and SCARA5 and DIO2 expression in endometrial biopsies from RPL and control subjects, a conspicuous link was demonstrated between decidual dyshomeostasis and RPL, and the utility of markers specific for decidual and senescent decidual cells (and for uNK cells) in assessing reproductive defects such as risk of miscarriage was illustrated. The inventors also surprisingly illustrated a decrease in a marker for senescent decidual cells in patients with recurrent miscarriage following treatment with an agent effective in treating such patients, and thus that the markers of the invention may be used to select patients for treatment and to monitor for successful treatment.

Thus, the present inventors have surprisingly identified particular biomarkers that can be used alone or in combination in methods for assessing the risk of miscarriage or embryo implantation failure, and also for monitoring or evaluating the effect of a treatment to reduce the risk of miscarriage or embryo implantation failure. These biomarkers can also be used in methods of diagnosing a reproductive disorder in an individual, and also to assist methods of treating a reproductive disorder. In addition, these biomarkers can further be used in methods of selecting patients for treatment to reduce risk of embryo implantation failure or miscarriage, methods of stratifying patients. The biomarkers may be detected using kits as described herein.

The present invention thus provides a method for assessing the risk of miscarriage or embryo implantation failure in an individual, wherein the method comprises detecting and/or quantifying the amount of at least one marker gene for decidual cells and at least one marker gene for decidual senescent cells in a biological sample obtained from the individual, and thereby assessing the risk.

The present invention also provides a method of monitoring or evaluating the effect of a treatment to reduce the risk of miscarriage or embryo implantation failure in an individual, wherein the method comprises detecting and/or quantifying the amount of at least one marker gene for decidual cells and at least one marker gene for decidual senescent cells in a biological sample obtained from the individual, and thereby monitoring or evaluating the effect of the treatment.

The present invention further provides a method of diagnosing a reproductive disorder in an individual, wherein the method comprises detecting and/or quantifying the amount of at least one marker gene for decidual cells and at least one marker gene for decidual senescent cells in a biological sample obtained from the individual, thereby diagnosing the disorder.

The present invention also provides a method of treating a reproductive disorder in an individual, or of preventing miscarriage or embryo implantation failure in an individual, the method comprising diagnosing the reproductive disorder or assessing the risk of miscarriage or embryo implantation failure as described herein, and administering an agent or carrying out a treatment regimen effective to treat the reproductive disorder or prevent miscarriage or embryo implantation failure in the individual who is positively diagnosed or assessed as being at risk.

The present invention also provides a method of selecting patients for treatment to reduce risk of embryo implantation failure or miscarriage, wherein the method comprises detecting and/or quantifying the amount of at least one marker gene for decidual cells and at least one marker gene for decidual senescent cells in a biological sample obtained from an individual, and selecting the patients for treatment to reduce the risk of miscarriage or embryo implantation failure based on the level of the marker genes.

The present invention also provides a test kit suitable for use in a method described herein, wherein the test kit comprises means for detecting or quantifying at least one marker gene for decidual cells and at least one marker gene for decidual senescent cells at a nucleic acid or protein level, and optionally means for detecting and/or quantifying the level of uNK cells or the level of at least one marker gene for uNK cells in the individual.

The invention further provides a method of assessing readiness for conception or successful embryo implantation in an individual comprising detecting and/or quantifying the amount of at least one marker gene for decidual cells and at least one marker gene for decidual senescent cells in a biological sample obtained from the individual, and thereby assessing readiness for conception or successful embryo implantation.

BRIEF DESCRIPTION OF THE FIGURES

FIG. 13: Consort flow diagram. The number of study participants that progressed through the phases of the randomised trial are summarised: enrolment, intervention allocation, follow-up, and data analysis.

DPP4 expression and activity were not significantly different between the groups (P>0.025, Wilcoxon test).

Figure 16:
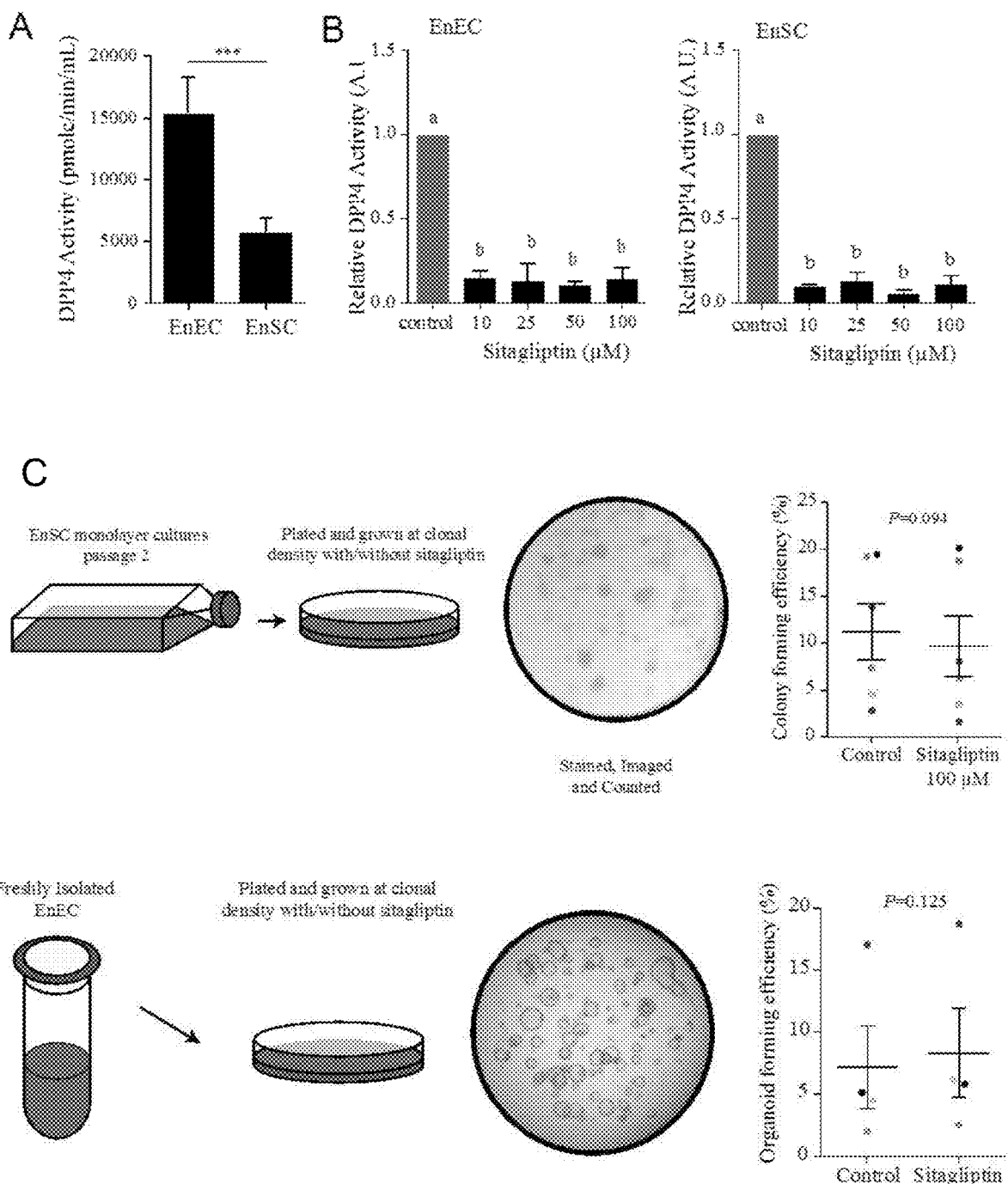

FIG. 16: Analysis of sitagliptin actions in primary endometrial cell culture. (A) Secreted DPP4 enzyme activity was measured in primary EnEC (n=9) and EnSC (n=11) cultures; *** denotes P<0.001. (B) Sitagliptin inhibits secreted DPP4 activity in primary EnEC (n=4) and EnSC (n=5) cultures at all concentrations tested. Different letters above the error bars indicate groups are significantly different from each other at P<0.05. (C) CFU assays (n=4; top panel) and OFE assays (n=6; bottom panel) were performed as schematically depicted in the presence of sitagliptin (100 μM) or vehicle control. The presence of sitagliptin did not alter the colony-forming activity of EnSC or organoid-forming activity of EnEC (P>0.05). Paired cultures from different biopsies are indicated by matched dots.

Figure 17:
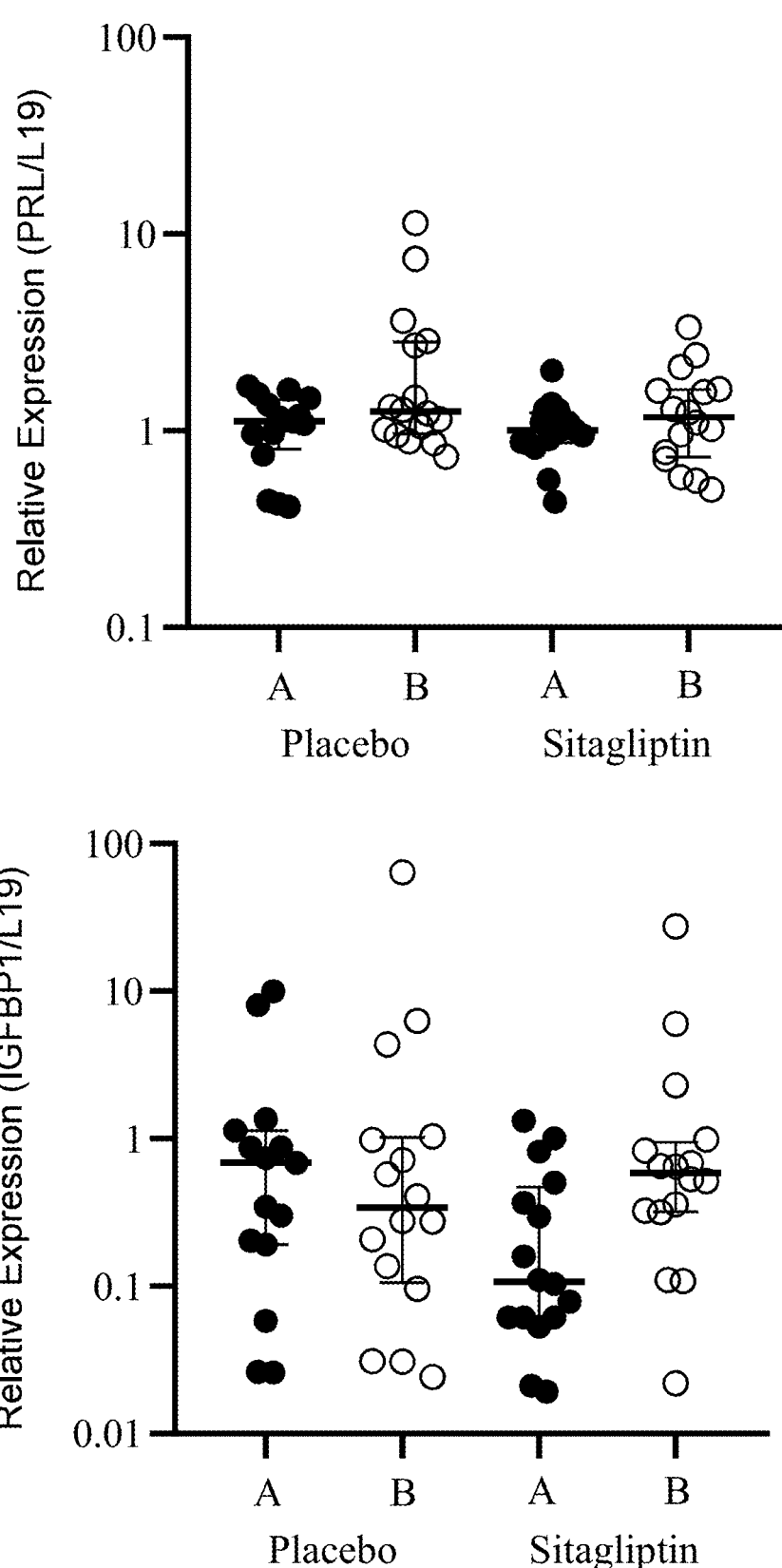

FIG. 17: Oral sitagliptin does not inhibit endometrial PRL and IGFBP1 expression. PRL and IGFBP1 transcript levels, normalized to L19, were measured by RT-qPCR in paired baseline (A) and second (B) endometrial biopsies obtained from participants randomised to placebo (PRL n=16, IGFBP1 n=15) or sitagliptin (n=16). Expression of both markers was not significantly different between the groups (P>0.025, Wilcoxon test).

FIG. 18: Oral sitagliptin inhibits decidual senescence. (A) DIO2 and SCARA5 mRNA levels DPP4 mRNA level, normalized to L19 and expressed as arbitrary units, was measured by RT-qPCR in paired baseline ($1^{st}$) and second ($2^{nd}$) endometrial biopsies obtained from participants randomised to placebo (n=16) or sitagliptin (n=16). * indicates P=0.0182 (Wilcoxon test). (B) The relative change in the ratio of SCARA5 and DIO2 transcripts is shown in relation to the change in CFU counts in paired endometrial biopsies from the placebo (dark grey dots) and sitagliptin (light grey dots) groups.

DETAILED DESCRIPTION OF THE INVENTION

It is to be understood that different applications of the disclosed methods may be tailored to the specific needs in the art. It is also to be understood that the terminology used herein is for the purpose of describing particular embodiments of the invention only, and is not intended to be limiting. All publications, patents and patent applications cited herein, whether supra or infra, are hereby incorporated by reference in their entirety.

As used in this specification and the appended claims, the singular forms "a", "an", and "the" include plural referents unless the content clearly dictates otherwise. Thus, for example, reference to "a cell" includes "cells", and the like.
Method for Assessing the Risk of Miscarriage or Embryo Implantation The invention provides a method for assessing the risk (or likelihood or probability) of miscarriage or embryo implantation failure in an individual, wherein the method comprises detecting and/or quantifying the amount of at least one marker gene for decidual cells and at least one marker gene for decidual senescent cells in a biological sample obtained from the individual, and thereby assessing the risk.

The at least one marker gene for decidual cells and at least one marker gene for decidual senescent cells may be selected from any such marker genes. Thus, the marker genes may be any genes indicative of the levels of decidual cells and decidual senescent cells in the sample, such as an endometrial sample. For example, a marker gene for decidual cells may be any marker whose decrease is indicative of a decreased level of decidual cells, and a marker gene for decidual senescent cells may be any marker whose increase is indicative of an increased level of decidual senescent cells.

The level of the marker genes is typically compared with a control sample or reference sample or level. Any suitable control sample or reference sample or level may be used. A control sample or reference sample or level may represent a normal or healthy sample/level, for example obtained or determined from an individual or multiple individuals not having any reproductive disorder, or not having had miscarriage or embryo implantation failure. The individual(s) may have had one or more successful pregnancies. The control or reference sample or level may also be obtained or determined from an individual or multiple individuals who have responded positively to treatment to reduce the risk of miscarriage or embryo implantation failure. Alternatively a control sample or reference sample or level may represent a sample/level from an individual or multiple individuals having a reproductive disorder, or who have had one or more miscarriages or embryo implantation failures, i.e a positive control or reference sample or level. In the case of control or reference samples or levels from multiple individuals, an average value may be obtained or the results may be pooled to generate a more accurate reference range. The level determined in the test sample is preferably compared to a control or reference sample or level that is obtained on or around the same day of the menstrual cycle as the test sample. Other suitable control or reference samples or levels can readily be identified by the person skilled in the art.

A decreasing or decreased level of a marker gene for decidual cells e.g. SCARA5 in a sample, as compared with a reference sample or level, may indicate that the individual is at risk of miscarriage or embryo implantation failure. Alternatively, an increasing or increased level of a marker gene for decidual senescent cells e.g. DIO2, as compared with a reference sample or level, may indicate that the individual is at risk of miscarriage or embryo implantation failure. The level of marker gene can be determined using any methods described herein and that are known to the skilled person. In one instance, a decreasing or decreased level of a marker gene for decidual cells e.g SCARA5, as compared with a reference sample or level, and an increasing or increased level of a marker gene for decidual senescent cells e.g DIO2, as compared with a reference sample or level, together indicate that the individual is at risk of miscarriage or embryo implantation failure.

In one instance, the method for assessing the risk of miscarriage or embryo implantation failure in an individual further comprises detecting and/or quantifying the level of uterine natural killer (uNK) cells in the sample, for example based on the level of at least one marker gene for uNK cells in the sample.

A decreasing or decreased level of the uNK cells or uNK cell gene markers in a sample, as compared with a reference sample or level, may indicate that the individual is at risk of miscarriage or embryo implantation failure.

The method of the invention may also further comprise detecting and/or quantifying genes that allow identification of the day in the menstrual cycle as described below.

Further risk indicia, which may be used to assess the risk of miscarriage or embryo implantation failure, include maternal body mass index (BMI), maternal age, number of previous miscarriages or embryo implantation failures, familial and intergenerational factors, history of infertility, placental abnormalities, cervical and uterine anomalies, smoking, alcohol consumption, etc. Additional risk indicia are known to those of skill in the art.

For instance, there may be an increased risk of miscarriage or embryo implantation failure if the maternal BMI is too low (e.g. <18.5) or too high (e.g. >25), if the maternal age is 35 and above, if there has been a history of recurrent miscarriages (e.g. when a woman has had 2 or more miscarriages before the pregnancies reached 20 weeks).

Samples

As used herein, the term "biological sample" or "sample" refers to any sample that is taken from an individual. Suitable samples in the context of the methods of the present invention include, for example, endometrial tissue, endometrial secretions, cells obtained from the endometrium, or an endometrial biopsy sample.

A sample obtained from the endometrium may be collected by any method known in the art, including through an endometrial biopsy or endometrial sampling. The technique involves removing a piece of tissue from the inner lining of the uterus (endometrium). The sample may also be obtained using a dilation and curettage procedure.

The sample may be or may have been processed prior to use, for example by dilution, centrifugation or extraction of DNA, RNA or protein. The sample may be a freshly obtained sample or may be or have been stored or preserved, e.g. by freezing, prior to use.

The sample may be taken during the luteal phase of the menstrual cycle. The luteal phase begins with the formation of the corpus luteum, with progesterone being significantly higher than in other phases of the menstrual cycle. The sample may be taken during the mid-luteal phase of the menstrual cycle. The sample is thus typically taken post-ovulation. The sample is typically taken during the embryo implantation window (also known as the receptivity window), of the menstrual cycle, in which the endometrium is receptive to implantation of an embryo. The embryo implantation window may be determined by any means, and may for example be calculated based on an ovulation test. An ovulation test may be based on hormone level, such as luteinizing hormone (LH) level (for example LH level in urine) or oestrogen level (for example based on salivary ferning). Alternatively, the level of one or more markers indicative of receptivity to embryo implantation may be determined. The sample may be taken between about 5 and about 11 days after an increase or surge (such as a 2-5 fold increase or surge) in the level of LH s, i.e. LH+5 to LH+11. LH is produced by the pituitary gland and is generally secreted at very low levels throughout the menstrual cycle, with the ovulatory phase of the menstrual cycle however beginning with a surge in LH.

The sample type and timing of sampling described above is applicable to any of the methods of the present invention detecting marker levels.

Individual

The individual referred to in any of the methods of the invention may be a human or a non-human menstruating mammal. The methods described herein may thus be applied in a veterinary context. The subject is preferably a human female.

The individual may be suffering or have suffered from infertility or embryo implantation failure. For instance, the individual may suffer from or have suffered from embryo implantation failure following in vitro fertilisation treatment. The individual may have suffered from at least one previous miscarriage or multiple miscarriages, and/or at least one embryo implantation failure or multiple embryo implantation failures. The individual may suffer from recurrent pregnancy loss (RPL).

The individual may already be considered to be at risk of miscarriage or embryo implantation failure. The individual may be considered at risk of miscarriage or embryo implantation failure due to the presence of one or more of the risk indicia, including low or high body mass index (BMI), maternal age, number of previous miscarriages or embryo implantation failures, familial and intergenerational factors, history of infertility, placental abnormalities, cervical and uterine anomalies etc. Additional risk indicia for miscarriage or embryo implantation failure are known to those of skill in the art.

Miscarriage

"Miscarriage" typically refers to the loss of a pregnancy, particularly in the first 20 to 23 weeks of gestation. Typical symptoms of a miscarriage comprise vaginal bleeding with or without pain, and also cramping and pain in the lower abdomen. When multiple miscarriages occur, an individual may be diagnosed as suffering from RPL or infertility.

A majority of miscarriages are thought to be caused by chromosomal abnormalities or errors in the embryo, such as aneuploidy, e.g. autosomal trisomy, monosomy X, triploidy, tetraploidy etc. Other miscarriages are not due to chromosomal abnormalities or errors in an embryo.

In a method of the present invention, the risk of miscarriage may be assessed. The method of the invention is preferably used for determining the risk of euploid miscarriage, and where the cause of miscarriage is not due to a chromosomal abnormality or error in an embryo.

Embryo Implantation Failure

After fertilisation, a fertilised egg (or zygote) begins to divide by mitosis to produce an embryo. The process of the embryo attaching to the lining of the uterus, i.e. the endometrium, is known as implantation. "Embryo implantation failure" or "implantation failure" in accordance with the invention refers to failure of an embryo to be implanted into the endometrium. Implantation failure may occur either where patients are trying to conceive naturally, without any fertility treatment or after undergoing assisted reproductive technology e.g. in vitro fertilisation (IVF).

Some cases of implantation failure are thought to be caused by chromosomal abnormalities in the embryo, such as aneuploidy, e.g. autosomal trisomy, monosomy X, triploidy, tetraploidy etc. Other cases of embryo implantation failure are not due to chromosomal abnormalities or errors in an embryo. Some cases of implantation failure related to IVF are caused by poor embryo quality, the age of the eggs, a lack of response to IVF medication or other lifestyle factors (e.g. smoking).

According to the present invention, the risk of any case of embryo implantation failure may be assessed in any setting. The method of assessing risk of embryo implantation failure of the invention may thus be used for determining risk of implantation failure following natural conception, or the risk of implantation failure following assisted reproduction in an individual, for example following in vitro fertilisation. The method is preferably used for determining the risk of embryo implantation failure that is not due to a chromosomal abnormality or error in an embryo.

Decidual Cells and Decidual Senescent Cells and Marker Genes

In accordance with the method of assessing risk of miscarriage or implantation failure of the present invention, at least one marker gene for decidual cells and at least one marker gene for decidual senescent cells are detected and/or quantified.

When exiting the cell cycle, a cell either differentiates into a specialised cell or becomes senescent. Cellular senescence is a defined cellular state, which can be acute or chronic. A key characteristic of senescent cells (SNCs) is that they are in a state of permanent cell-cycle arrest, typically initiated and maintained by the p53-p21-retinoblastoma (RB) and p16-RB tumour suppressor pathways. SNCs produce a bio-active "secretome," referred to as the senescence-associated secretory phenotype (SASP), which can disrupt normal tissue architecture and function through diverse mechanisms, including recruitment of inflammatory immune cells, remodelling of the extracellular matrix, induction of fibrosis, and inhibition of stem cell function[58].

During decidualization, the cells of the endometrium undergo significant changes in preparation for and during pregnancy. During this process, endometrial stromal cells (EnSC) either become a specialised cell (i.e. decidual cell) or become acutely senescent (i.e. decidual SNC).

The decidual cell detected may be any decidual cell and the decidual senescent cell detected any decidual senescent cell, typically any such cells in an endometrial sample. A decidual or decidual senescent cell is typically derived from an endometrial stromal cell. Decidual cells are stress-resistant and are also described herein as stress-resistant decidual cells.

In accordance with the method of assessing risk of miscarriage or implantation failure of the present invention, any marker gene for decidual cells and any marker gene for decidual senescent cells may be detected. The marker genes for decidual cells are typically selected from one or more of SCARA5, FTL, GLRX and IL1RL1, and the marker genes for decidual senescent cells are typically selected from one or more DIO2, CLU and IGFBP1. Preferably, the at least one marker gene for decidual cells is SCARA5. The method may comprise detecting a decrease in SCARA5. Preferably, the at least one marker gene for decidual senescent cells is DIO2. The method may comprise detecting an increase in DIO2. In a preferred embodiment, the at least one marker gene for decidual cells is SCARA5 and the at least one marker gene for decidual senescent cells is DIO2, and the method comprises detecting and/or quantifying the amount of both SCARA5 and DIO2. The method may comprise detecting a decrease in SCARA5 and an increase in DIO2. Any of the above genes may be detected and/or quantified in the method for assessing the risk of miscarriage or embryo implantation failure of the invention, as well as in further methods described below.

Centile or percentile graphs may be employed to compare expression levels of marker genes such as marker genes of decidual and decidual senescent cells (and also levels of other markers as discussed below) in samples obtained at different days in the menstrual cycle. Centile graphs are based on the statistical distribution of the expression levels of a given marker gene on a given day in the menstrual cycle, e.g. following a positive ovulation test. The more samples used to generate the centile graphs, the more accurate the reference range. For instance, centile graphs may be based on at least 10 samples, at least 100 samples, at least 250 samples, at least 500 samples, at least 1000 samples, at least 2000 samples, at least 5000 samples, or more. The relative expression level of a given marker gene (i.e. centile) in a sample of an individual obtained on a given day in the menstrual cycle may be calculated against the reference percentile graph.

In some instances, the determination of the centile for each marker gene allows the cause and clinical presentation of the individual to be determined, such as that for recurrent pregnancy loss. Putative defects, or decidual dyshomeostasis, along the decidual pathway may be determined. In one example, a low level of a decidual cell marker gene e.g. SCARA5 and a high level of decidual senescent cell marker gene e.g. DIO2, as compared with a reference sample or reference level, is indicative of excessive decidual senescence, and occurs more frequently in recurrent pregnancy loss. In a particular instance, where the level of a decidual cell marker gene e.g. SCARA5 is in or below the lower 30th centile and the level of a decidual senescent cell marker gene e.g. DIO2 being in or above the 70th centile, as compared with a reference sample or reference level, then there is a positive diagnosis, and the disorder is related to excessive decidual senescence. Where there is a low level of a decidual cell marker gene e.g. SCARA5 and a low level of decidual senescent cell marker gene e.g. DIO2, this may be indicative of decidual failure, and occurs more frequently in individuals suffering from recurrent implantation failure following IVF treatment.

uNK Cells and uNK Cell Gene Markers

In accordance with the method of assessing risk of miscarriage or implantation failure of the invention, in addition to the marker genes for decidual cells and decidual senescent cells, levels of uterine natural killer (uNK) cells may also detected and/or quantified, typically by detection of one or more marker genes for uNK cells.

Successful transition of the endometrium (from a cycling tissue into a semi-permanent tissue capable of maintaining the placenta throughout pregnancy) is dependent on stress-resistant decidual cells co-opting uterine natural killer (uNK) cells to eliminate their acutely stressed counterparts, i.e. decidual senescent cells, through granule exocytosis. Thus, the balance of diverging decidual populations and uNK cells during the midluteal phase of the menstrual cycle is described herein to likely determine the ability of the endometrium to transition into a pregnancy tissue. Imbalance in decidual subsets is also linked herein to reproductive failure. Thus, determination of the level of uNK cells in combination with detecting levels of markers for decidual and decidual senescent cells provides additional information for assessment of the risk of miscarriage or implantation failure and also in relation to diagnosis of reproductive disorders more generally.

The level of uNK cells in the sample may be detected and/or quantified by any means known in the art. uNK cells may be detected and/or quantified using immunohistochemistry and image analysis. Alternatively, uNK cells may be detected based on the level of at least one marker gene for uNK cells in the sample.

In accordance with the methods of the present invention, any uNK cell gene marker may be detected and/or quantified. Marker genes for uNK cells may be selected from NCAM1, KLRB1, KLRC1, GZMA, GZMB, IL2RB and IL2RG. The above genes may be detected and/or quantified in the method for assessing the risk of miscarriage or embryo implantation failure described herein, and also in further methods of the invention detecting marker genes as described below. The level of uNK cells may also be determined as a centile as described above. In one example, where the level of both a decidual cell marker gene e.g. SCARA5 and a decidual senescent cell marker gene e.g. DIO2 is above the 30th centile but below the 70th centile, and where the level of uNK cells is in or below the 30th centile, as compared with a reference sample or reference level, then there is a positive diagnosis, and the disorder may be related to uNK cell deficiency. uNK cell deficiency occurs more frequently in recurrent pregnancy loss.

Determination of the Timing in the Menstrual Cycle

In accordance with the methods of the present invention, a determination of the time (such as the point, stage or day) in the menstrual cycle on which the sample is obtained may be additionally carried out. Any parameter including any known hormone, marker or other parameter (including any hormone or marker described above) that allows timing of the point, stage or day in the cycle may be used. Preferably, the sample is obtained in the embryo implantation window, and the point, stage or day within the embryo implantation window is determined. The determination of the point, stage or day in the menstrual cycle advantageously allows a sample to be compared to a reference sample or level representative of the same point, stage or day, since the hormone levels or marker gene levels change throughout the cycle.

In a particular embodiment, in addition to marker genes for decidual cells, decidual senescent cells and/or uNK cells, marker genes that allow identification of the point, stage or day in the menstrual cycle are thus also detected and/or quantified. Such marker genes are also referred to herein as molecular timing genes, and are typically indicative of timing in the implantation window. Through the analysis of these genes, the accuracy of the detection based on analysis of the marker genes for decidual cells and decidual senescent cells and/or uNK cell or uNK cell marker genes may be improved.

The purpose of molecular timing is two-fold. Because of cycle-dependence of levels, the interpretation of the levels of the decidual cell gene markers e.g. SCARA5, the decidual senescent cell gene markers e.g. DIO2 and/or uNK cell levels or uNK cell gene markers, is advantageously assisted by knowledge of the day a biopsy is taken in the cycle. Practically, this may also be achieved by scheduling the biopsy relative to the pre-ovulatory luteinising hormone (LH) surge as discussed above. The methods of the invention may thus be carried out in an individual by obtaining a sample at a suitable time point subsequent to an LH surge as described above. However, by considering molecular timing based on analysis of marker gene expression, the risk of erroneous timing of the biopsy due to patient error and intrinsic variation between the LH surge and the exact time of ovulation may be reduced.

The window of implantation (also known as the receptivity window) is associated with dramatic changes in gene expression in the glandular epithelium. Thus, the method of the invention may preferably comprise detection of any marker gene having a change in expression (and which is typically selectively expressed) in the glandular epithelium during the implantation window and thus able to report on the point, stage or day in the embryo implantation window. The determination may preferably be based on two or more genes that are selectively expressed in the glands and that exhibit opposing expression profiles as the menstrual cycle progresses. The ratio of two or more such genes may be determined.

Marker genes that enable determination of the molecular timing of the embryo implantation window and may be used according to the invention include any one or more of GPX3, DPP4 (a GPX3-like gene), SLC15A2 and CTNNA2 (a SLC15A2-like gene). Preferably, the marker genes that enable determination of the molecular timing of the embryo implantation window are GPX3 and SLC15A2. The ratio of GPX3 and SLC15A2 may thus be determined. Because molecular timing as used in the invention is typically based on genes selectively expressed in epithelial cells such as GPX3 and SC15A2, whereas decidual cell and decidual senescent cell markers e.g. SCARA5 and DIO2 are selective stromal cell markers, molecular timing may also be used to diagnose asynchrony between the hormonal response in the epithelial and stromal compartment. As described herein, GPX3 and SLC15A2 are regulated in opposing ways as the luteal phase unfolds (i.e. GPX3 is rapidly upregulated whereas SLC15A2 is rapidly downregulated). Consequently, the ratio of these two genes changes profoundly from day to day during the implantation window. The ratio between GPX3 and SLC15A2 rises markedly across LH+5 and LH+11 days of the cycle (as discussed in Example 2) and thus the ratio between GPX3 and SLC15A2 may be matched to a particular day in the cycle. The particular GPX3/SLC15A2 ratio may be matched to a particular day in the cycle based on a centile/percentile graph plotted from values obtained from pooled reference samples for that particular day in the cycle, for example as obtained by detection of the LH surge (e.g. using home ovulation kits). Preferably, if the GPX3/SLC15A2 ratio in a test sample falls between the $25^{th}$ to $75^{th}$ percentile of a reference centile/percentile graph plotted from values obtained from pooled reference samples for a particular day in the cycle, and matches (i.e. is congruent) with the day of the luteal phase as determined by detection of the LH surge (e.g. using a home ovulation kit), then the timing of a biopsy may be considered improved in accuracy, and test results may be reported on the basis of the day in the cycle as determined by detection of the LH surge e.g. using a home ovulation kit. If the GPX3/SLC15A2 ratio in a test sample falls outside of the $25^{th}$ to $75^{th}$ percentile of a reference centile/percentile graph plotted from values obtained from pooled reference samples for a particular day in the cycle (i.e. is incongruent), or if the GPX3/SLC15A2 ratio does not match with the day of the luteal phase as determined by detection of the LH surge (e.g. using a home ovulation kit), then the timing of a biopsy may be considered less accurate, and test results may be reported both on the basis of the day in the cycle as determined by detection of the LH surge e.g. using a home ovulation kit, as well as based on molecular timing results.

Marker Gene Sequences

Particular sequences for marker genes useful in accordance with the present invention, with their database accession/identification number in the NCBI Gene database, Ensembl database and OMIM database are disclosed herein. The gene sequences as disclosed herein include those available with reference to these online sequence databases as of 16 Jun. 2019. Thus, below is a list of marker genes with representative accession numbers (in parentheses: NCBI Gene database, followed by Ensembl database, followed by OMIM database) and alternative gene names (in italics):

SCARA5 (286133, ENSG00000168079, 611306) Tesr, NET33, FLJ23907, MGC45780;

FTL (2512, ENSG00000087086, 134790) LFTD, NBIA3, MGC71996;

GLRX (2745, ENSG00000173221, 600443) GRX, GRX1;

IL1RL1 (9173, ENSG00000115602, 601203) T1, ST2, DER4, ST2L, ST2V, FIT-1, IL33R;

DIO2 (1734, ENSG00000211448, 601413) D2, 5DII, SelY, DIOII, TXDI2;

CLU (1191, ENSG00000120885, 185430) CLI, AAG4, APOJ, CLU1, CLU2, KUB1, SGP2, APO-J, SGP-2, SP-40, TRPM2, TRPM-2, NA1/NA2;

IGFBP1 (3484, ENSG00000146678, 146730) AFBP, IBP1, PP12, IGF-BP25, hIGFBP-1;

GPX3 (2878, ENSG00000211445, 138321) GPx-P, GSHPx-3, GSHPx-P;

SLC15A2 (6565, ENSG00000163406, 602339) PEPT2;

DPP4 (1803, ENSG00000197635, 102720) CD26, ADABP, ADCP2, DPPIV, TP103;

CTNNA2 (1496, ENSG00000066032, 114025) CAPR, CTNR, CAP-R, CT114, CDCBM9;

IL2RB (3560, ENSG00000100385, 146710) CD122, IL15RB, P70-75;

IL2RG (3561, ENSG00000147168, 308380) P64, CIDX, IMD4, CD132, SCIDX, IL-2RG, SCIDX1;

NCAM1 (4684, ENSG00000149294, 116930) CD56, NCAM, MSK39.

Detection and/or Quantification of the Amount/Level of the Biomarkers

As used herein, the term "marker gene" or "biomarker" refers to a gene, or a fragment of a gene, the change in amount and/or the detection of which can be correlated with a particular physical condition or state. Particular marker genes used in the present invention are correlated with the risk of miscarriage or embryo implantation failure, and are also used in the methods described herein. The detection and/or quantification of such marker genes may be achieved by any means and is not limited to detection/quantification of nucleic acids. Marker genes may also be detected via their respective expression products, including the expressed peptides, polypeptides, and proteins, and fragments thereof.

As used herein, the term "amount" or "level" as used herein refers to a quantity of a marker gene or its expression product that is detectable or measurable in a biological sample and/or control or reference sample. The quantity of a marker gene can be, for example, a quantity of nucleic acid or protein. The term can alternatively include combinations thereof. The amount or level of the marker genes may refer to the absolute amount or level of the biomarkers. Alternatively, a change in the relative level or amount of marker(s) may be assessed by comparing the level or amount of the marker genes in a sample from the subject with a control value or reference value. Alternatively, the relative amount or level of the marker genes may in some instances refer to the concentration of the markers genes relative to the total amount or level of marker genes in the sample.

The level of marker genes can be detected and/or quantified by detection of nucleic acid, e.g. RNA. For example, levels of mRNA can be measured by reverse transcription quantitative polymerase chain reaction (RT-PCR followed with qPCR). RT-PCR is used to create a cDNA from the mRNA. The cDNA can be used in a qPCR assay to produce fluorescence as the DNA amplification process progresses. By comparison to a standard curve, qPCR can produce an absolute measurement such as number of copies of mRNA per cell. Northern blots, microarrays, Invader assays, and RT-PCR combined with capillary electrophoresis may be used to measure expression levels of mRNA in a sample.

In some embodiments, nucleic acid amplification methods can be used to detect a polynucleotide biomarker. For example, oligonucleotide primers and probes can be used in amplification and detection methods that use nucleic acid substrates isolated by any of a variety of well-known and established methodologies. Methods for amplifying nucleic acids include, but are not limited to, for example the polymerase chain reaction (PCR) and reverse transcription PCR (RT-PCR), ligase chain reaction (LCR), strand displacement amplification (SDA), thermophilic SDA (tSDA), Tagman-PCR, multiplex Tagman-PCR, Nanostring, targeted sequencing, digital PCR or any suitable method known in the art.

The detection and quantification of marker genes in the methods of the invention may also involve the use of an agent wherein the agent specifically detects expression products of the marker genes, e.g. proteins or peptides of interest. The agent could be an antibody or functional equivalent thereof that binds proteins or peptides under analysis (i.e. anti-peptide antibody). These antibodies may be used to perform an immunoassay such as, but not limited to, enzyme linked immunosorbent assay (ELISA), radio-immunoassay, immunoprecipitation, immunohistochemistry, immunofluorescence, protein dot blot, Western blot, turbidimetry, nephelometry, FACS and the like, which are known to the skilled person.

The relative abundances of the marker genes for decidual cells and decidual senescent cells may be expressed as a ratio, e.g. a SCARA5/DIO2 ratio. The fold-change in this ratio provides information regarding the respective levels of these marker genes and may be used in the methods described herein. An increase in the level of marker genes for decidual cells, and optionally also a decrease in the level of marker genes for decidual senescent cells, would lead to an increased ratio. A decrease in the level of marker genes for decidual cells, and optionally also an increase in the level of marker genes for decidual senescent cells, would lead to a decreased ratio.

Method of Monitoring or Evaluating the Effect of a Treatment

The invention further provides a method for monitoring or evaluating the effect of a treatment to reduce the risk (or likelihood or probability) of miscarriage or embryo implantation failure in an individual, wherein the method comprises detecting and/or quantifying the amount of at least one marker gene for decidual cells and at least one marker gene for decidual senescent cells in a biological sample obtained from the individual, and thereby monitoring or evaluating the effect of the treatment. The relationship between the level of marker genes for decidual cells and decidual senescent cells enables the risk of miscarriage or implantation failure to be determined, as described in the preceding section, and thereby allows the determination of whether a treatment is effective in reducing risk. The treatment that may be used to reduce the risk is described further below.

The marker genes and sample that can be used in the method of monitoring or evaluating the effect of treatment may be any as described for use in the preceding sections.

Monitoring or evaluating the effect of treatment to reduce the risk of miscarriage or embryo implantation failure includes determining whether the individual is responding or has responded to the treatment, determining the nature of the response, determining the extent of the response, and determining whether or not the individual continues to respond to the treatment in the same way over time. In some cases the individual is determined to be responsive to the treatment or to have had a positive response. Responsiveness or a positive response to treatment means that the individual is expected to derive benefit, or a sufficient extent of benefit, as a result of the treatment. For example, the individual may have or be expected to successfully conceive, or the individual may have an improved prognosis. Non-responsiveness or a negative response to treatment means that the individual is not expected to derive benefit, or a sufficient extent of benefit, from receiving the treatment.

An increased or increasing level of a marker gene for decidual cells e.g. SCARA5 in a sample, as compared with a reference sample or level, may indicate a positive response to treatment. Alternatively, a decreased or decreasing level of a marker gene for decidual senescent cells e.g. DIO2, as compared with a reference sample or level, may indicate a positive response to treatment. In one instance, an increased or increasing level of a marker gene for decidual cells e.g. SCARA5 in a sample and a decreased or decreasing level of a marker gene for decidual senescent cells e.g. DIO2, as compared with a reference sample or level, together may indicate a positive response to treatment. The relative abundances of the marker genes for decidual cells and decidual senescent cells may be expressed as a ratio, e.g. a SCARA5/DIO2 ratio. The fold-change in this ratio may indicate whether treatment is effective. For instance, an increase in the level of marker genes for decidual cells, and optionally also a decrease in the level of marker genes for decidual senescent cells, would lead to an increased ratio, indicating a positive response to treatment by attenuation of decidual senescence.

A decreased or decreasing or unchanged level of a marker gene for decidual cells e.g. SCARA5 in a sample, as compared with a reference sample or level, may indicate a negative response to treatment. Alternatively, an increased or increasing or unchanged level of the marker gene for decidual senescent cells e.g. DIO2, as compared with a reference sample or level, may indicate a negative response to treatment. In one instance, decreased or decreasing or unchanged level of the marker gene for decidual cells e.g. SCARA5 in a sample, and an increased or increasing or unchanged level of the marker gene for decidual senescent cells e.g. DIO2, as compared with a reference sample or level, together may indicate a negative response to treatment. There may be a decrease in the ratio of marker genes for decidual cells to decidual senescent cells caused by a decrease in the level of marker genes for decidual cells, and optionally also an increase in the level of marker genes for decidual senescent cells, indicating a negative response to treatment.

In one instance, the method for monitoring or evaluating the effect of a treatment to reduce the risk of miscarriage or embryo implantation failure in an individual further comprises detecting and/or quantifying the level of uNK cells or the level of at least one marker gene for uNK cells in the sample. The detection and/or quantification of the level of uNK cells, for example based on marker genes may be as described in the preceding sections.

An increased or increasing level of the uNK cells or uNK cell gene markers in a sample, as compared with a reference sample, may indicate a positive response to treatment. A decreased or decreasing level of uNK cells or uNK cell gene markers, as compared with a reference sample, may indicate a negative response to treatment.

The above method of treatment of the invention may also further comprise detecting and/or quantifying genes that allow identification of the stage, point or day in the menstrual cycle as described in the preceding sections.

The control sample or reference sample or level may be selected according to any of the criteria described above. In the method of monitoring or evaluating the effect of a treatment to reduce the risk of miscarriage or embryo implantation failure in an individual, the level of the marker genes (e.g. SCARA5 and DIO2) at a first time point before the treatment may be compared with the level of the marker genes (e.g. SCARA5 and DIO2) at a later time point during or after the treatment. The level of the marker genes (e.g.

SCARA5 and DIO2) during treatment may also be compared with the level of marker genes (e.g. SCARA5 and DIO2) at a later time point during or after the treatment. In some instances, the level of marker genes may be determined monthly, bi-monthly, every three months, every four months, every five, every six months, every seven months, every eight months, every nine months, every ten months, every eleven months, every twelve months, or at any other suitable time interval as determined by a medical practitioner.

In a related aspect to the above method, the invention also provides a method of preventing or reducing the risk of miscarriage or implantation failure in an individual, comprises detecting and/or quantifying the amount of at least one marker gene for decidual cells and at least one marker gene for decidual senescent cells in a biological sample obtained from the individual, and administering an agent or carrying out a treatment regimen effective to prevent or reduce the risk of miscarriage or implantation failure in the individual. The agent is administered or the treatment regimen carried out if the marker gene levels are indicative of a risk of miscarriage or implantation failure as described above.

Method of Diagnosing a Reproductive Disorder

The invention additionally provides a method of diagnosing a reproductive disorder in an individual, wherein the method comprises detecting and/or quantifying the amount of at least one marker gene for decidual cells and at least one marker gene for decidual senescent cells in a biological sample obtained from the individual, and thereby diagnosing the disorder. The marker genes that can be used in the method of diagnosing a reproductive disorder are as described in the preceding sections.

The reproductive disorder may be any reproductive disorder. The reproductive disorder may be any disorder associated with infertility, miscarriage, associated with the risk of obstetric complications or having a negative impact on pregnancy outcome. The reproductive disorder described herein may be any disorder comprising reduced receptivity or failure of the endometrium to be receptive an embryo. Such disorders may include embryo implantation failure, miscarriage, recurrent pregnancy loss or placental disorders Diagnosis includes determining whether or not the individual has a reproductive disorder. Diagnosis may also include determining the particular cause of the reproductive disorder, and determining the different clinical presentations. A positive diagnosis relates to the determination that an individual has the disorder. A negative diagnosis relates to the determination that an individual does not have the disorder.

A decreased or decreasing level of a marker gene for decidual cells e.g. SCARA5 in a sample, as compared with a reference sample or level, may indicate a positive diagnosis. Alternatively, an increased or increasing level of the marker genes for decidual senescent cells e.g. DIO2, as compared with a reference sample or level, may indicate a positive diagnosis. In one instance, a decreased or decreasing level of the marker gene for decidual cells e.g. SCARA5 in a sample and an increased or increasing level of the marker gene for decidual senescent cells e.g. DIO2, as compared with a reference sample or level, together may indicate a positive diagnosis.

An unchanged (or similar), increased or increasing level of the marker gene for decidual cells e.g. SCARA5 in a sample, as compared with a reference sample or level, may indicate a negative diagnosis. Alternatively, an unchanged (or similar), decreased or decreasing level of the marker gene for decidual senescent cells e.g. DIO2, as compared with a reference sample or level, may indicate a negative diagnosis. In one instance, an unchanged (or similar), increased or increasing level of the marker gene for decidual cells e.g. SCARA5 in a sample, and an unchanged (or similar), decreased or decreasing level of the marker gene for decidual senescent cells e.g. DIO2, as compared with a reference sample or level, together may indicate a negative diagnosis.

In one instance, the method of diagnosing a reproductive disorder in an individual further comprises detecting and/or quantifying the level of uterine natural killer (uNK) cells for example based on the level of at least one marker gene for uNK cells in the sample. The uNK cell marker genes that may be used in the method of diagnosis may be as described in the preceding sections.

A decreased or decreasing level of the uNK cells in a sample, as compared with a reference sample, indicates a positive diagnosis. An unchanged (or similar), increased or increasing level of uNK cells, as compared with a reference sample, indicates a negative diagnosis.

The method of diagnosis of the invention may also further comprise detecting and/or quantifying genes that allow identification of the day in the menstrual cycle as described in the preceding sections.

A control sample or reference sample or level may be provided according to the criteria described above, and may represent a level from an individual or multiple individuals known to have a reproductive disorder, or known to not have any reproductive disorder.

Methods of Therapy

In accordance with the invention, a method of treating a reproductive disorder in an individual is also provided. The method comprises diagnosing the reproductive disorder according to the method described in the preceding sections and administering an agent or carrying out a treatment regimen effective to treat the reproductive disorder in the individual who is positively diagnosed. Also described is an agent for use in a method of treating a reproductive disorder in an individual, wherein the reproductive disorder is diagnosed according to the methods described in the preceding sections. Also described is the use of an agent for the preparation of a medicament for the treatment of a reproductive disorder. In some embodiments, the individual has an increased level of at least one marker gene for decidual senescent cells e.g. DIO2. In some embodiments, the individual has a decreased level of at least one marker gene for decidual cells, e.g. SCARA5. The term "treating" includes a reduction or prevention of the development or progression of the disorder, and the reduction or elimination of an existing disorder or its symptoms. For instance, an individual may be considered treated if the marker levels are altered such that a negative diagnosis may be made. For instance, the relative abundances of the marker genes for decidual cells and decidual senescent cells may be expressed as a ratio, e.g. a SCARA5/DIO2 ratio. The fold-change in this ratio may indicate whether treatment is effective. For instance, an increase in the level of marker genes for decidual cells, and optionally also a decrease in the level of marker genes for decidual senescent cells, would lead to an increased ratio, indicating a positive response to treatment by attenuation of decidual senescence. There may also be a decrease in the ratio of marker genes for decidual cells to decidual senescent cells caused by a decrease in the level of marker genes for decidual cells, and optionally also an increase in the level of marker genes for decidual senescent cells, indicating a negative response to treatment.

Agents or treatment regimens that may be administered or carried out may be any agent or treatment regimen known to be effective to treat a reproductive disorder. The agent or treatment regimen may be any able to increase the level of decidual cells and/or uNK cells, and/or decrease the level of decidual senescent cells in the individual. Suitable agents or treatment regimens may include but are not limited to endometrial scratching, dipeptidyl-peptidase IV (DPP4) inhibitors (typically gliptins, e.g. sitagliptin), and senolytic drugs (e.g. dasatinib, quercetin). Examples of DPP4 inhibitors include for instance, vildagliptin, saxagliptin, alogliptin, linagliptin, gemigliptin, evogliptin, omarigliptin, teneligliptin, and are described for example in Deacon C F & Lebovitz H E, Diabetes Obes Metab., 2016; 18(4):333-47. The agent or treatment regimen may target different types of decidual dyshomeostasis, as determined based on the methods of diagnosis previously described. For instance, endometrial scratching may be used to treat decidual failure. Senolytic drugs may be used to treat age-related reproductive disorders. Senolytic drugs or senolytics are drugs that are able to target cellular senescence in order to delay, prevent, alleviate or reverse age-related disorders. The above agents and treatment regimens are also described for use in the methods of reducing the risk of or preventing miscarriage or embryo implantation failure described above.

In a preferred aspect, the agent is a DPP4 inhibitor or antagonist. DPP4 is a known marker of glandular differentiation during the midluteal phase of the cycle and is a ubiquitous aminopeptidase expressed both as a cell surface-bound protein and in soluble form (59, 60). DPP4 is also a widely used endometrial receptivity marker gene (61). Stromal cell-derived factor-1α (SDF-1), also known as C-X-C motif chemokine ligand 12 (CXCL12), is a potent chemotactic factor that mediates mobilization of BMDC and homing to the endometrium in response to tissue injury and rising oestradiol levels (62, 63). However, SDF-1 is proteolytically inactivated by DPP4. The inventors have identified that DPP4 inhibitors (gliptins), which are commonly used oral antidiabetic drugs for the treatment of type 2 diabetes (64), may be used to reduce excessive decidual senescence in RPL patients by increasing endometrial stem cells or inhibiting the expression of marker genes for senescent decidual cells e.g. DIO2.

DPP4 inhibitors or antagonists may be any agent that inhibits or antagonises DPP4 expression or activity by any means. The agent may inhibit or antagonise inactivation of SDF-1 by DPP4. Such an agent may be a small molecule, a peptide, a protein, an antibody, a polynucleotide, an oligonucleotide, an antisense RNA, small interfering RNA (siRNA) or small hairpin RNA (shRNA) or any other suitable inhibitor that achieves the function described above. The agent may be a polynucleotide encoding a molecule inhibiting or antagonising DPP4 or may be a polynucleotide, oligonucleotide, antisense RNA, siRNA or shRNA inhibiting expression of DPP4, typically comprising a complementary sequence to DPP4 mRNA and specifically hybridising thereto. An oligonucleotide "specifically hybridises" to a target sequence when it hybridises with preferential or high affinity to the target sequence but does not substantially hybridise, does not hybridise or hybridises with only low affinity to other sequences. More preferably, the oligonucleotide hybridises to the target sequence with a $T_m$ that is at least 5° C., at least at least 10° C., at least 20° C., at least 30° C. or at least 40° C., greater than its $T_m$ for other nucleic acids. Conditions that permit the hybridisation are well-known in the art (for example, Sambrook et al., 2001, Molecular Cloning: a laboratory manual, 3rd edition, Cold Spring Harbour Laboratory Press; and Current Protocols in Molecular Biology, Chapter 2, Ausubel et al., Eds., Greene Publishing and Wiley-Interscience, New York (1995)). The hybridisation conditions may be stringent conditions as described in the art.

The agent may be an antibody that specifically binds to DPP4 protein or to another protein to inhibit DPP4 function indirectly. An antibody "specifically binds" to a protein when it binds with preferential or high affinity to that protein but does not substantially bind, does not bind or binds with only low affinity to other proteins. For instance, an antibody "specifically binds" a target molecule when it binds with preferential or high affinity to that target but does not substantially bind, does not bind or binds with only low affinity to other human proteins.

An antibody binds with preferential or high affinity if it binds with a Kd of $1\times10^{-7}$ M or less, more preferably $5\times10^{-8}$ M or less, more preferably $1\times10^{-8}$ M or less or more preferably $5\times10^{-9}$ M or less. An antibody binds with low affinity if it binds with a Kd of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

The antibody may be, for example, a monoclonal antibody, a polyclonal antibody, a single chain antibody, a chimeric antibody, a bispecific antibody, a CDR-grafted antibody or a humanized antibody. The antibody may be an intact immunoglobulin molecule or a fragment thereof such as a Fab, $F(ab')_2$ or Fv fragment.

In a preferred embodiment, the agent used in the method of treatment may be a gliptin, for example including sitagliptin, vildagliptin, saxagliptin, linagliptin, gemigliptin, anagliptin, teneligliptin, alogliptin, trelagliptin, omarigliptin, evogliptin, gosogliptin, or dutogliptin. Preferably, the gliptin is sitagliptin.

In some embodiments, the treatment may include a step of detecting an increased level of a marker gene for decidual senescent cells (e.g. DIO2). Where increased DIO2 is detected, the agent used is preferably a DPP4 inhibitor, typically a gliptin and more preferably sitagliptin.

Specific routes, dosages and methods of administration of the therapeutic agents described herein may be routinely determined by the medical practitioner. The agents used in the methods of treatment described herein may be formulated in pharmaceutical compositions. These compositions may comprise, in addition to the therapeutically active ingredient(s), a pharmaceutically acceptable excipient, carrier, diluent, buffer, stabilise or other materials well known to those skilled in the art. Such materials should be non-toxic and should not interfere with the efficacy of the active ingredient. The pharmaceutical carrier or diluent may be, for example, an isotonic solution.

The dose may be determined according to various parameters, especially according to the agent used; the age, weight and condition of the patient to be treated; the route of administration; and the required regimen. Again, a physician will be able to determine the required route of administration and dosage for any particular patient.

The agent can be administered to the patient by any suitable means. The agent can be administered by enteral or parenteral routes such as via oral, buccal, anal, pulmonary, intravenous, intra-arterial, intramuscular, intraosseous, intraperitoneal, intraarticular, topical or other appropriate administration routes. For example, where the agent is a DPP4 inhibitor e.g. sitagliptin, it is preferably administered orally.

A daily dosage for administration of a gliptin such as sitagliptin to a subject such as a human may range from about 50 mg/day to about 2000 mg/day, such as from about 50 mg/day to about 1500 mg/day, from about 50 mg/day to about 100 mg/day, from about 75 mg/day to about 150 mg/day, from about 100 mg/day to about 1500 mg/day, from about 100 mg/day to about 1200 mg/day, from about 100 mg/day to about 175 mg/day, from about 150 mg/day to about 300 mg/day, from about 200 mg/day to about 350 mg/day, from about 250 mg/day to about 400 mg/day, from about 300 mg/day to about 450 mg/day, from about 350 mg/day to about 500 mg/day, from about 400 mg/day to about 550 mg/day, from about 450 mg/day to about 600 mg/day, from about 500 mg/day to about 750 mg/day, from about 600 mg/day to about 800 mg/day, from about 700 mg/day to about 1000 mg/day, or from about 800 mg/day to about 1200 mg/day. Preferably, a typical daily dose of sitagliptin is about 100 mg/day or at least about 100 mg/day.

Administration may be in single or multiple doses. Multiple doses may be administered via the same or different routes and to the same or different locations. Alternatively, doses can be via a sustained release formulation, in which case less frequent administration is required. Dosage and frequency may vary depending on the half-life of the agent in the patient and the duration of treatment desired. The dosage as described above may be administered once a day, or may be divided into two doses. The agent may be administered for more than one, for example, at least two or at least three consecutive menstrual cycles. For instance, 100 mg sitagliptin capsules may be taken orally once a day for 2 or 3 consecutive menstrual cycles.

The method of treatment for medical use may comprise administering additional agents known to be effective in treating reproductive disorders to the individual. For instance, progesterone and/or progestogen may be additionally administered.

Also provided herein are methods of preventing miscarriage or embryo implantation failure, comprising detecting and/or quantifying the amount of at least one marker gene for decidual cells and at least one marker gene for decidual senescent cells in a biological sample obtained from an individual, to thereby assess the individual as being at risk of miscarriage or embryo implantation failure, and administering an agent or carrying out a treatment regimen effective to prevent miscarriage or embryo implantation failure. The agent or treatment regimen may be any agent or treatment regimen described above, preferably administration of a gliptin such as sitagliptin.

Also provided are methods for assessing readiness for conception or successful embryo implantation. Such methods also involve detecting and/or quantifying the amount of at least one marker gene for decidual cells and at least one marker gene for decidual senescent cells in a biological sample obtained from the individual, and thereby assessing the readiness for conception or embryo implantation. The marker genes and methods of detection that can be used in the above method are as described in the preceding sections.

Method of Selecting Patients for Treatment

The invention describes a method of selecting patients for treatment to reduce risk (or likelihood or probability) of embryo implantation failure or miscarriage in an individual, wherein the method comprises detecting and/or quantifying the amount of at least one marker gene for decidual cells (e.g. SCARA5) and at least one marker gene for decidual senescent cells (e.g. DIO2) in a biological sample obtained from the individual, and thereby selecting the patients for treatment to reduce the risk of miscarriage or embryo implantation failure based on the level of the marker genes. The method may include detecting and/or quantifying the level of uNK cells in the sample or uNK cell gene markers in a sample. The marker genes that can be used in the method of selecting patients are as those described in the preceding sections. The treatment may be with any treatment regimen or agent as described above.

An individual in which an increased level of at least one marker gene for decidual senescent cells e.g. DIO2 is detected may be selected as a patient for treatment. An individual in which a decreased level of at least one marker gene for decidual cells e.g. SCARA5 may also be selected as a patient for treatment. The selected patient is preferably treated with a DPP4 inhibitor. Preferably, the marker gene for decidual senescent cells is DIO2 and the selected patient is treated with sitagliptin.

The method of the invention may also further comprise detecting and/or quantifying genes that allow identification of the day in the menstrual cycle as described in the preceding sections.

The relationship between the level of marker genes for decidual cells, decidual senescent cells and uNK cells may enable a particular defect in the decidual pathway to be determined. It can then be determined whether a patient would likely benefit from selection of a particular type of treatment to reduce risk of embryo implantation failure or miscarriage.

Method of Stratifying Patients

The invention further provides a method of stratifying patients into different groups, for instance for clinical studies. The method comprises detecting and/or quantifying the amount of at least one marker gene for decidual cells (e.g. SCARA5) and at least one marker gene for decidual senescent cells (e.g. DIO2) in a biological sample obtained from an individual. The method may include detecting and/or quantifying the level of uNK cells in the sample for example based on the level of uNK cell gene markers in a sample. The marker genes that may be used in the method of stratifying patients may be any as described in the preceding sections.

The method of the invention may also further comprise detecting and/or quantifying genes that allow identification of the day in the menstrual cycle as described in the preceding sections.

The relationship between the level of marker genes for decidual cells, decidual senescent cells and uNK cells may enable the particular defect in the decidual pathway to be determined. Patients having different patterns or levels of these markers can then be grouped accordingly for clinical studies.

Kits

The invention further provides a kit, which may be suitable for use in any method of the invention. The kit may include means (e.g. reagents) for detecting and/or quantifying at least one marker gene for decidual cells (e.g. SCARA5) and at least one marker gene for decidual senescent cells (e.g. DIO2) at a nucleic acid or protein level in a biological sample from an individual. The kit may also comprise means for detecting and/or quantifying the level of uNK cells or uNK cell markers. The marker genes that may be detected using the kit may be any of those described in the preceding sections. The kit may also further comprise means for detecting and/or quantifying genes that allow identification of the day in the menstrual cycle as described in the preceding sections. The only reagents for detecting and/or quantifying marker genes comprised in the kit may be reagents for detection of the marker genes specified above.

The kit may additionally include instructions for use of the kit in accordance with methods of the invention. The kit may also comprise details regarding which individuals the method may be carried out upon. The kit may also be provided with means for obtaining an endometrial biopsy sample. The kit may also comprise a test requisition form with details to be sent to the analysers. The kit may additionally comprise means for the measurement of other laboratory or clinical parameters, and/or a container for holding a biological sample isolated from a subject.

The kit may additionally comprise one or more other reagents or instruments which enable the method to be carried out. Such reagents or instruments may include one or more of the following: suitable buffer(s) (aqueous solutions), calibration curve standards, developing reagents, enzymes, labels, reacting surfaces, means for detection, control samples, standards, instructions, interpretive information, means to isolate a relevant biomarker from a sample, means to obtain a sample from the individual (such as a vessel or an instrument comprising a needle) or a support comprising wells on which quantitative reactions can be done.

In one instance, the kit may comprise a cryotube and RNA stabilizing solution.

In one instance, use of the above test kit for assessing miscarriage or embryo implantation failure, or for diagnosing a reproductive disorder is described. The use may comprise steps as described above in relation to the methods of the invention detecting marker genes.

EXAMPLES

Materials and Methods

Ethical Approval and Sample Collection

The study was approved by the NHS National Research Ethics-Hammersmith and Queen Charlotte's & Chelsea Research Ethics Committee (1997/5065). Endometrial biopsies were obtained from women attending the Implantation Clinic, a dedicated research clinic at University Hospitals Coventry and Warwickshire (UHCW) National Health Service Trust. Timed endometrial biopsies, relative to the preovulatory LH surge, were obtained using a Wallach Endocell™ endometrial sampler with written informed consent and in accordance with The Declaration of Helsinki (2000) guidelines.

Primary Endometrial Stromal Cell (EnSC) Culture

Endometrial biopsies were collected in DMEM-F12 media supplemented with 10% dextran coated charcoal-stripped FBS (DCC) and processed for primary EnSC culture as described (1). For decidualization studies, confluent monolayers of human endometrial stromal cells (EnSCs) were incubated overnight at 37° C. with 5% $CO_2$ in phenol red-free DMEM/F-12 containing 2% DCC, containing antibiotic/antimycotic and L-glutamine (2% media). To induce differentiation, cells were treated in 2% media with 0.5 mM 8-bromo-cAMP (Sigma-Aldrich, Poole, UK) and 1 µM medroxyprogesterone acetate (MPA; Sigma-Aldrich) for the indicated time-points.

Droplet Generation and Single Cell Sequencing (Drop-Seq)

Single-cell transcriptomes were captured in aqueous droplets containing barcoded beads using a microfluidic system (scRNAseq: Dolomite Bio, Royston, UK) according to the manufacturer's protocol and based on the Drop-Seq method described by Macosko and colleagues (2). Briefly, cells in suspension were placed into the remote chamber of the scRNAseq system. Barcoded beads (Barcoded Bead SeqB; Chemgenes Corp., USA) in lysis buffer at a concentration of 280 beads/µl were loaded into the sample loop. Cell and bead solutions were run at a flow rate of 30 µl/min into a fluorophilic glass microfluidic chip with 100 µm etch depth (Single Cell RNA-seq Chip, Dolomite Bio) with droplet generation oil (Bio-Rad Laboratories, UK) at a flow rate of 200 µl/min for 15-18 minutes. Droplets were collected into a 50 ml Falcon tube, quality checked using a C-Chip Fuchs-Rosenthal Haemocytometer (Labtech, Heathfield, UK), and bead doublets counted. Droplet breakage, bead isolation and reverse transcription were performed exactly as described by Macosko and Goldman (Drop-Seq Laboratory Protocol version 3.1, www.mccarrolllab.com/dropseq). All beads from a single run were processed in one batch through Exonuclease I digestion (New England Biolabs UK, Hitchin, UK). PCR was performed on 8000 beads per reaction, with two reactions per sample, to give ~800 single-cell transcriptomes attached to microparticles (STAMPS) per timepoint. PCR conditions were as per Macosko and Goldman. Clean-up with Agencourt AMPure XP beads (Beckman Coulter, High Wycombe, UK) was performed according to standard Illumina RNAseq protocols with a 0.6× beads to sample ratio. cDNA was eluted in 12 µl and quality and size assessed using an Agilent Bioanalyzer High Sensitivity DNA chip. For tagmentation 600 µg cDNA, as determined by Qubit High Sensitivity DNA assay, was processed according to Macosko and Goldman using Illumina Nextera XT DNA Sample Kit and Indexing Kit. Tagmented libraries were cleaned up using AMPure XP beads as before, with a 0.6× beads ratio followed by a repeat clean-up using 1× beads. Eluted libraries were analysed using Agilent Bioanalyzer High Sensitivity DNA chip (Agilent, Stockport, UK) to assess quality and determine library size and concentration was determined by Qubit High Sensitivity DNA assay (ThermoFisher, Paisley, UK). Library dilution and denaturation was performed as per standard Illumina protocols and sequenced using NextSeq High Output 75 cycle V2 kit (Illumina, Cambridge, UK).

Drop-Seq Data Alignment and Quantification

Initial Drop-Seq data processing was performed using Drop-Seq_tools-1.0.1 following the protocol described by Nemesh (seqAlignmentCookbook_v1.2Jan2016.pdf, http://mccarrolllab.com/dropseq). Briefly, reads with low-quality bases in either cell or molecular barcode were filtered and trimmed for contaminating primer or poly-A sequence. Sequencing errors in barcodes were inferred and corrected, as implemented by Drop-Seq_tools-1.0.1. Reads were aligned to the hg19 (Human) reference genome concatenated with ERCC annotations using STAR-2.5.3a (3), with the Gencode21 (Human) as reference transcriptome. Uniquely mapped reads, with ≤1 insertion or deletion, were used in quantification. Finally, the DigitalExpression tool (2) was used to obtain the digital gene expression (DGE) matrix for each sample. Cell numbers were selected computationally from the inflection point in a cumulative distribution of reads plotted against the cell barcodes ordered by descending number of reads. Cell barcodes beyond the inflection point are believed to represent 'ambient RNA' (e.g. contaminating RNA from damaged cells), not cellular transcriptomes, and therefore excluded from further analysis. This resulted in ~800 cells per time-point, matching the number anticipated from processed bead counts. The Drop-Seq data were deposited in the GEO repository (accession number: GSE127918).

Cell Aggregation Analysis

Analysis of DGE data was performed with Seurat v2 (4). To select high-quality data for analysis, cells were included when at least 200 genes were detected, while genes were included if they were detected in at least 3 cells. Cells which had more than 4500 genes were excluded from the analysis as were cells with more than 5% mitochondrial gene transcripts to minimize doublets and low-quality (broken or damaged) cells, respectively. After scaling and normalization of the raw counts in the DGE matrix, cell-cycle regression was applied. For cell aggregation, a set of highly variable genes was first identified, with an average expression mean between 0.0125 and 3 and a Log Variant to Mean Ratio of at least 0.5, which were used to perform principal component (PC) analysis. Judged by their statistical significance and the robustness of the results, the first 10 PCs were subsequently used as inputs for clustering via shared nearest neighbour (SNN) and subsequent t-distributed stochastic neighbour embedding (t-SNE) representation. The Seurat function 'FindAllMarkers' employing the Wilcoxon test was used to identify marker genes for each cell state cluster in the t-SNE representation. To obtain independent estimation of the number of unique cell-types we used SC3 v1.3.18 (5), applying a consensus strategy and Tracy-Widom theory on random matrices to estimate the optimal number of clusters (k).

Co-Regulated Gene Networks

K-means cluster analysis was performed in MeV v4.8 (6) to group marker genes based on co-expression across cell state clusters. Figure of Merit (FoM) was run first to determine the number of expression patterns (k). The predictive power of the k-means algorithm was estimated using a Fig. of merit (FOM) values for k from 1 to 20. K-means clustering was run using Pearson correlation metric for a maximum of 50 iterations. Gene ontology analysis was performed on the clustered genes using DAVID (7).

Trajectory Analysis

Trajectory analysis was performed with Monocle v2.6.1 (8) (9, 10). Branch-point genes were identified with Branched Expression Analysis Modeling (BEAM) function.

Gene Expression Correlation

To test gene expression correlation between pairs of genes, expression was imputed for every cell using Markov Affinity-based Graph Imputation of Cells (MAGIC) (11). Pearson correlation coefficients were calculated for top 50 genes determining the different trajectories at informative branch-points. To assess congruency between the time-course and biopsy datasets, the correlation coefficients added resulting in sum of coefficients between −2 and +2.

Drop-Seq Analysis of Timed Endometrial Biopsies

Seven LH-timed endometrial biopsies were processed as described in detail elsewhere (12); and single-cell fractions subjected to Drop-Seq analysis. The time from biopsy in the clinic to cDNA synthesis was less than 4 hours for all samples. Anonymized endometrial biopsies were obtained from women aged between 31 and 42 years with regular cycles, body mass index between 23 and 32 kg/m$^2$, and absence of uterine pathology on transvaginal ultrasound examination.

Reverse Transcription Quantitative PCR

RNA was extracted from endometrial biopsies which had been snap frozen in clinic (<1 min after collection), using STAT-60 (AMS Biotechnology, Oxford, UK) according to the manufacturer's instructions. Reverse transcription was performed from 1 µg RNA using the Quantitect Reverse Transcription Kit (QIAGEN, Manchester, UK) and cDNA was diluted to 10 ng/µl equivalent before use in qPCR. Amplification was performed on a 7500 Real-Time PCR system (Applied Biosystems, Paisley, UK) in 20 µl reactions using 2×PrecisionPlus Mastermix with SYBR Green and low ROX (PrimerDesign, Southampton, UK), with 300 nM each of forward and reverse primers. L19 was used as a reference control. Primer sequences were as follows: SCARA5 forward 5'-CAT GCG TGG GTT CAA AGG TG-3' (SEQ ID NO: 1) reverse 5'-CCA TTC ACC AGG CGG ATC AT-3' (SEQ ID NO: 2), DIO2 forward 5'-ACT CGG TCA TTC TGC TCA A-3' (SEQ ID NO: 3) reverse 5'-TTC CAG ACG CAG CGC AGT-3' (SEQ ID NO: 4), L19 5'-GCG GAA GGG TAC AGC CAA T-3' (SEQ ID NO: 5) reverse 5'-GCA GCC GGC GCA AA-3' (SEQ ID NO: 6). Relative quantitation was performed using the $2^-ddCt$ with inclusion of an inter-plate calibrator sample. Centile calculations were performed on dCt values using R software.

Uterine Natural Killer (uNK) Cell Isolation

Supernatant from freshly digested EnSC cultures was collected and red blood cells excluded through Ficoll-Paque density gradient centrifugation. uNK cells were isolated by magnetic activated cell separation (MACS; Miltenyi Biotec, Bergisch Gladbach, Germany) using phycoerythrin (PE)-conjugated anti-CD56 antibody (Bio-Legend, San Diego, CA, USA), as per manufacturer's instructions. The CD56+ positive fraction was collected by centrifugation and cultured in suspension for up to 5 days in RPMI media (Sigma-Aldrich) supplemented with 10% DCC-FBS, 1× Antibiotic-Antimycotic, and 2 ng/ml IL-15 (Sigma-Aldrich) to aid uNK cell maturation. To increase yield, uNK harvests from 3-5 patients were pooled. For co-culture experiments, uNK cells were pelleted and re-suspended in 2% media without IL-15 and co-cultured with EnSC monolayers at day 6 of 8-bromo cAMP and MPA treatment. Supernatant was collected every 2 days and centrifuged to clear cell debris prior to storage at −20° C.

Enzyme-Linked Immunosorbent Assay (ELISA)

Cultured EnSC from individual patients were seeded at identical densities and treated in accordance with experimental schedules. Analytes in collected supernatant were analysed by ELISA as per manufacturer's instructions (Duo-Set ELISA kits, Bio-Techne, Abingdon, UK). Standard curves were fitted to a 4-parameter logistic fit curve in GraphPad Prism software and sample concentrations interpolated from these graphs.

Results

Figure 1:
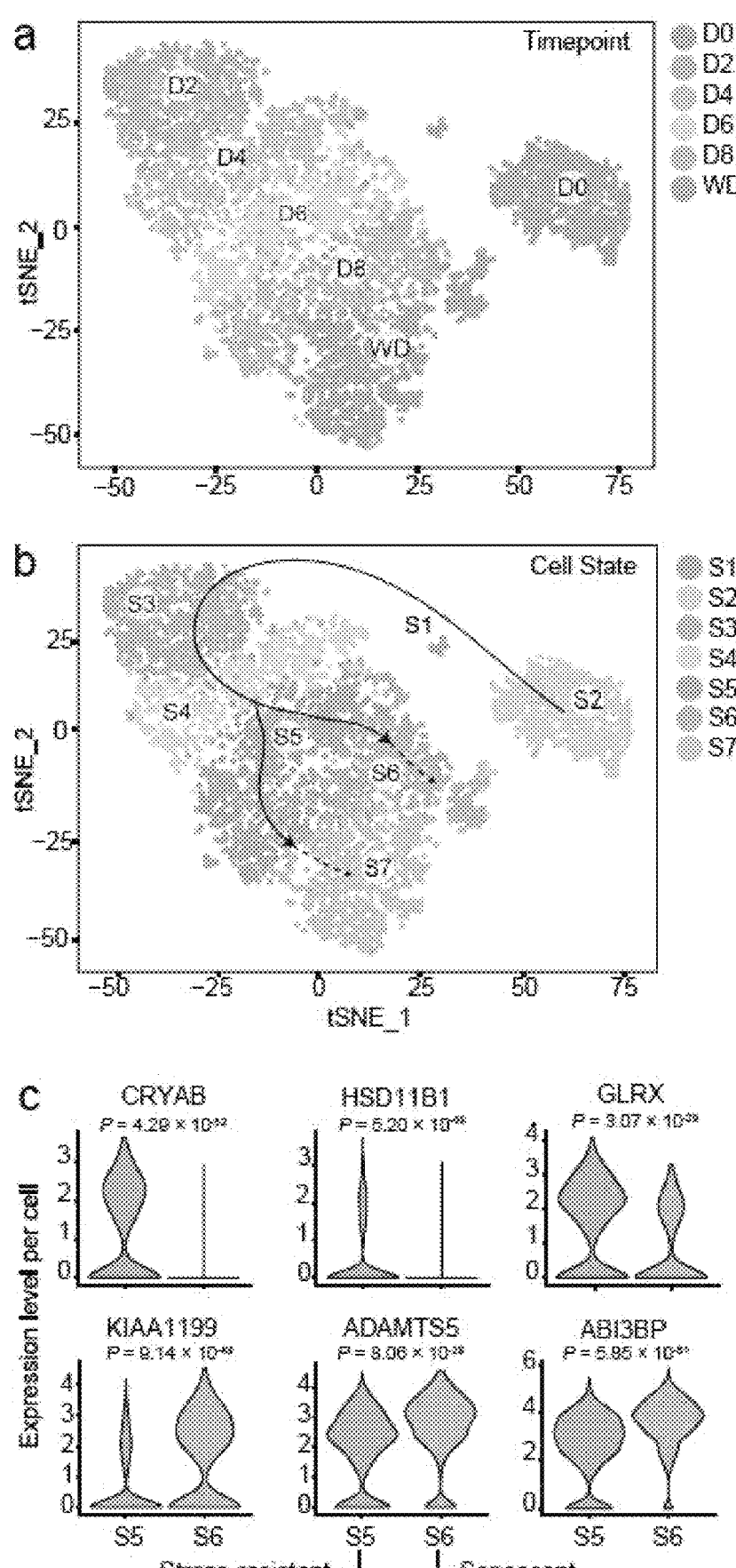
FIG. 1: Single-cell reconstruction of the decidual pathway in culture. (a) t-SNE projection of 4,580 EnSC, annotated according to days of decidualization (D0-8) and upon withdrawal (WD) of the differentiation signal for 48 hours. D0 represents undifferentiated EnSC. (b) The same t-SNE plot now annotated according to transcriptional state (S1-7). (c) Violin plots showing log-transformed, normalized expression levels for indicated genes in stress-resistant decidual cells (S5) and stressed/senescent decidual cells (S6). (d) Decidualizing EnSC were placed in pseudotime to reconstruct the trajectory of differentiation, revealing two branching events along the decidual pathway. (e) Heat map showing gene dynamics during cell state transition at branchpoint 1. Columns are points in pseudotime while rows represent the 50 most dynamic genes at the branch point. The beginning of pseudotime is in the middle of the heat map and the trajectory towards stress-resistant and senescent decidual cells are indicated by the arrows. Hierarchical clustering visualizes modules of genes with similar lineage-dependent expression patterns.
Figure 2:
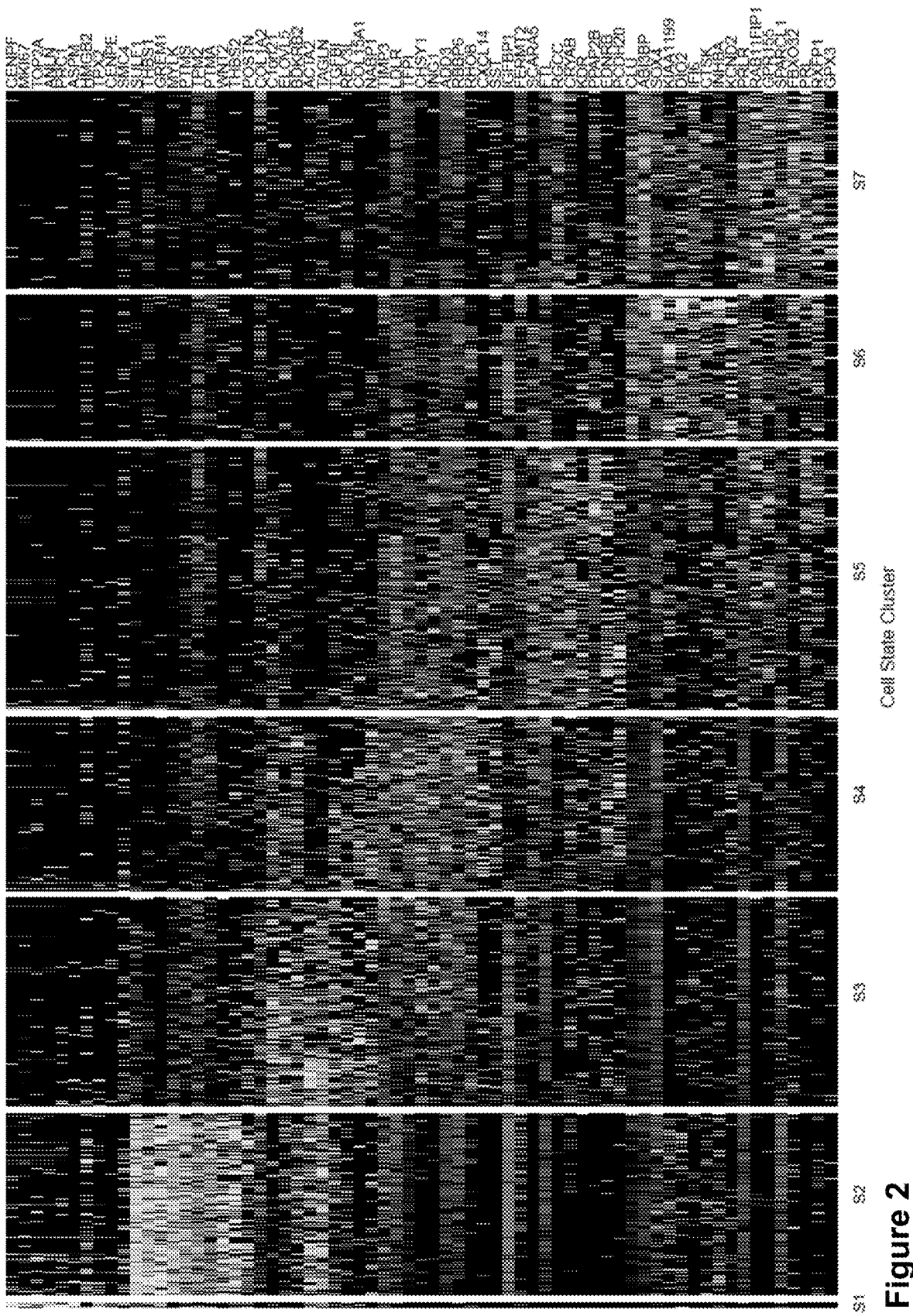
FIG. 2: Heatmap of the top 10 marker genes for each of the 7 cell states. Each column represents one of 4,580 EnSC. Expression for each gene is centered to the average expression across cells and scaled by their standard deviation. The relative level is indicated by the grayscale with white and black representing high and low expression, respectively.

Example 1—Identification of Marker Genes for Risk of Miscarriage or Embryo Implantation Failure and for Reproductive Disorders Single-Cell Analysis of the Decidual Pathway In Vitro We speculated that the risk of miscarriage relates to the incidence of menstrual cycles with aberrant lineage specification of decidual cells. To test this hypothesis, we first reconstructed the decidual pathway in vitro using single-cell transcriptomics to identify marker genes of diverging decidual populations. Primary EnSC were decidualized for 8 days and the differentiation signal was then withdrawn for 2 days, mimicking falling progesterone levels prior to menstruation. Cells were recovered every 48 h and subjected to single-cell analysis using nanoliter droplet barcoding and high-throughput RNA-sequencing[17]. Approximately 800 cells were sequenced per timepoint, yielding on average 1,282 genes per cell. After computational quality control, 4,580 cells were assigned to 7 transcriptional cell states using Shared Nearest Neighbor (SNN) and t-Distributed Stochastic Neighbor Embedding (t-SNE) methods. FIG. 1a shows cells color-coded by day of treatment and FIG. 1b by transcriptional state (S1-7). The top 10 differentially expressed genes (DEG) between cell states are presented as a heatmap (FIG. 2). Apart from a discrete population of proliferative cells (S1), the bulk of undifferentiated EnSC were in S2. By day 2 of decidualization, most cells had transitioned to S3, which differed from S2 by 896 DEG. This precipitous transcriptomic response is in keeping with the discovery that mammalian decidual cells evolved from an ancestral cellular stress response[18,19].

Figure 3:
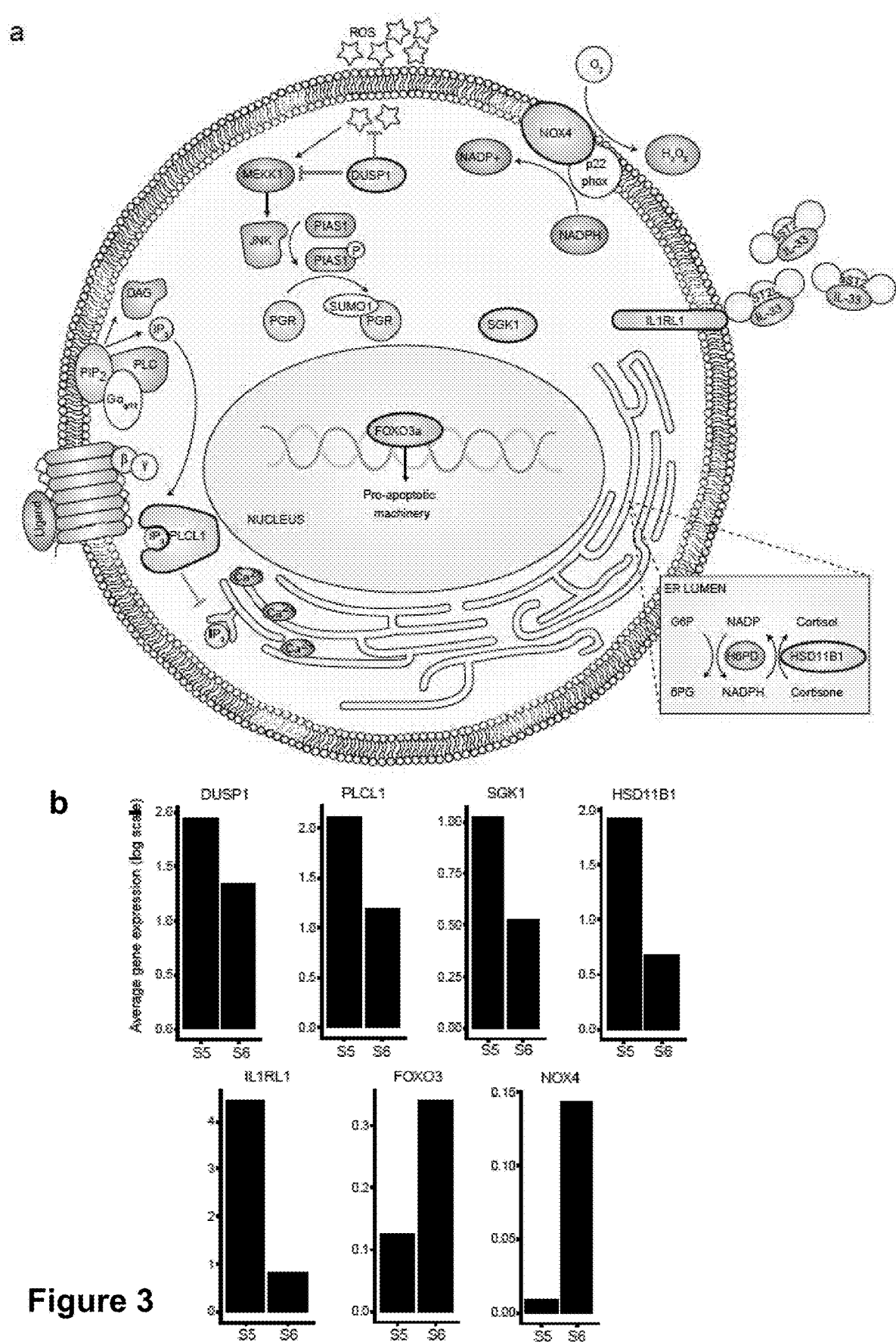
FIG. 3: Mechanisms involved in stress-resistance of decidual cells. (a) Multiple mechanisms underpin stress-resistance of decidual cells, including progesterone-dependent induction of dual specificity phosphatase 1 (DUSP1, also known as mitogen-activated protein (MAP) kinase phosphatase-1), which silences the c-Jun NH-terminal kinase (JNK) stress signaling pathway and blocks stress-dependent sumoylation of numerous targets, including the liganded progesterone receptor (PGR)[48,49]. Progesterone also regulates the expression the serum- and glucocorticoid-inducible kinase SGK1[50], a kinase that targets and inactivates FOXO3, a key transcription factor involved in oxidative cell death responses in endometrial cells[51]. PLCL1, coding phospholipase C like 1 (inactive), is a progesterone-inducible scaffold protein that uncouples phospholipase C activation downstream of Gq-protein-coupled receptors from intracellular Ca2+ release by attenuating inositol trisphosphate (IP3) signaling[52]. Progesterone further upregulates 11β-hydroxysteroid dehydrogenase type 1 (encoded by HSD11B1)[53,20], the enzyme that converts inert cortisone into active cortisol, a powerful anti-inflammatory hormone. A highly-induced decidual gene is IL1RL1, which encodes the IL-33 transmembrane receptor ST2L as well as the secreted decoy receptor sST2[13], a potent anti-inflammatory mediator that binds and inactivates IL-33. The main non-mitochondrial source of reactive oxygen species in endometrial stromal cells is NADPH oxidase NOX49. Although initiation of the decidual process requires NOX4 activation[18], it is also a mediator of cellular senescence[54]. (b) Log-transformed, normalized expression levels indicated genes in stress-resistant decidual cells (S5) and stressed/senescent decidual cells (S6).
Figure 4:
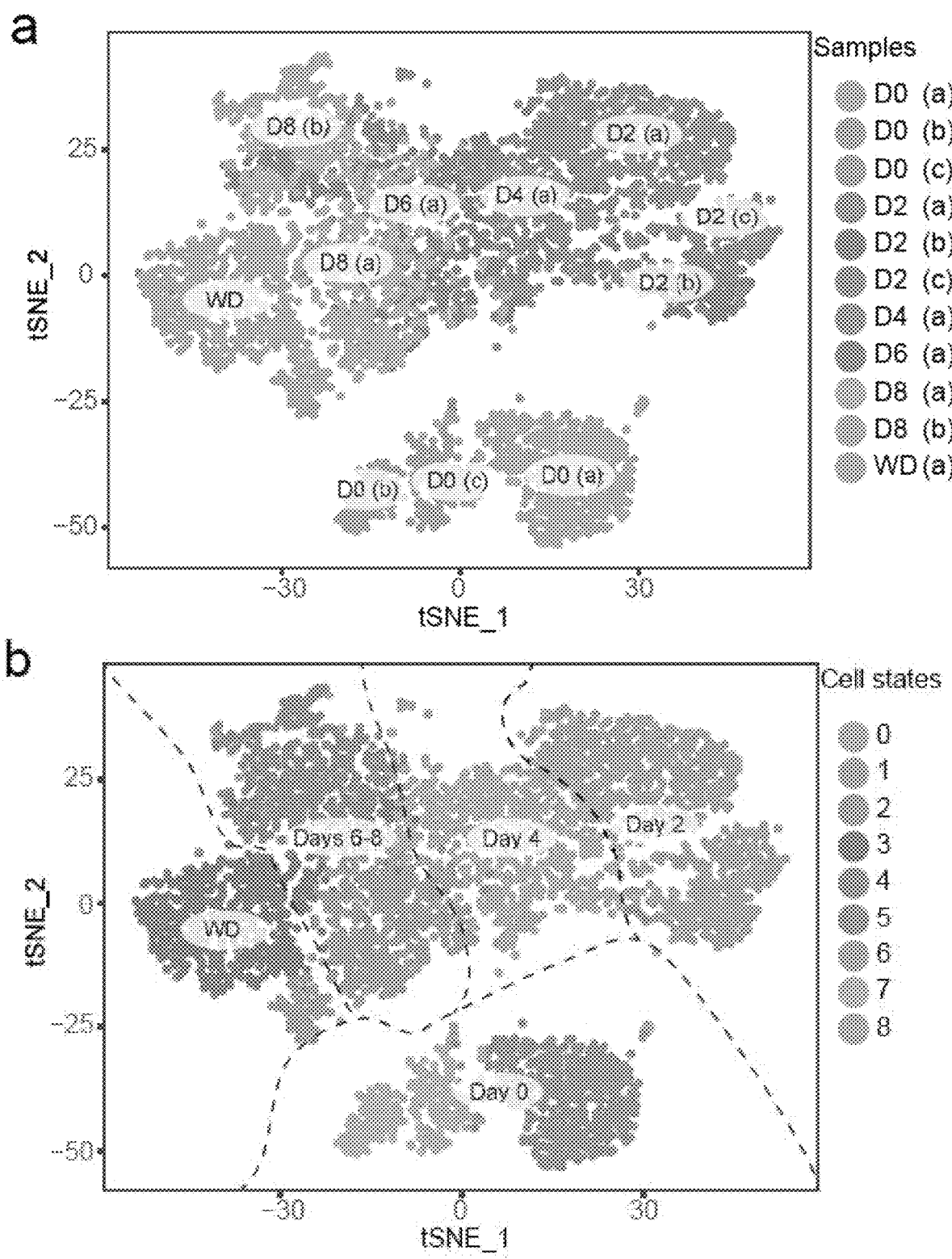
FIG. 4: Single-cell analysis of three independent primary cultures shows cells aggregating by transcriptional state. Three independent primary EnSC cultures (designated a, b, and c) were decidualized for different time-points and then subjected to Drop-seq analysis. Culture 'a' represents the full time-course [D0-D8 plus withdrawal (WD)]; culture 'b' was decidualized for 2 and 8 days whereas culture 'c' was decidualized for 2 days. (A) Different shades of gray in the t-SNE plot mark cells grouped by culture and day of decidualization as indicated. (B) Different shades of gray in the t-SNE plot mark cells grouped by cell state. The plot was annotated to indicate day of decidualization.
Figure 5:
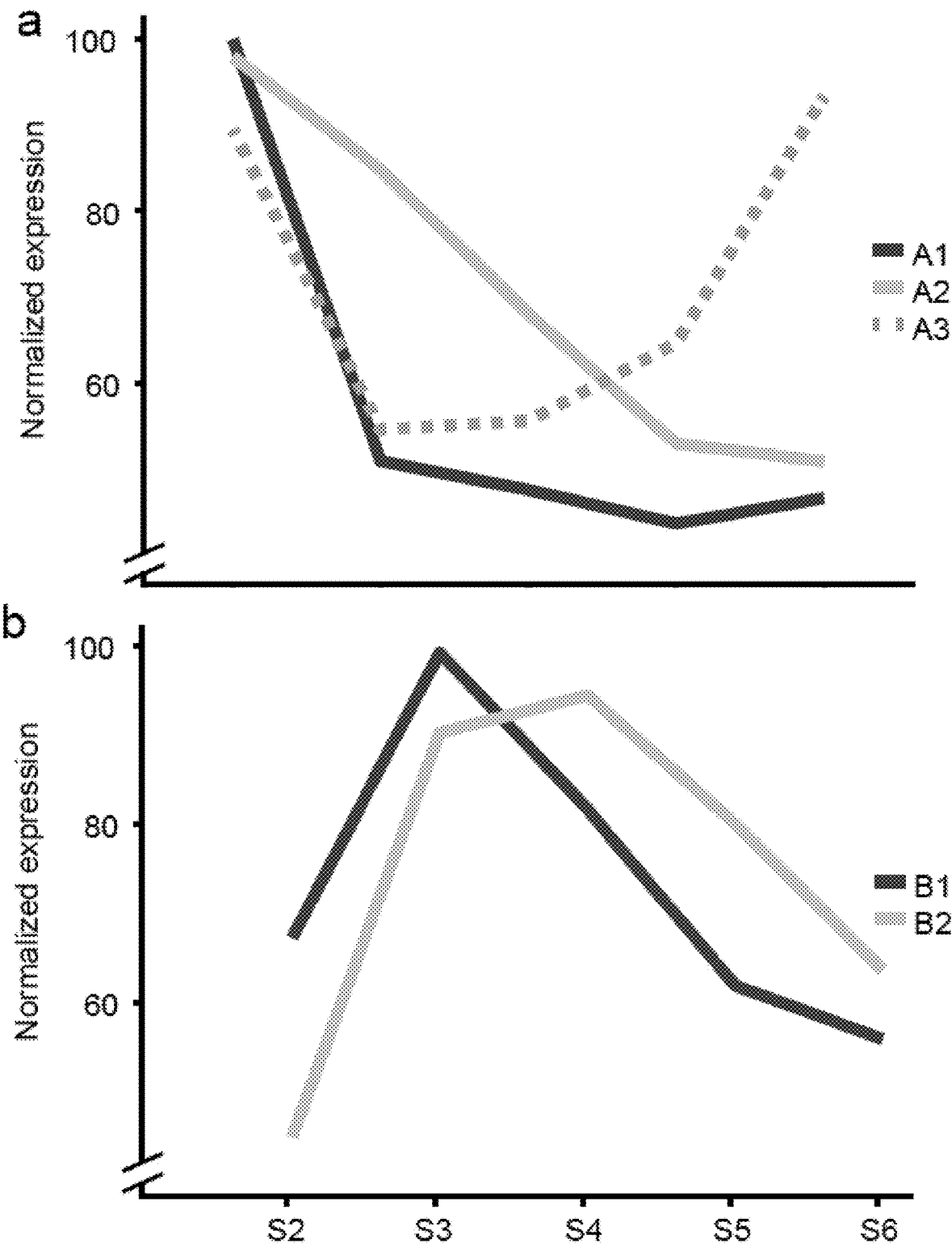
FIG. 5: K-means cluster analysis of co-regulated gene networks. To provide further insight into the genes that drive decidualization (S2 to S6), 1749 genes with variable expression were subjected to K-means cluster analysis (k=7; Table 3). This analysis yielded 7 co-expressed gene networks, which we ordered in 3 main categories (A-C). Line graphs represent the average normalized gene expression in each cell-type (Y-axis) for each of the cell state clusters (X-axis). Category A encompassed 3 gene networks, totaling 867 genes (A1—422 genes; A2—297 genes; A3—148 genes), that were down-regulated during the initial decidual phase (S3 & S4) and either remained repressed or were re-expressed upon the emergence of the two decidual subpopulations (S5 and S6). Gene ontology (GO) analysis revealed that these attenuated networks were significantly enriched in genes involved in translation, mRNA splicing and cell-cell adhesion (D and Table 4). Category B, totaling 460 genes (B1—221 genes; B2—239 genes), denotes gene networks most highly expressed during either the initial decidual phase (S3 and S4), whereas category C networks (421 genes, C1—226 genes; C2—195 genes) are prominent in stress-resistant (S5) and stressed/senescent (S6) decidual cells. Notable GO terms enriched in Category B networks included protein folding and cell redox homeostasis. Further, the gene networks most highly expressed in stressed decidual cells (S6) were signal peptide/secretion and type I interferon signaling pathway (d), hallmarks of cellular senescence[55,56]. Benjamini-adjusted P-values are shown on the X-axis.
Figure 5:
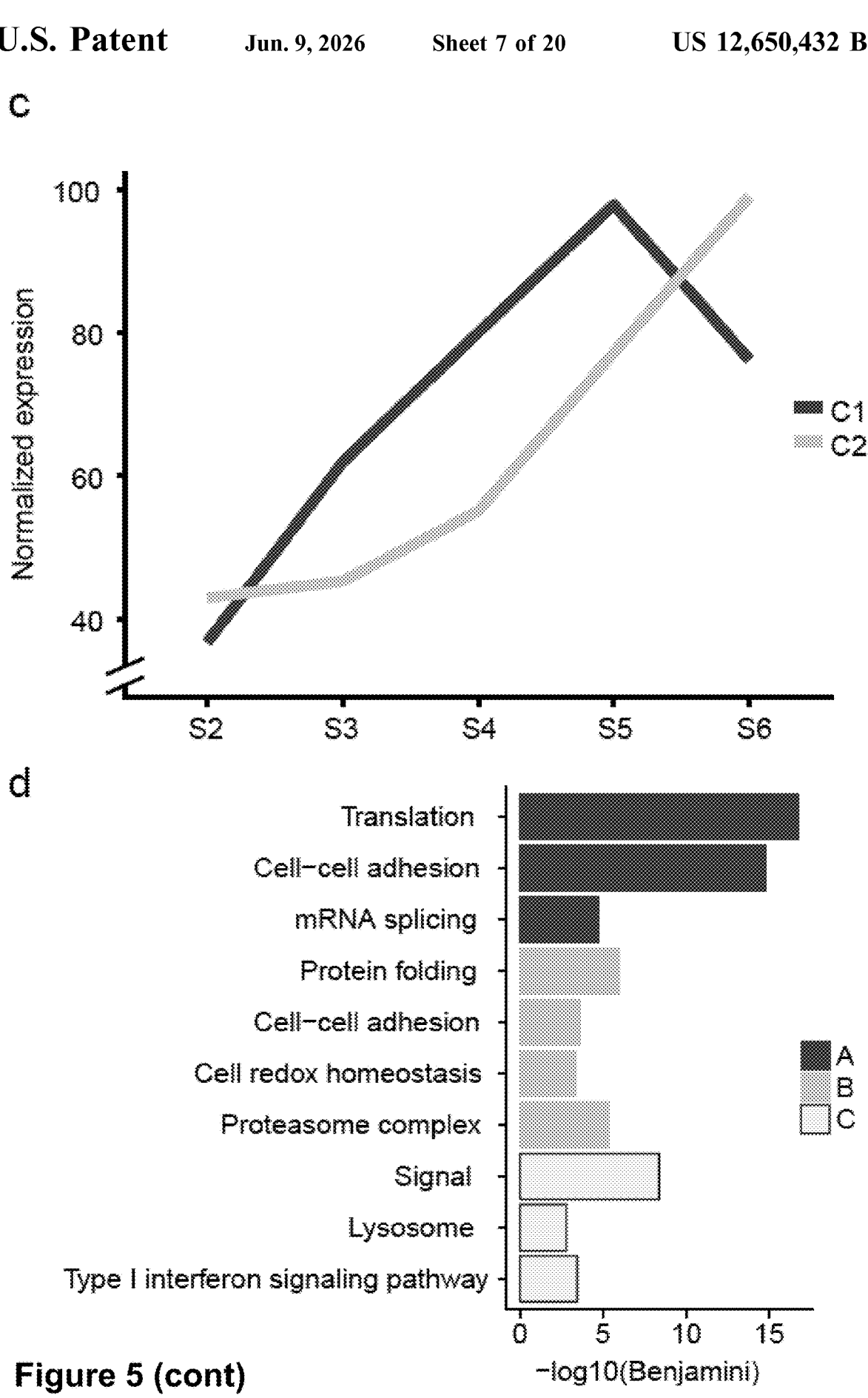

Decidualizing cells progressed in synchrony to S4 by day 4 after which they segregated into two transcriptionally distinct populations, S5 and S6. Known decidual stress defense genes (e.g. CRYAB, HSD11B1, and GLRX)[20-22] were enriched in S5 (designated stress-resistant decidual cells) whereas genes involved in oxidative stress signaling and cellular senescence, including KIAA1199, CLU and ABI3BP[23-26], prevailed in S6 (senescent decidual cells) (FIG. 1c and FIG. 3). Single-cell RNA-seq (scRNA-seq) of independent cultures confirmed polarization of EnSC into divergent decidual subpopulations (FIG. 4). Withdrawal of the decidualization signal on day 8 elicited a further transcriptional change (S7), although some senescent cells appeared refractory. K-means cluster analysis of the 1749 DEG across the decidual pathway revealed 7 co-regulated gene networks (FIG. 5).

Figure 6:
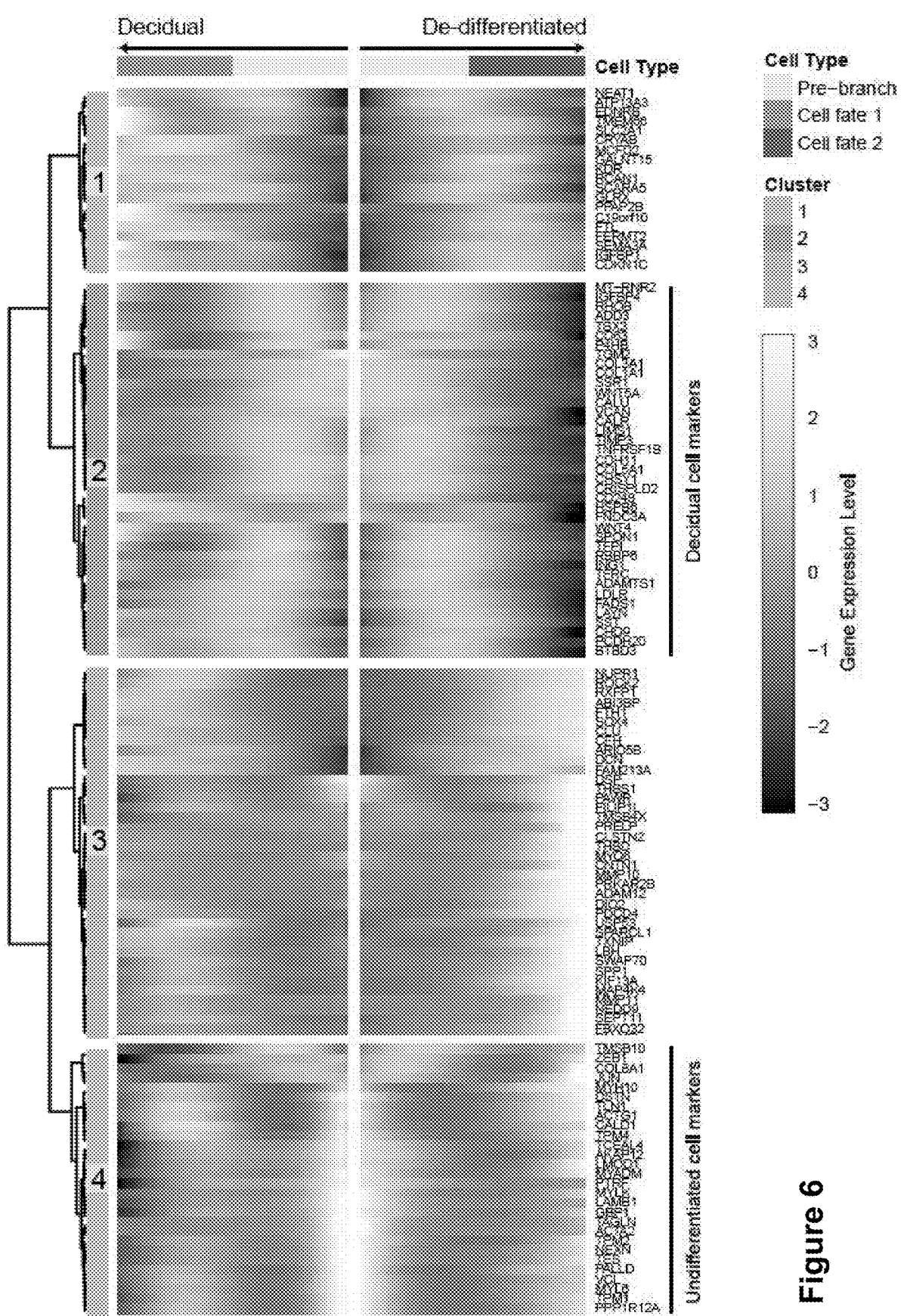
FIG. 6: Heatmap of top 50 genes distinguishing branchpoint 2 in the decidual pathway. Branchpoint 2 is triggered upon withdrawal of the differentiation signal after 8 days of decidualization. Columns are points in pseudotime while rows represent the 50 most dynamic genes at this branchpoint. Hierarchical clustering visualizes modules of genes with similar lineage-dependent expression patterns. The heatmap is annotated to illustrate regulation of prototypic decidual genes and genes highly expressed in undifferentiated EnSC.

Placing decidualizing EnSC in pseudotime confirmed the presence of two branching events across the pathway. Branchpoint 1 signaled divergence into pathways leading to senescent and stress-resistant decidual cells. The top 50 branch-dependent genes are depicted in a modified heatmap, clustered hierarchically to visualize modules of genes with similar lineage-dependent expression patterns (FIG. 1e). DIO2, coding iodothyronine deiodinase 2, was identified as a major branch gene in the senescent pathway. DIO2 catalyzes the conversion of prohormone thyroxine (T4) into bioactive triiodothyronine (T3)[27]. Multiple genes coding secreted senescence factors were co-regulated with DIO2, including CLU (clusterin) and IGFBP1 (insulin-like growth factor-binding protein-, IGFBP-1), a widely used decidual marker gene[14]. FTL and SCARA5, along with known decidual genes such as GLRX and IL1RL1, were part of prominent branching module in stress-resistant decidual cells (FIG. 1d). FTL encodes ferritin light chain (L-ferritin) and SCARA5 (scavenger receptor class A member 5) the L-ferritin receptor, suggesting that iron uptake, storage and detoxification are important for decidual function. Finally, withdrawal of differentiation signals on day 8 of the decidual time-course triggered further cell-fate divergence (branchpoint 2), driven by partial dedifferentiation of decidual cells (FIG. 6).

Secreted Markers of Decidual Subpopulations

Figure 7:
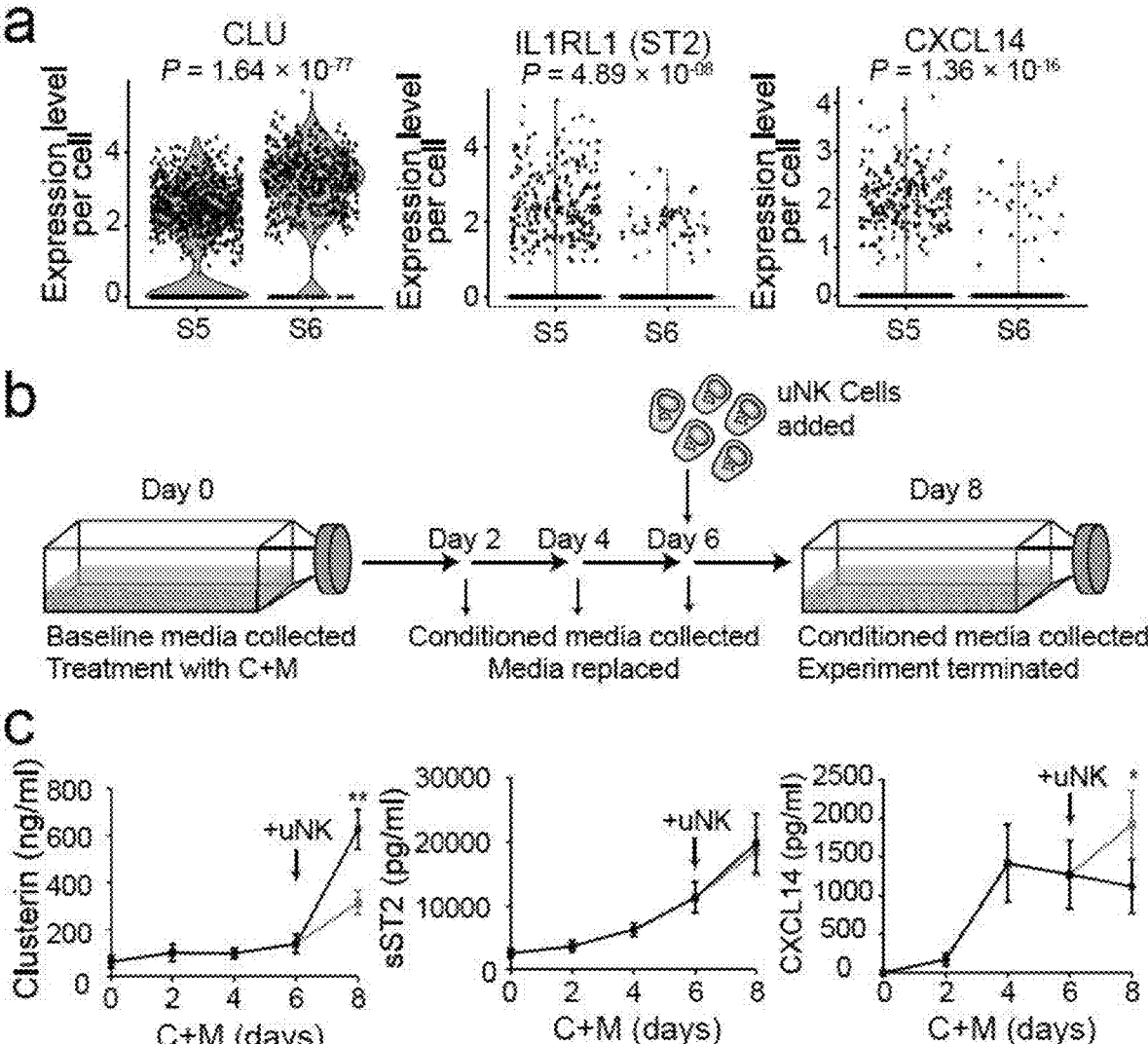
FIG. 7: uNK cells modify the decidual secretome by eliminating senescent decidual cells. (a) Violin plots showing log-transformed, normal expression levels of secreted marker for decidual senescent cells (i.e CLU, clusterin) and decidual cells (i.e. soluble ST2, encoded by IL1RL1, and CXCL14). Decidual senescent cells are denoted as S5 and decidual cells as S6. (b) Four independent primary EnSC cultures were decidualized with 8-bromo-cAMP and MPA (C+M) for the indicated days. The culture medium was refreshed every 48 h. On day 6 of decidualization, 5,000 primary uNK cells per well were added to confluent decidual cells cultured in 6-well plates. (c) The concentrations of CXCL14, sST2 (encoded by IL1RL1) and clusterin were determined in spent medium measured by ELISA. The data show mean±standard deviation of 4 biological repeat experiments. ** indicates P<0.01 (ANOVA).

Our single-cell analysis indicated that senescent and stress-resistant cells contribute specific factors to the decidual secretome (FIG. 7a). To explore this further, four independent primary EnSC cultures were first decidualized for 6 days and then co-cultured for 48 hours with or without uNK cells isolated from luteal phase endometrial biopsies (FIG. 7b). Secreted levels of clusterin, a stress-induced molecular chaperone molecule[26], started to rise sharply on day 6 of the time-course (FIG. 7c), and response markedly blunted upon co-culture with uNK cells (ANOVA, P<0.01). By contrast, co-culturing of uNK cells had no impact on the levels of the soluble IL-33 decoy receptor sST2 (encoded by IL1RL1)[13], produced by stress-resistant decidual cells. Interestingly, although secreted CXCL14 levels plateaued before day 6, uNK cell-mediated clearance of senescent decidual cells further enhanced secretion of this chemokine (P<0.05). Taken together, the data suggest that the decidual micro-environment is determined by the relative abundance of, and crosstalk between, decidual subpopulations; and dynamically modified by uNK cells.

Single-Cell Analysis of Timed Endometrial Biopsies

Figure 8:
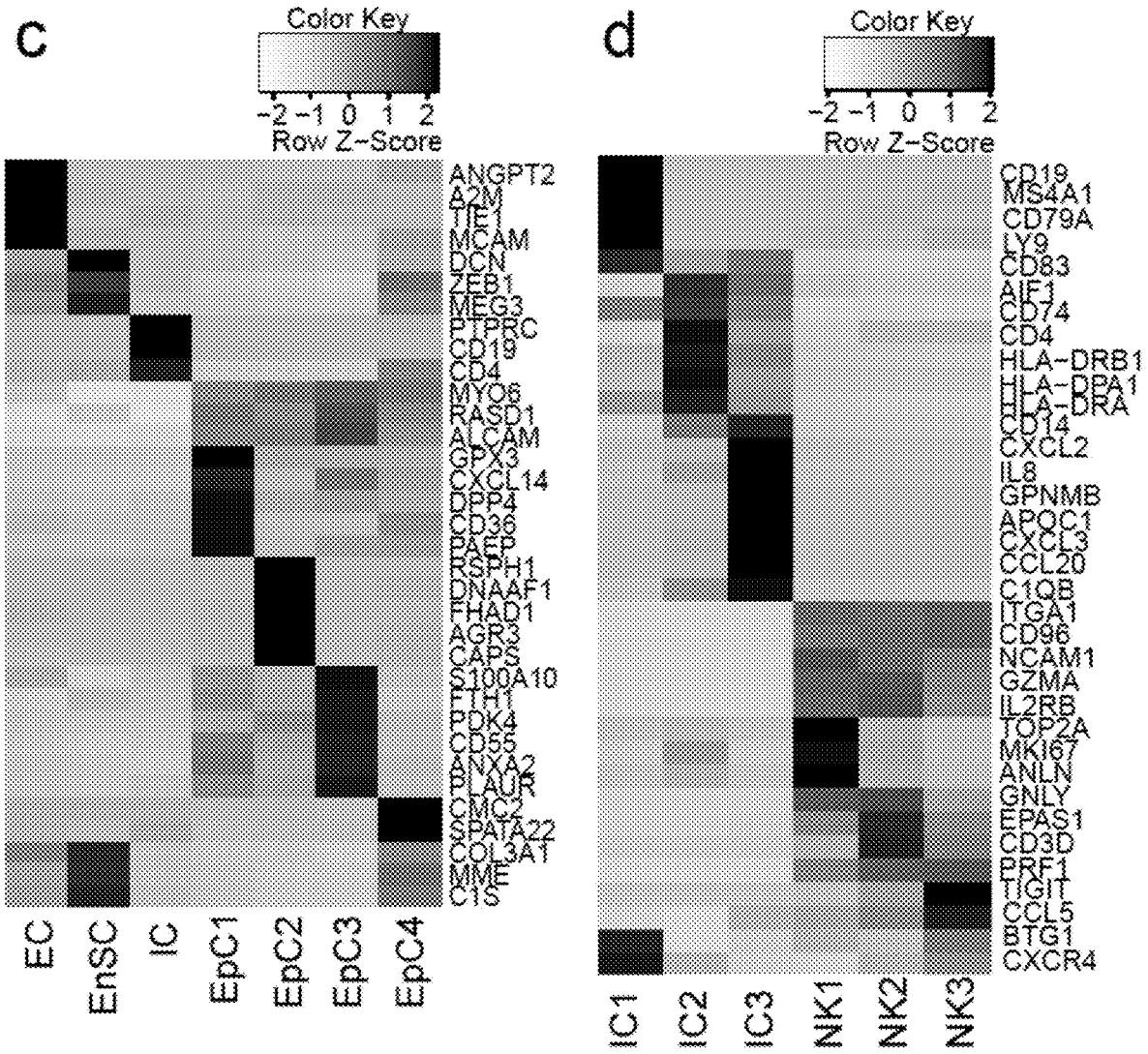
FIG. 8: Identification of endometrial cell types and subsets during the implantation window. (a) t-SNE plot of 3,283 cells isolated from 7 LH-timed biopsies captures all major endometrial cell types, including epithelial cells (EpC), immune cells (IC), endothelial cells (EC), stromal cells (EnSC) and a discrete but transcriptionally distinct proliferative (P) stromal subpopulation. EpC segregated in 4 subpopulations (EpC1-4). (b) Heat map showing relative expression (z-score) of markers defining cell-types and EpC subpopulations. MYO6, RASD1 and ALCAM are included as pan-epithelial genes. (c) Immune cells (IC) were subjected to additional t-SNE analysis, revealing three uNK cell subsets (NK1-3) and naive B-cells (IC1), monocytes (IC2) and macrophage/dendritic cells (IC3). (d) Heat map showing relative expression of markers defining endometrial IC populations during the implantation window, including three uNK cell subsets.
Figure 9:
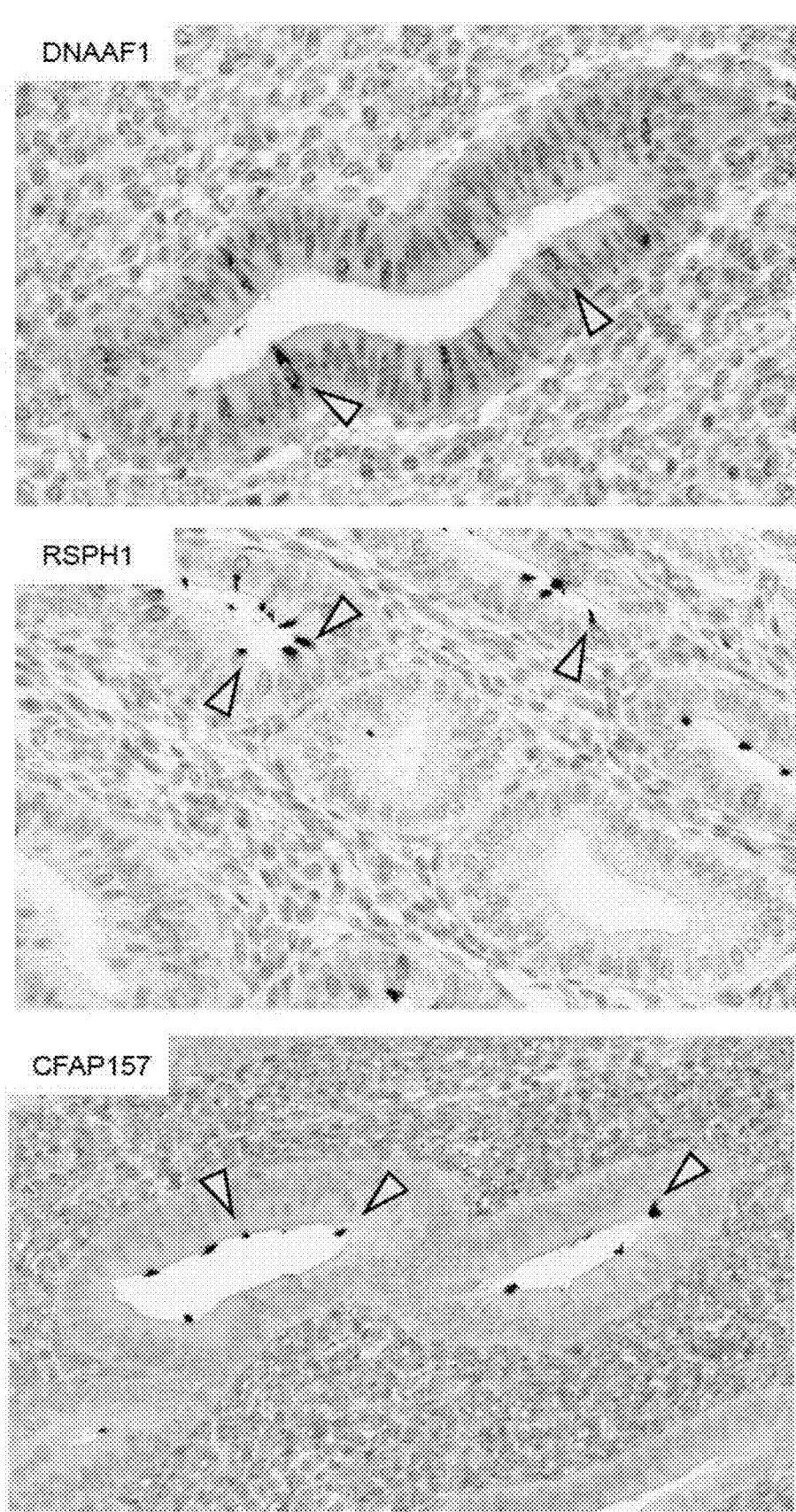
FIG. 9: Distribution of ciliated cells in endometrial glandular epithelium. Arrows indicate the expression of ciliated epithelial markers, DNAAF1, RSPH1 and CFAP157, within the glandular compartment of human endometrium. Images were retrieved from the Human Protein Atlas v18.1 (https://www.proteinatlas.org/)[57].

Next, we performed scRNA-seq on endometrial biopsies to examine lineage specification of decidualizing stromal cells in vivo. Biopsies were timed relative to the pre-ovulatory luteinizing hormone (LH) surge to coincide with the midluteal implantation window (LH+8; n=3) or the start of the refractory late-luteal phase (LH+10; n=4). Following quality control, 3,283 cells were assigned to 5 clusters (FIG. 8a). Additional dimensionality reduction analysis was performed on immune cells (FIG. 8b). Clusters were designated based on canonical marker genes as endothelial cells (EC; n=156), epithelial cells (EpC; n=384), immune cells (IC; n=356), and EnSC (n=2,345) (FIG. 8c). In addition, a discrete but as yet uncharacterized cluster of proliferating cells (PC; n=42) was identified (FIG. 8a). EpC segregated in 4 clusters with the most abundant population (EpC1) expressing prototypic receptivity genes (e.g. GPX3, PAEP, and DPP4) (FIG. 8c)[28]. EpC2 are ciliated epithelial cells found interspersed throughout endometrial glands (FIG. 9). EpC3 were derived from a single biopsy whereas EpC4 represented an ambiguous population expressing both epithelial and stromal marker genes (FIG. 8c). uNK cells, representing 89% of all IC, clustered into 3 subpopulations (NK1-3, FIG. 8d), matching the different NK populations described recently in pregnant decidua[29]. Based on cross-referencing of cluster-defining transcripts with canonical markers curated from the literature, the remaining immune populations were identified as naive B-cells (IC1), mono-cytes (IC2), and macrophage/dendritic cells (IC3) (FIG. 8d).

Figure 10:
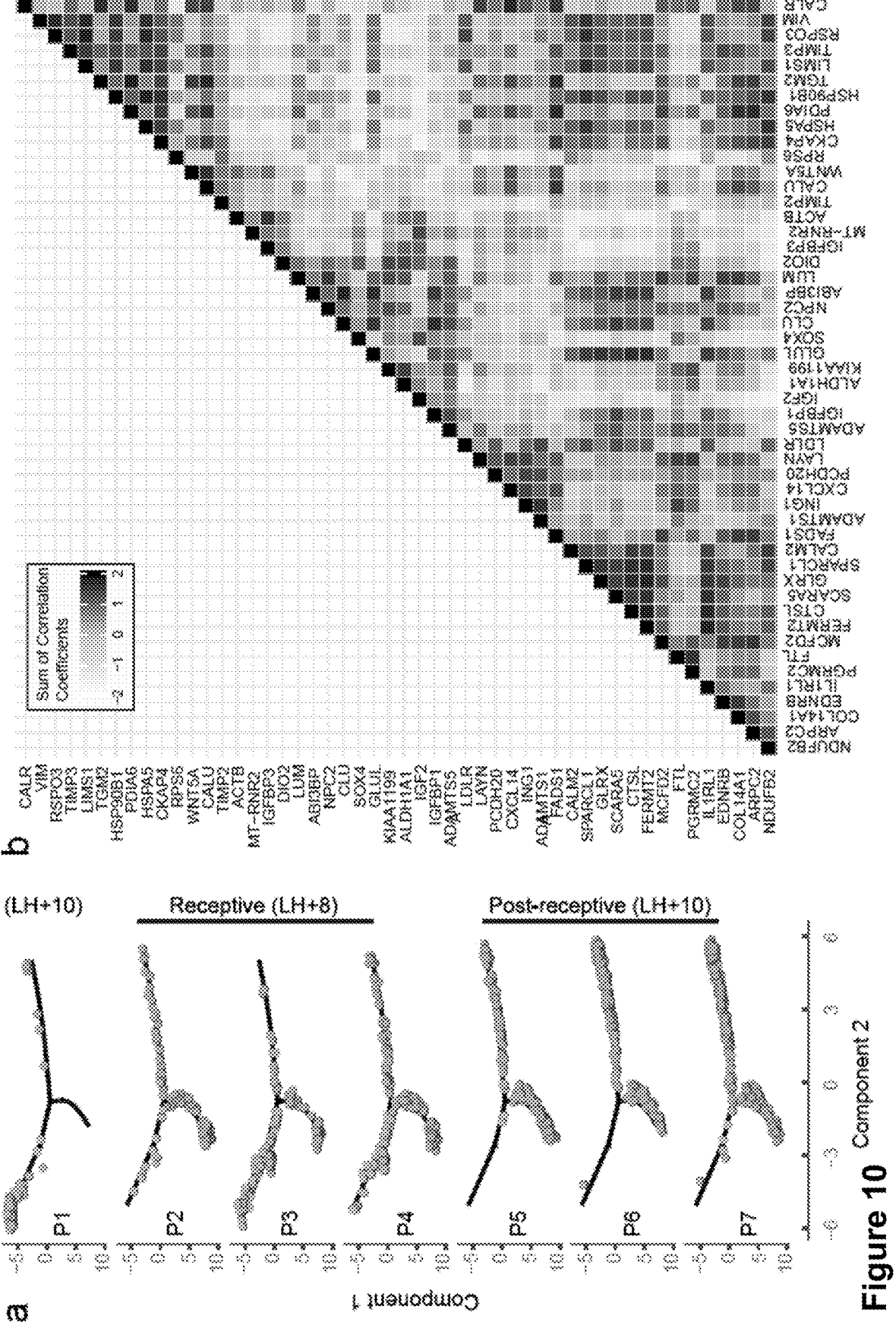
FIG. 10: Mapping of the differentiation trajectory of stromal cells across the window of implantation. (a) Pseudotime ordering of EnSC upon progression from the mid-luteal receptive phase (LH+8) to the late-luteal post-receptive phase (LH+10) of the cycle. (b) Heat map depicting the sum of correlation coefficients of the top 50 gene-gene interactions involved in lineage divergence of decidualizing EnSC in vitro and in vivo. The grayscale key indicates the level of congruency, defined as the sum of correlation coefficients of >1 or <−1 for positively (darker shade) and negatively (lighter shade) co-regulated genes, respectively.

Diffusion pseudotime was used to reconstruct lineage branching of differentiating EnSC in vivo. In all but one sample, the timing of the biopsy relative to the LH surge mapped closely to progression of EnSCs along a trajectory with one major branchpoint (FIG. 10a). The outlying sample, designated P1, was obtained at LH+10 (i.e. post-receptive) but aligned in pseudotime closer to LH+8 (receptive) samples. We surmised that the relationship between genes that drive branching into diverging lineages would, at least partly, be conserved in vivo and in vitro. To test this hypothesis, we selected the top 50 genes of branchpoint 1 in the decidual time-course and determined the Pearson correlations for each gene pair in EnSC in vitro and in vivo. We then calculated the sum of coefficients, ranging from +2 to −2. Congruency was defined as the sum of correlation coefficients of >1 or <−1 for positively and negatively co-regulated genes, respectively (FIG. 10b). Using this criterion, 27% of gene pairs were congruent, which was significantly more than expected by chance alone (hyper-geometric test: $P<10^{-82}$). For example, genes driving divergence of cultured EnSC into stress-resistant (e.g. SCARA5, ILIRL1, and GLRX) and senescent (e.g. ABI3BP, CLU and IGFBP1) populations also marked divergence of EnSC in vivo.

Decidual Dyshomeostasis in RPL

Figure 11:
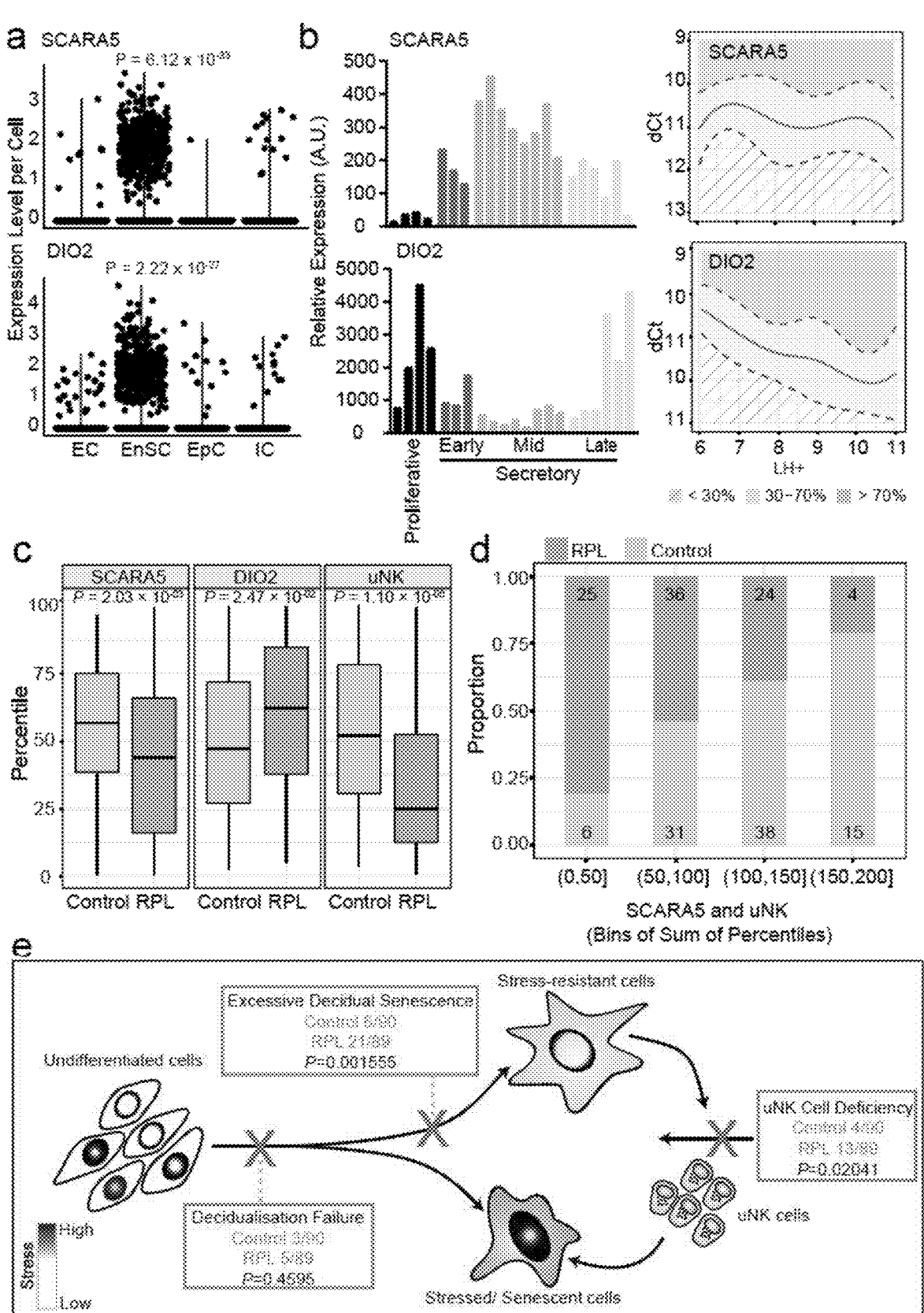
FIG. 11: Impaired fate divergence of decidual cells in RPL. (a) Single-cell analysis of luteal phase endometrial biopsies (n=7) demonstrates that expression of SCARA5 and DIO2 in vivo is largely confined to endometrial stromal cells (EnSC). EC, endothelial cells; EpC, epithelial cells; IC, immune cells (Wilcoxon rank sum test with Bonferroni correction). (b) Temporal expression of SCARA5 and DIO2 in cycling human endometrium. Left panel, expression of SCARA5 and DIO2 in proliferative and early-, mid-, late-luteal phase endometrium. Each bar represents an individual biopsy. The data were retrieved from microarray data deposited the Gene Expression Omnibus (GEO Profiles, GDS2052). Right panel, SCARA5 and DIO2 transcript levels were quantified by RT-qPCR analysis of 250 endometrial biopsies obtained between 6 to 11 days after the luteinizing hormone (LH) surge. Relative quantitation was performed using the $2^-$−ddCt with inclusion of an inter-plate calibrator sample. Centile calculations were performed on dCt values using R software. The median number of samples for each day was 43 (range: 30 to 46). (c) Distribution (percentile) of uNK cells and SCARA5 and DIO2 expression in timed endometrial biopsies of control subjects (n=90) and RPL patients (n=89) (Welch two-sided t-test). (d) Number of RPL and control subjects across 4 bins defined by the sum of SCARA5 and uNK cell percentiles. (e) Diagram illustrating the decidual pathway. Fate divergence of EnSC upon decidualization relates to the level of replicative stress (indicating by nuclear shading) incurred by individual cells during the proliferative phase. Stress-resistant decidual cells recruit and activate uNK cells to eliminate stressed/senescent decidual cells through granule exocytosis. Different defects along the decidual pathway can be identified, including 'decidualization failure', 'excessive decidual senescence', and 'uNK cell deficiency'. The frequency of each defect in RPL and control subjects is shown ($\chi^2$ test).

Expression of SCARA5 and DIO2 is largely confined to EnSC (FIG. 11a), rendering them putative markers to measure decidual subpopulations in clinical samples. To explore this possibility, we first profiled the expression of these two genes throughout the cycle and then measured their transcript levels in 250 samples obtained across the implantation window (LH+6-11) to generate centile graphs, based on the statistical distribution in gene expression for each day (FIG. 11b). In parallel, we used a clinically validated test to determine the percentile of $CD56^+$ uNK cells in each biopsy[15,30]. Next, we analyzed biopsies from control subjects (n=90) and RPL patients (n=89). Demographic characteristics are presented in Table 1 below. As shown in FIG. 11c, lower SCARA5 but higher DIO2 percentiles indicated a shift from stress-resistant to senescent decidual cells in RPL, which is in keeping with the loss of clonogenic endometrial progenitor cells reported previously[31]. uNK cells were significantly less abundant in RPL compared to control subjects (Welch two-sided t-test, P<0.0001). We reasoned that stress-resistant decidual cells and uNK cells drive successful transformation of the stroma into the decidua of pregnancy. Hence, we created 4 bins based on the sum of SCARA5 and uNK centiles and determined the number of RPL and control subjects in each bin. As shown in FIG. 11d, 81% (25/31) of subjects assigned to the lowest bin were RPL patients whereas 79% (15/19) in the highest bin were control subjects (Fisher's exact Test, P<0.0001). Our analysis also enabled a definition of putative defects across the pathway, including 'decidualization failure' (SCARA5: $\leq 30^{th}$ centile, DIO2: $\leq 30^{th}$ centile), 'excessive decidual senescence' (SCARA5: ≤30th centile, DIO2: $\geq 70^{th}$ centile), and 'uNK cell deficiency' (uNK cells: $\leq 30^{th}$ centile, SCARA5 and DIO2: $>30^{th}$-$<70^{th}$ centile) (FIG. 11e). Excessive decidual senescence and uNK cell deficiency were significantly more common in RPL patients compared to control subjects ($\chi^2$ test, P=0.0016 and P=0.02; respectively). Taken together, the incidence of decidual dyshomeostasis (i.e. encompassing all defects) was ~3-times higher in RPL compared to control subjects (44% versus 14%, respectively; Fisher's Exact test, P=0.00013).

TABLE 1

| | Subject Demographics | | |
| --- | --- | --- | --- |
| | Control* (n = 90) | RPL** (n = 89) | P-value† |
| Age (years) (Median ± IQR) | 36 (33-37) | 36 (33-38) | 0.253 |
| BMI (Median ± IQR) | 22 (21-25) | 26 (22-30) | <0.0001 |
| LH + day (Median ± IQR) | 9 (7-10) | 9 (7-10) | 0.968 |
| First trimester loss[Median (Range)] | 0 (0-2) | 5 (3-18) | <0.0001 |
| Live births [Mean (Range)] | 0 (0-2) | 0.35 (0-2) | <0.0001 |

*Control subjects were women awaiting IVF treatment for a variety of reasons, including male-factor, unexplained, and tubo-ovarian infertility. All subjects had regular cycles and considered to have good prognosis; recurrent IVF failure (RIF: >3 consecutive IVF failures with good quality embryos) patients were excluded.
**All Recurrent pregnancy loss (RPL) patients in this cohort had 3 or more consecutive miscarriages.
†Data wwere tested for normality using Shapiro-Wilk test. P-value was calculated by two-tailed unpaired student's t-test for normally distributed data (age) or two-tailed Mann Whitney test for non-normally distributed data (BMI, LH+, First trimester loss and Live births).

Discussion

Decidualization of the endometrium occurs in all euthe-rian (placental) mammals where placentation involves tro-phoblast invasion of the endometrial stroma[32]. In menstru-ating species, including humans, decidualization is not under the control of an implanting embryo but initiated during the midluteal phase of each cycle[33]. Once triggered, the decidu-alizing endometrium becomes inextricably dependent on sustained progesterone signaling. In the absence of implan-tation of a competent embryo, falling progesterone levels elicit an inflammatory decidual response which, upon recruitment and activation of leukocytes, leads to tissue breakdown, focal bleeding and menstrual shedding[34,35]. We set out to identify putative marker genes of diverging decidual populations using single-cell RNA-seq.

We first generated a detailed transcriptional map of pri-mary EnSC decidualized in culture. This analysis revealed a multi-step process that starts with a precipitous transcrip-tional response in differentiating EnSC, which is followed by synchronous transition of cells through intermediate states and then the emergence of divergent subpopulations, representing stress-resistant and acutely senescent decidual cells. A recent study asserted that decidual cells emerged in evolution from rewiring of an ancestral cellular stress response[19]. This conclusion was based on the observation that endometrial fibroblasts isolated from marsupials, which diverted from eutherians 60 to 80 million years ago[36], activate similar core regulatory genes as human EnSC in response to a decidualizing stimulus and then mount an acute inflammatory stress response akin to the initial decidual phase[19]. The key difference is that EnSC, or at least a subset, emerge from this process of inflammatory reprogramming as decidual cells expressing multiple genes involved in stress-resistance, anti-inflammation and cellular autonomy. However, other EnSCs fail to activate essential decidual effector genes and emerge as stressed/senescent cells, thus recapitulating the ancestral response. The precise mechanism underpinning lineage specification of individual EnSC into either stress-resistant or senescent decidual cells is unclear, although there is evidence that fate decisions may relate to the level of replication stress incurred by individual stromal cells during the preceding proliferative phase of the cycle[15].

Our single-cell analysis uncovered secreted markers of the diverging decidual populations and confirmed that stress-resistant decidual cells are programmed to eliminate their senescent counterparts by releasing factors, such CXCL14 and IL-15, involved in recruitment and activation of uNK cells[15,37,38]. Notably, hCG stimulates uNK cell proliferation directly[39], suggesting cooperation between the implanting embryo and mature decidual cells in eliminating senescent cells and curtailing tissue inflammation. We further showed that stress-resistant but not senescent decidual cells are responsive to progesterone withdrawal, which is in keeping with the marked up-regulation of senescent decidual genes and concurrent loss of stress-resistant decidual genes during the late luteal phase of the cycle, prior to menstrual tissue breakdown[15,40].

Single-cell transcriptomic analysis of timed endometrial biopsies yielded a number of notable results, including the discovery of a discrete but as yet uncharacterized population of proliferative mesenchymal cells, the characterization of different epithelial cell subsets, and the identification of 3 uNK cell states, which broadly corresponded to the different decidual NK cell subsets recently identified by single-cell analysis in early pregnancy[29]. Different NK cell states in mid-luteal endometrium were in part defined by the relative abundance of cell cycle genes. For example, the NK1 population, representing the most proliferating uNK cells, abundantly express genes involved in granule exocytosis (e.g. PRF1, GNLY, GZMA and GZMB). By contrast, NK3 cells express low levels of cell cycle genes but are defined by CCL5 and CXCR4 expression. Notably, CXCR4+ uNK cells have previously been implicated in vascular remodeling in pregnancy[41]. Importantly, we also showed that transition from receptive to post-receptive endometrial state is marked by progression of EnSC along diverging transcriptional trajectories, involving genes with conserved branching dynamics in vivo and in vitro. Although many branching genes are also expressed abundantly in other endometrial cell populations, we identified DIO2 and SCARA5 as putative marker genes for stressed and stressed-resistant decidual cells.

To test our hypothesis that perturbations along the decidual pathway predispose to pregnancy loss, we first generated centile graphs for SCARA5 and DIO2 expression using 250 endometrial midluteal biopsies (LH+6-11). This approach enables comparison of the relative level of gene expression in biopsies obtained at different days of the cycle. The relative abundance of uNK cells was also determined using a previously established centile graph based on analysis of 1,997 biopsies[15]. Next, we quantified the abundance of uNK cells and the expression of SCARA5 and DIO2 in timed endometrial biopsies from RPL and control subjects. Sample selection was based solely on reproductive history; all RPL patients had 3 or more consecutive miscarriages whereas control subjects were women with male-factor, tubal or unexplained infertility awaiting IVF treatment. Overall, our analysis indicated that pre-pregnancy endometrium in RPL is characterized by uNK cell deficiency in parallel with a shift from stress-resistant to senescent decidual cells. Next, we examined the frequency of different putative defects along the decidual pathway which may compromise the placental-decidual interface in early pregnancy. Based on pre-specified but arbitrary criteria, we found that RPL is associated with 'excessive decidual senescence' and 'uNK cell deficiency' but not 'decidualization failure'. The overall incidence of these putative defects, collectively termed 'decidual dyshomeostasis', was 44% in RPL patients compared to 14% in control subjects. While promising, prospective studies are needed to validate our observations and to define prognostic criteria that could be exploited for pre-pregnancy screening of women at risk of RPL.

Decidualization is an iterative process in cycling endometrium. At present, it is not clear if decidual dyshomeostasis in RPL persists from cycle-to-cycle or whether it represents an intermittent defect that affects some but not all cycles. The relative high cumulative live-birth rate in RPL favours the latter scenario[42]. Two distinct regulatory mechanisms control cellular homeostasis in cycling endometrium. Aside from resident progenitor cells in the basal layer, the endometrium actively recruits bone marrow-derived cells (BDMC) capable of differentiating into stromal, epithelial and endothelial cells[43]. Experimental studies have shown that BDMC enhance the regenerative capacity of non-pregnant endometrium[43], and plausibly contribute to rapid decidual expansion in pregnancy. On the other hand, rapid accumulation of uNK cells during the midluteal phase engenders selective elimination of senescent decidual cells through granule exocytosis, de facto rejuvenating the endometrium at the time of embryo implantation[15]. Thus, by balancing recruitment of BMDC and uNK cells, the endometrium is intrinsically equipped to fine-tune the decidual response to ensure implantation competence from one cycle to the next, and perhaps to adapt following pregnancy failure. However, pathological cues can disrupt these regulatory processes are predicted to increase the frequency of decidual dyshomeostasis and, by extension, the likelihood of miscarriage. For example, obesity is associated with loss of clonogenic progenitor cells in cycling endometrium[31,44] as well as uNK cell deficiency[45,46]. Obesity is also strongly associated with miscarriage, especially euploid pregnancy loss[47]. Thus, the prognostic value of a screening test based on endometrial analysis may be enhanced by incorporating clinical variables, such as maternal BMI, age and number of previous losses.

In summary, based on single-cell transcriptomic analysis of the decidual pathway, we identified SCARA5 and DIO2 as selective marker genes for stress-resistant and senescent decidual cells and used them to map putative defects along the decidual pathway. Here, we provided the first direct evidence of decidual dyshomeostasis in cycling endometrium and demonstrated that this process is caused by aberrant fate divergence of differentiating EnSC and uNK cell deficiency. Our findings raise the possibility of a simple screening test to identify women at risk of miscarriage and to monitor the effectiveness of pre-pregnancy interventions.

Example 2—Use of Molecular Timing to Assist Accuracy of Detection

Because of cycle-dependence, the interpretation of SCARA5/DIO2/uNK cell levels is advantageously assisted by knowledge of the day of the biopsy in the cycle. Practically, this can be achieved by scheduling the biopsy relative to the pre-ovulatory luteinising hormone (LH) surge as detected by home ovulation kits (e.g. LH+5 days to LH+11 days). While this pragmatic approach works generally well, there is a risk of erroneous timing of the biopsy because (i) patient error and (ii) intrinsic variation between the LH surge and the exact time of ovulation.

The window of implantation (also known as the receptivity window) is associated with dramatic changes in gene expression in glandular epithelium. Based on our single-cell analysis, two genes selectively expressed in glandular epithelium were identified: glutathione peroxidase 3 (GPX3—Ensembl: ENSG00000211445) and solute carrier family 15 member 2 (SLC15A2—Ensembl: ENSG0000163406). Further analysis of RNA-seq data generated in the laboratory, including RNA-seq analysis of laser-captured endometrial glands across the luteal phase of the cycle and bulk RNA-seq analysis of 36 endometrial biopsies, it was determined that GPX3 and SLC15A2 are regulated in opposing ways as the luteal phase unfolds (i.e. GPX3 is rapidly upregulated whereas SLC15A2 is rapidly downregulated). Consequently, the ratio of these two genes changes profoundly from day to day during the implantation window. Note that several other genes follow this pattern and thus could be employed for the purpose of 'timing'.

Analysis of 264 biopsies showed that the ratio between GPX3 and SLCC15A2 rises markedly across LH+5 and LH+11 days of the cycle. Note the log-transformed Y axis in FIG. 12a.

Figure 12:
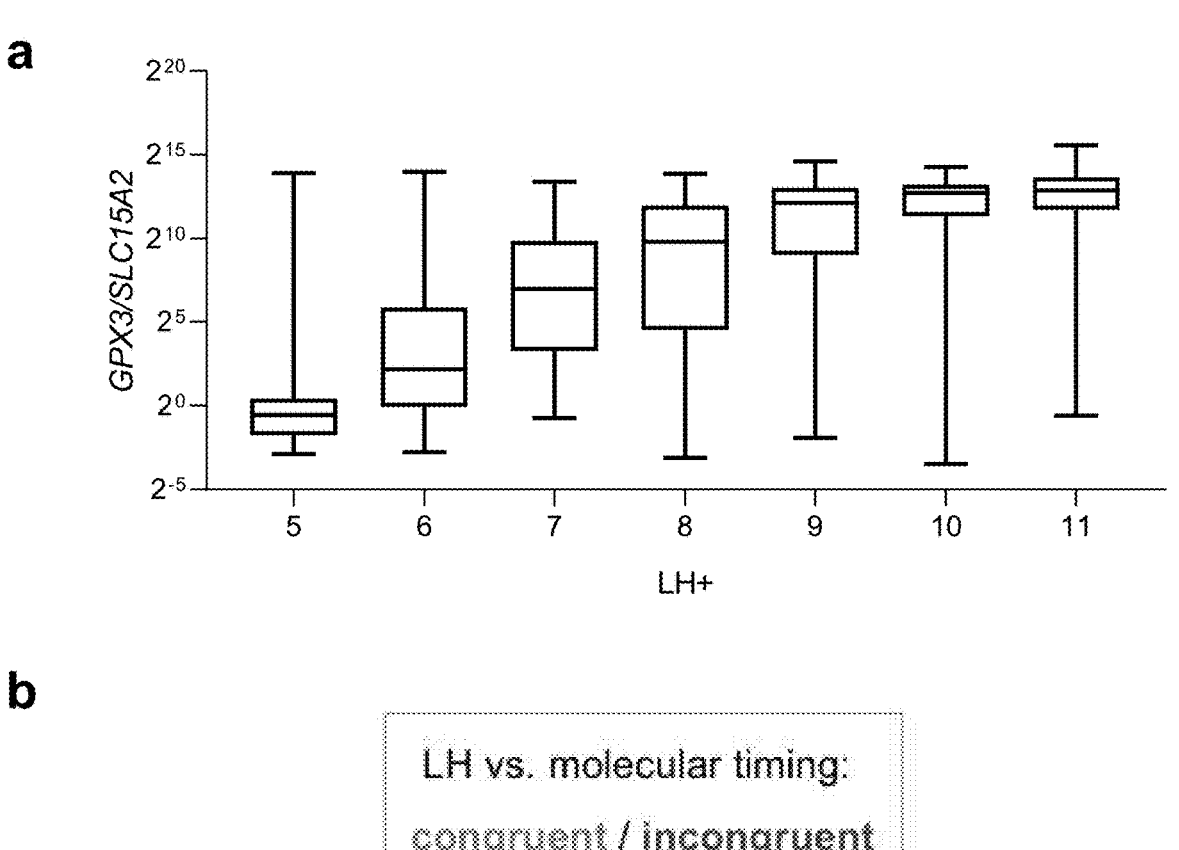
FIG. 12: Graph showing molecular timing across LH+5 to LH+11 days of the menstrual cycle. (a) Molecular timing based on the ratio of endometrial transcripts encoding GPX3 and SLC15A2. GPX3 and SLC15A2 are highly expressed in endometrial epithelial cells but regulated in opposing directions during the luteal phase of the cycle. The marked increase in GPX3/SLC15A2 mRNA ratio 6 to 9 days after the preovulatory rise in luteinising hormone (LH+6/9) indicates the transient window of implantation. GPX3 and SLC15A2 mRNA levels were measured by RT-qPCR in 264 LH-timed endometrial biopsies. LH timing is based on commercially available home ovulation kits. Note the log-transformed Y axis. (b) Reporting of biomarker results. Knowledge of the day of the endometrial biopsy within the cycle is essential for interpretation of biomarker analysis (e.g. SCARA5 and DIO2). The day of the biopsy in the cycle will be determined by two methods: (i) the number of days between the biopsy and the preovulatory LH surge, as determined by home ovulation kits; (ii) molecular timing based on the GPX3/SLC15A2 mRNA ratio. Timing will be considered confirmed/congruent if the GPX3/SLC15A2 ratio is between $25^{th}$-$75^{th}$ percentile for the day of the biopsy relative to the LH surge. Timing will be considered not confirmed/incongruent if the GPX3/SLC15A2 ratio is <$25^{th}$ or >$75^{th}$ centile for the day of the biopsy relative to the LH surge.

As outlined in the flow diagram in FIG. 12b, the timing of a biopsy could be considered 'confirmed' if the GPX3/SLC15A2 ratio is between $25^{th}$-$75^{th}$ percentile for the day of the biopsy as determined by home ovulation kit.

Incongruency between LH and molecular timing raises a number of biological possibilities which require further exploration. For the purpose of a test, in case of suspected mistiming, the SCARA5/DIO2/uNK analysis should be reported on the basis of the molecular as well as LH timing. Suspected 'mistiming' is likely to prompt repeat testing of the patient.

Example 3—Use of Sitagliptin for Miscarriage Prevention and Impact on Markers of Decidual Senescent Cells

Materials and Methods

Study Governance

The SIMPLANT study was approved by the Medicines and Healthcare Regulatory Authority (MHRA), the National Health Service Research Ethics Committee South Central-Hampshire B (16/SC/0229) and Research, Development and Innovation (RD&I) office at University Hospitals Coventry and Warwickshire (UHCW) National Health Service (NHS) Trust. The study was sponsored by UHCW NHS Trust and funded by Tommy's baby charity (registered charity 1060508/SC039280, Great Britain). The study protocol was submitted to the EU Clinical Trials Register (EudraCT number 2016-001120-54 issued 25 Jul. 2016). The date of enrolment of first participant was 15 Sep. 2016.

Participants

Participants were recruited from a tertiary recurrent miscarriage clinic at UHCW NHS Trust. Women were eligible if aged between 18 and 42 years, had a history of 3 or more consecutive miscarriages, and had regular menstrual cycles (up to 30 days in length). All participants were deemed to have unexplained miscarriages following standard RPL investigations. Participants agreed to actively avoid pregnancy and use barrier contraception for the duration of the trial. Exclusion criteria were diabetes mellitus and contraindications for the use of sitagliptin: history of pancreatitis, renal or hepatic impairment, taking digoxin or enalapril, and breastfeeding.

Sample Size

Sample size was determined by a power calculation based on previously reported data (67). Using a Poisson model and simulations, a sample size of 30 participants was calculated to have 91% power at 5% significance level to detect a difference when the mean CFU counts for placebo and sitagliptin groups are 3.4 and 6 per 1000 EnSC, respectively. To allow for drop-out, the planned minimum sample size was 34 women. Recruitment to the study was stopped after 30 women completed the study.

Intervention and Control Groups

The intervention group were allocated packs containing sitagliptin (100 mg) that had been encapsulated by Sharp Clinical Services (Powys, UK). Participants were instructed to take the capsules once daily from the day of the baseline biopsy for 3 menstrual cycles until the second biopsy was taken. The control group were allocated identical placebo capsules also supplied by Sharp Clinical Services and instructed to take these exactly as the intervention group.

Randomisation and Masking

The study statistician used the R statistical package to generate a randomisation list of 40 participants using the permuted block randomisation. The block sizes were 6, 8, 6, 8, 6 and 6; and the ratio of women in the two groups within a block was 1:1. A separate statistician checked the R programme used to generate the randomisation list, the final randomisation lists and the information inside all code break envelopes. Only the statisticians were unblinded to the block sizes and the master randomisation list. The statisticians were otherwise not involved in trial execution. Participants, the trial team, and laboratory staff were blinded to the medication assignment until completion of the trial. Immediately following the baseline biopsy, the clinical team contacted the RD&I office at UHCW NHS Trust to request treatment pack number allocation for each participant. These pack numbers were then allocated to participants using the randomisation list. The study statistician prepared a sealed 'code break envelope' for each participant, which was kept securely by the sponsor in case unblinding was required. Unblinding was not needed in the trial.

Transvaginal Ultrasound, Endometrial Biopsies and Scheduled Study Visits

Following written informed consent, participants were given a digital home ovulation test kit (Clearblue, Geneva, Switzerland), an emergency contact card, and barrier contraception. Participants then attended the clinic 7-10 days after the luteinizing hormone (LH) surge (LH+7-10). Following a negative urine pregnancy test, a transvaginal pelvic ultrasound scan was performed. Endometrial thickness was defined as the maximal endometrium diameter measured in a mid-sagittal plane. Next, an endometrial biopsy was obtained using a Wallach Endocell® endometrial sampler. The sample, designated 'baseline biopsy', was immediately portioned with one part stored in RNALater Stabilization Solution (Sigma-Aldrich, Dorset, UK) one part snap frozen in liquid nitrogen, one part fixed in 10% formalin for immunohistochemistry, and the remainder placed in 10% DMEM/F12 for isolation of primary endometrial stromal cells (see below). Following randomisation (see below), trial medication was provided and all participants attended two follow-up clinics at 4 weeks±4 day intervals. At these follow-up visits a urine pregnancy test was carried out, symptom diaries were reviewed, adverse events reported, and willingness for continued participation confirmed. At the second follow-up visit, participants were provided with another home ovulation test kit. In the third cycle, participants attended the clinic on LH+7-10 for a repeat transvaginal ultrasound scan with measurement of endometrial thickness and endometrial biopsy. The sample, designated 'second biopsy', was processed identically to the baseline biopsy. Trial medication was stopped on the day of the second biopsy.

Study Acceptability, Compliance, Adverse Events and Pregnancy Outcome

Participants were provided with compliance and symptom diaries at each visit. Diaries were assessed at every follow-up or biopsy visit. Acceptability and satisfaction of the study was assessed with a Likert scale-based questionnaire completed by participants after their final visit. Participants who conceived after completion of the study were requested to contact the trial team and outcome of the first pregnancy within one year of study completion was recorded.

Isolation of Primary EnSC

Primary EnSC were isolated according to our published protocol (65). Briefly, samples were washed in DMEM/F-12 medium (Invitrogen), finely minced and enzymatically digested with 0.5 mg/ml collagenase (Sigma-Aldrich) and 0.1 mg/ml deoxyribonuclease type I (Roche, Burgess Hill, UK) for 1 hour in 5% $CO_2$ at 37° C. Stromal and epithelial fractions were separated and cryopreserved in 10% DMSO in dextran-coated charcoal-stripped fetal bovine serum (DCC; 2 ml per vial; Invitrogen), with the stromal fraction split into two or three vials depending on the biopsy size. After controlled cooling at –80° C. overnight, samples were transferred to liquid nitrogen for storage.

Colony-Forming Unit (CFU) Assay

All CFU assays were conducted in batches, consisting of paired primary endometrial stromal cells isolated from baseline and second biopsies from 3 or 4 participants. CFU assays were established as described previously (66). Briefly, cryopreserved stromal cells were thawed for 3 minutes at 37° C. and then transferred immediately into pre-warmed growth medium (DMEM-F12 medium containing 10% DCC supplemented with 1% L-Glutamine and 1% antibiotic-antimycotic mix; Invitrogen). Cells were pelleted by centrifugation at 276×g for 5 minutes, supernatant was aspirated and cells were resuspended in 10 ml growth medium. Viable stromal cells were counted in trypan blue on a Neubauer Improved haemocytometer and seeded at clonal density (53 cells/cm2) onto fibronectin-coated 6-well plates (10 µg/ml in PBS; Sigma-Aldrich) in growth medium supplemented with 10 ng/µl basic fibroblast growth factor (Sigma Aldrich). Three wells, containing 500 cells each, were seeded per biopsy. Plates were cultured in 5% CO2 at 37° C., and left undisturbed for 3 days after which growth was monitored to ensure colonies arose from single cells.

The culture media was half-changed after 7 days of culture. On day 10, cultures were washed in phosphate buffered saline (PBS), fixed in 10% neutral buffered formalin for 10 minutes at room temperature, washed extensively in sterile water and then stained with Harris hematoxylin for 4 minutes. After extensive washing in sterile water, plates were incubated in PBS for 4 minutes to intensify the stain. PBS was removed and plates washed again in sterile water then allowed to dry. For counting colonies, plates were imaged using a G:Box dark room imager and GeneSys software (Syngene). Images were analysed in ImageJ by a single operator using the cell counter plugin to count colonies of 50 cells or larger (67). The pre-specified primary outcome measure was the CFU count per 1000 EnSC seeded after 3 cycles of Sitagliptin or placebo. However, to mitigate against loss of data in case of infection, a total of 1500 cells were seeded in 3 wells of a 6-well plate per sample. As there were no obvious criteria to exclude the colony count from a given well, the results are presented as CFU count per 1500 EnSC.

DPP4 Activity Assay

DPP4 activity was measured in whole tissue lysates from snap-frozen endometrial biopsies using DPP4 Activity Assay Kit (Sigma-Aldrich) according to the manufacturer's instructions. DPP4 activity was normalized to total protein content.

Reverse Transcription Quantitative PCR (RT-qPCR)

RNA was extracted from RNAlater preserved tissue using the RNeasy Lipid Tissue Mini Kit (QIAGEN, Manchester, UK), with on-column DNase treatment, according to the manufacturer's instructions. RNA was assessed using a Nanodrop ND-1000 spectrophotometer and 1 µg RNA used for reverse transcription, performed using the Quantitect Reverse Transcription Kit (QIAGEN) according to manufacturer's instructions. Thermal cycling was performed on a QuantStudio 5 Real-Time PCR System (ThermoFisher, Paisley, UK), using PrecisionPlus 2× Mastermix (Primer Design, Southampton, UK), 300 nM each forward and reverse primers and 1 µl cDNA. L19 was used as a reference gene and data were analysed using the Pfaffl method (68). Primer sequences were as follows: PRL (F) 5'-AAG CTG TAG AGA TTG AGG AGC AAA C-3' (SEQ ID NO: 7), PRL (R) 5'-TCA GGA TGA ACC TGG CTG ACT A-3' (SEQ ID NO: 8); DPP4 (F) 5'-CCA AAG ACT GTA CGG GTTC C-3' (SEQ ID NO: 9), DPP4 (R): 5'-ACA AAG AAC TTT ACA GTT GGA TTC AC-3' (SEQ ID NO: 10); IGFBP1 (F) 5'-CGA AGG CTC TCC ATG TCA CCA-3' (SEQ ID NO: 11), IGFBP1 (R), 5'-TGT CTC CTG TGC CTT GGC TAA AC-3' (SEQ ID NO: 12); SCARA5 (F) 5'-CAT GCG TGG GTT CAA AGG TG-3' (SEQ ID NO: 1), SCARA5 (R) 5'-CCA TTC ACC AGG CGG ATC AT-3' (SEQ ID NO: 2); DIO2 (F) 5'-ACT CGG TCA TTC TGC TCA A-3' (SEQ ID NO: 3), DIO2 (R) 5'-TTC CAG ACG CAG CGC AGT-3' (SEQ ID NO: 4); L19 (F) 5'-GCG GAA GGG TAC AGC CAA T-3' (SEQ ID NO: 5), L19 (R) 5'-GCA GCC GGC GCA AA-3' (SEQ ID NO: 6).

Organoid Forming Efficiency Assay

Endometrial epithelial cells (EnEC) were isolated as described previously (65) and seeded at a density of 300 cells per 5 µl ice cold Matrigel (Corning) in 96-well plates. Matrigel was first polymerised at 37° C. for 45 minutes and then 100 µl organoid expansion medium (69), supplemented with or without sitagliptin, was added. Medium was changed every 2 days and the number of organoids per well was counted after 10 days. At least 3 wells per sample were counted and averaged. The following formula was used to calculate organoid forming efficacy: OFE (%)=(number of organoids/cells seeded)×100.

Immunohistochemistry

Endometrial biopsies were fixed overnight in 10% neutral buffered formalin at 4° C. and wax embedded in Surgipath® Formula 'R'™ paraffin using the Shandon Excelsior ES Tissue processor (ThermoFisher). Tissues were sliced into 3 µM sections on a microtome and adhered to coverslips by overnight incubation at 60° C. Deparaffinization, antigen retrieval (sodium citrate buffer; 10 mM sodium citrate, 0.05% Tween-20, pH 6), antibody staining, hematoxylin counter stain and DAB colour development were fully automated in a Leica BondMax autostainer (Leica BioSystems). Tissue sections were stained for CD56 (a uNK-specific cell surface antigen) using a 1:200 dilution of concentrated CD56 antibody (NCL-L-CD56-504, Novocastra, Leica BioSystems). The relative abundance of uNK cells (number of CD56-positive cells per 100 stromal cells) and uNK cell percentile, i.e. normalized to the day of the biopsy following the LH surge, were calculated as described previously (15, 70).

Statistical Analysis

Participant characteristics [age, body mass index (BMI), number of previous miscarriages] and baseline and second CFU counts were summarised as the mean, median, minimum, maximum, standard deviation and interquartile range. Mann-Whitney U test was used to compare baseline characteristics between the placebo and sitagliptin groups. The primary analysis fitted a Poisson regression model to compare the mean CFU count per 1500 EnSC following 3 cycles of sitagliptin or placebo. As planned in the protocol, a secondary analysis adjusted for characteristics that were imbalanced between control and intervention: age and baseline CFU count. To estimate the increase from baseline, a random effects Poisson regression model that consisted of the baseline and second CFU counts was fitted. The random effects model included an interaction term for cycle and group. An exploratory subgroup analysis excluding 8 women with substantially higher baseline CFU count (>20 colonies per 1500 cells seeded) was also performed.

For other secondary outcome measures, Kruskal-Wallis with Dunn's post-hoc test for multiple comparisons was used for grouped analysis. Wilcoxon matched-pairs signed rank test with Sidak correction (alpha=0.0253) was used to compare gene expression before and after treatment, and without Sidak correction for analysis of paired CFU and OFE assays. Mann Whitney U was used for pairwise comparison of cell type specific expression in primary cultures. One-Way ANOVA for matched data with Tukey's post-hoc test for multiple comparisons was used for analysis of sitagliptin dose response experiments. Wilcoxon matched-pairs signed ranks test was used for. Unless stated otherwise, $P<0.05$ was considered significant.

Results

Patient Recruitment and Trial Completion

The study was discussed with 73 patients attending a tertiary recurrent miscarriage clinic with a severe RPL phenotype, defined by the number of previous miscarriages and no known history of aneuploid pregnancy losses. Of these, 42 consented to the study but four were lost prior to randomisation; two withdrew consent, one participant had a urea level outside the reference range, and insufficient tissue was obtained in the baseline biopsy of one participant. A total of 19 women were allocated to each treatment group. In the sitagliptin group 16 completed the study, one participant was withdrawn by the sponsor, one opted-out and one was lost to follow-up. In the placebo group, two participants became pregnant during the trial and 17 completed the study. The CONSORT diagram is presented in FIG. 13. The first participant consented on 15 Sep. 2016 and the last participant to have a second biopsy attended on 16 Feb. 2018.

Patient Characteristics and CFU Counts

The median number of previous miscarriages in the sitagliptin and placebo groups was 5.5 and 8, respectively (Table 2), underscoring the severity of the RPL phenotype of study participants. The number of previous pregnancy losses, BMI, and baseline CFU counts were not significantly different between the sitagliptin and placebo groups ($P<0.05$; Table 2). However, the median age of participants in the sitagliptin group was higher than in the placebo group (36 vs. 32 years, P=0.02) (Table 2).

TABLE 2

| Patient demographics and CFU counts at baseline and second biopsy | | | |
|---|---|---|---|
| | Sitagliptin Group (n = 16) | Placebo Group (n = 17) | P-value[†] |
| Age (years) | | | |
| Median (IQR, Range) | 36.0 (31.3-38.0, 26-40) | 32.0 (29.0-33.5, 24-36) | 0.02 |
| BMI | | | |
| Median (IQR, Range) | 27.3 (22.4-30.3, 19.5-35.7) | 25.6 (22.8-27.8, 21.1-38.4) | 0.53 |
| Number of miscarriages | | | |
| Median (IQR, Range) | 5.5 (5.0-7.0, 3-14) | 8.0 (5.0-9.5, 3-14) | 0.36 |
| Baseline CFU count | | | |
| Median (IQR, Range) | 8.5 (4.5-17.8, 1-74) | 12.0 (6.3-45.8, 2-78)[‡] | 0.49 |
| Mean (SD) | 16.1 (19.6) | 24.2 (25.6) | |
| Second biopsy CFU count | | | |
| Median (IQR, Range) | 14.0 (8.0-29.0, 3-145)[‡] | 11.0 (5.5-37.5, 3-98) | 0.65 |
| Mean (SD) | 27.7 (35.8) | 25.1 (27.3) | |

[†]Mann-Whitney U test;
[‡]Data missing for one participant.

Note

CFU counts are per 1500 EnSC.

Figures 14, 15:
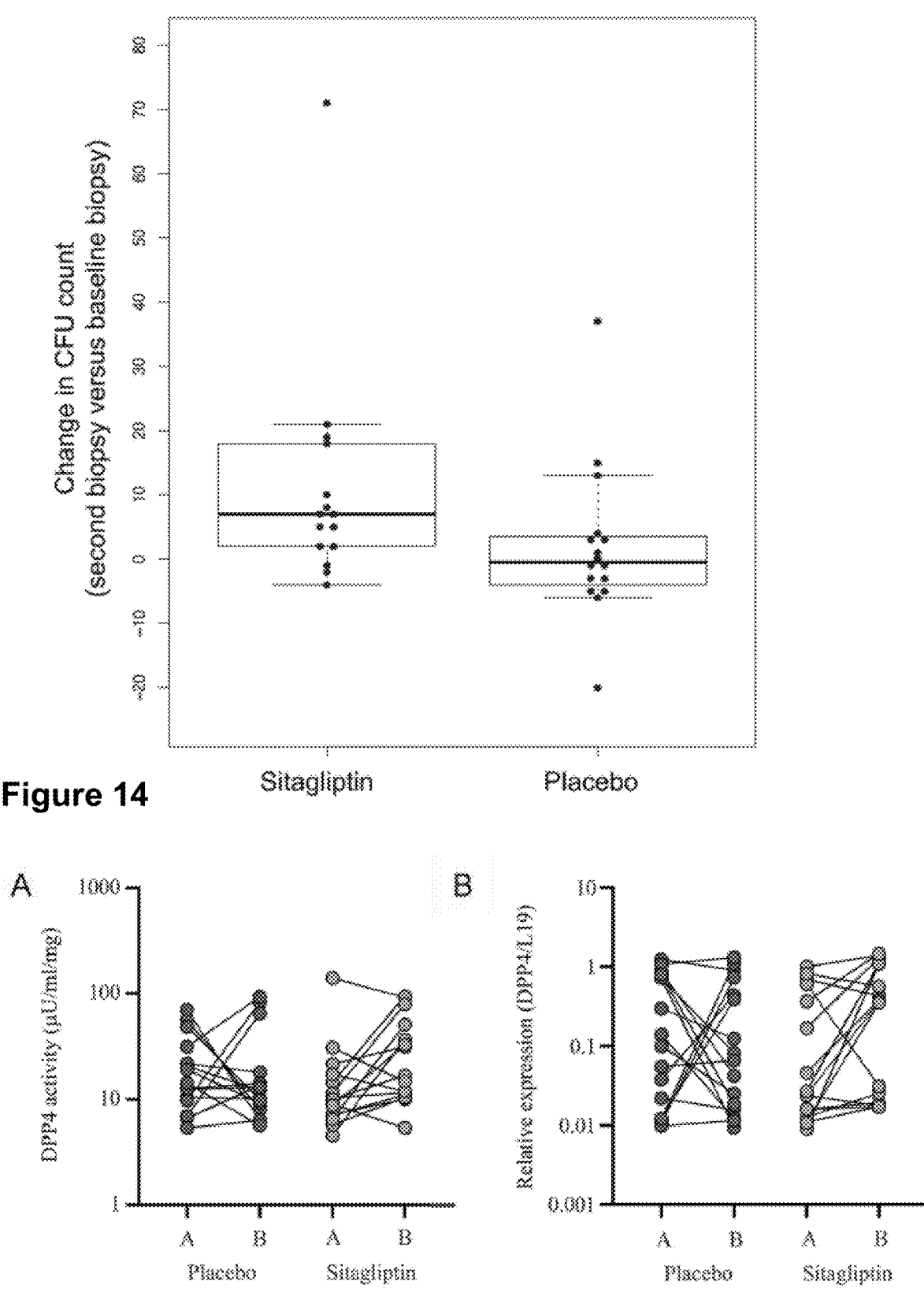
FIG. 14: Change in CFU count after 3 cycles of sitagliptin or placebo. The median increase in CFU count in the second compared to the baseline biopsy was +7 per 1500 EnSC and −0.5 per 1500 EnSC in the sitagliptin and placebo group, respectively (P<0.01).
FIG. 15: Oral sitagliptin does not inhibit endometrial DPP4. (A) DPP4 activity (left panel) was measured in paired baseline ($1^{st}$) and second ($2^{nd}$) in tissue lysates extracted from snap-frozen biopsies obtained from participants randomised to placebo (n=15) or sitagliptin (n=15). DPP4 activity was normalized to total protein content. (B) DPP4 mRNA level, normalized to L19 and expressed as arbitrary units, was measured by RT-qPCR in paired baseline ($1^{st}$) and second ($2^{nd}$) endometrial biopsies obtained from participants randomised to placebo (n=16) or sitagliptin (n=16).

The primary outcome measure was based on the CFU count of the second biopsy upon completion of the trial; hence, intention to treat analysis was not possible. Although 33 participants completed the trial, a CFU count on the second biopsy was available for 32 subjects because of one case of yeast contamination in the sitagliptin group. Conversely, the baseline count was lacking for one subject in the placebo group as no viable cells were recovered. The primary outcome analysis showed no significant difference in the unadjusted mean CFU count after 3 cycles of sitagliptin compared to placebo (P=0.15; Table 3). When adjusted for baseline CFU count, the mean CFU count in the second biopsy was significantly higher in the sitagliptin group compared to the placebo group (27.67 vs. 25.06, RR: 1.51, 95% CI=1.31-1.73, P<0.01). Adjusting for age and baseline CFU count had minimal impact on results (Table 3). Unadjusted subgroup analysis that excluded 8 outlying CFU counts (>20 colonies per 1500 cells) also demonstrated significantly higher CFU counts following sitagliptin treatment compared to placebo (14.42 vs. 11.00, RR: 1.31, 95% CI=1.04-1.63, P=0.02). As shown in FIG. 14, CFU count in the second biopsy was significantly higher when compared to the baseline biopsy in the sitagliptin arm (median increase in colonies: +7 per 1500 cells, 1.68-fold the baseline count, P<0.01). By contrast, there was no significant increase in the CFU count between the baseline and second biopsy in the placebo group (median increase: −0.5 per 1500 cells, 1.08-fold the baseline count, P=0.26) (FIG. 14 and Table 4).

Endometrial Thickness, Study Acceptability, and Subsequent Pregnancy Outcome

The mean endometrial thickness at baseline was 9.0 mm [interquartile range (IQR): 8.5-10.0 mm] and 8.9 mm (IQR: 7.2-97 mm) in the placebo and sitagliptin groups, respectively. Mean endometrial thickness at the time of the second biopsy was 9.6 mm (IQR: 7.7-10.3 mm) and 8.0 mm (IQR: 7.2-10.6 mm) in the placebo and sitagliptin groups, respectively. Hence, endometrial thickness was within the expected midluteal range for all participants and not significantly different between the placebo and sitagliptin groups, either at baseline or at the time of the second biopsy (P>0.05, Kruskall-Wallis test).

Compliance to study medication was high. Out of 33 participants who completed the study, 32 demonstrated near full compliance (>98%). Study medication compliance was 50% for one participant randomised to placebo. A questionnaire with Likert scale responses and space for free text comments showed that all participants agreed or agreed strongly that taking part in the study was worthwhile, would recommend the study to others, and found that taking the medication was easy. The only adverse event reported by more than one participant was headache, which occurred in 7 and 4 participants in the placebo and sitagliptin group, respectively; and therefore not attributable to study medication. Table 5 lists all reported side-effects.

TABLE 3

| CFU count after 3 cycles of sitagliptin or placebo (second biopsy) | | | | |
|---|---|---|---|---|
| | | | Rate ratio (95% Confidence interval), P value | |
| | Mean CFU count[†] | | | Adjusted for baseline Adjusted for baseline |
| | Sitagliptin | Placebo | Unadjusted analysis | count | count and age |
| All data | 27.7 | 25.1 | 1.10 (0.96, 1.26), P = 0.15[‡] | 1.51 (1.31, 1.73), P < 0.01 | 1.52 (1.32, 1.75), P < 0.01 |
| Subgroup data[†] | 144 | 110 | 1.31 (1.04, 1.67), P = 0.02 | 1.43 (1.13, 1.80), P < 0.01 | 1.67 (1.29, 2.17), P < 0.01 |

[†]Excludes data for women with outlying CFU counts;

[‡]Prespecified primary analysis.

Note

CFU counts are per 1500 EnSC.

TABLE 4

| Results of the random effects Poisson regression model | | | |
|---|---|---|---|
| | Rate ratio: second to baseline biopsy (95% confidence interval), P value | | Rate ratio: sitagliptin to placebo (95% confidence interval), P value |
| | Sitagliptin | Placebo | Baseline | Second biopsy |
| All data | 1.68 (1.44, 1.97) , P < 0.01 | 1.08 (0.94, 1.24), P = 0.26 | 0.97 (0.71, 1.31), P = 0.82 | 1.49 (1.12, 2.00), P < 0.01 |
| Subgroup[†] | 1.88 (1.47, 2.41), P < 0.01 | 1.27 (0.97, 1.66), P = 0.08 | 1.01 (0.71, 1.43), P = 0.95 | 1.49 (1.09, 2.04), P < 0.01 |

[†]Excludes data for women with high baseline CFU

TABLE 5

| | Placebo (n = 19) | Sitagliptin (n = 19) |
|---|---|---|
| Adverse event/Side Effect | Events (participants) | Events (participants) |
| Headache | 26 (7) | 10 (4) |
| Dizziness | 0 | 2 (1) |
| Nausea | 0 | 1 |
| Thirst | 0 | 1 |
| Myalgia | 1 | 1 |
| Diarrhoea | 2 (2) | 0 |
| Dry mouth | 1 | 1 |
| Sore Throat | 1 | 1 |
| Dry Nose | 1 | 0 |
| Stuffy Nose | 1 | 0 |
| Rash | 2 (1) | 0 |
| Chills | 1 | 1 |
| Night sweats | 0 | 1 |
| Mouth ulcers | 1 | 0 |
| Nose bleed | 1 | 0 |
| UTI | 0 | 1 |
| Thinning of hair | 1 | 0 |
| Low Mood | 0 | 1 |

Adverse events and side effects

We recorded the outcome of the first pregnancy within 12 months following completion of the study. Out of 34 participants enrolled in the study, 25 reported a pregnancy outcome within this timeframe. In the sitagliptin group, there were 8 live births, one termination of pregnancy at 16 weeks for a fetal abnormality (cerebellar agenesis), and 3 spontaneous pregnancy losses before 12 weeks of gestation. Cytogenetic analysis was performed in 2 of 3 miscarriage cases and both showed fetal aneuploidy (trisomy 22 and triploidy). In the placebo group, there were 7 live births and 6 spontaneous pregnancy losses before 12 weeks. Cytogenetic analysis was performed in one case and showed normal fetal karyotype.

Explorative Investigations: Oral Sitagliptin Inhibits Decidual Senescence but not Endometrial DPP4 Activity DPP4 is known maker of glandular differentiation during the midluteal phase of the cycle (60). DPP4 is also a widely used endometrial receptivity marker gene (61). To explore the mechanisms of sitagliptin actions in the endometrium, we first measured DPP4 activity on snap-frozen, paired baseline and second biopsies from the placebo group (n=15) and sitagliptin group (n=15). In addition, paired placebo (n=16) and sitagliptin (n=16) samples preserved in RNA later were used to measure DPP4 mRNA levels by RT-qPCR. As shown in FIG. 15, there was no evidence that oral sitagliptin (100 mg daily) for 3 cycles inhibits endometrial DPP4 expression or activity (P>0.025, Wilcoxon test).

We also explored if sitagliptin impacts on the clonogenicity of primary EnSC or endometrial epithelial cells (EnEC) isolated from independent midluteal biopsies. As shown in FIG. 16A, DPP4 activity was 3-fold higher in primary EnEC when compared to EnSC (P<0.001, Mann-Whitney U test). Exposure of primary EnEC and EnSC to pharmacological concentrations of sitagliptin inhibited DPP4 activity by ~90% (FIG. 16B). Next, we performed CFU assays on cultured EnSC seeded at very low cell density with basic fibroblast growth factor in the presence or absence of 100 µM sitagliptin for 10 days. No difference in colony forming efficiency of the stromal fraction was observed between control and sitagliptin treated cultures (FIG. 16C, upper panel; P>0.05, Wilcoxon test). To test the impact on epithelial progenitor cells, we made use of a recently published protocol that enables formation of gland organoids from single endometrial epithelial progenitor cells (69). Briefly, freshly isolated EnEC were seeded at low density in Matrigel and then cultured for 10 days in a chemically defined expansion medium that contains epidermal growth factor, fibroblast growth factor 10, hepatocyte growth factor, Noggin (BMP4 antagonist), R-spondin-1 (WNT/β catenin pathway agonist), A83-01 (Alk3/4/5 inhibitor), and nicotinamide. Again, addition of sitagliptin to the expansion medium had no impact on endometrial gland organoid forming efficiency (FIG. 16C, lower panel; P>0.05, Wilcoxon test).

Next, we examined the expression of decidual markers in paired baseline and second biopsies stored in RNA stabilization solution from the placebo (n=16) and sitagliptin (n=16) group. Induction of PRL and IGFBP1 expression is widely used to monitor the decidual response in cultured EnSC (14). However, these marker genes do not discriminate between decidual cells and senescent decidual cells. By contrast, SCARA5 and DIO2 are stromal-specific marker genes of decidual cells and senescent decidual cells, respectively, both in vitro and in vivo. PRL and IGFBP1 transcript levels were not significantly different in the second biopsy compared to the baseline biopsy in either the placebo or treatment group (FIG. 17, P>0.025, Wilcoxon test). By contrast, sitagliptin treatment but not placebo resulted in a significant reduction in mean DIO2 mRNA levels in the second biopsy compared to the baseline biopsy (FIG. 18A, left panel [median: 3.86 arbitrary units (a.u.) vs. 5.09 a.u., respectively, P=0.0182, Wilcoxon test], whereas SCARA5 mRNA levels were not altered significantly (FIG. 18A, right panel; P>0.025). Thus, sitagliptin treatment not only increases the abundance of eMSCs in the endometrium but also rebalances the relative abundance of decidual cell subpopulations, as measured by the fold-change in SCARA5/DIO2 ratio (FIG. 18B), by attenuating decidual senescence.

Discussion

This study reports on the feasibility of using oral sitagliptin (100 mg daily) to increase the abundance of eMSC in RPL patients. The primary outcome of this randomised, double-blind, placebo-controlled trial was CFU counts after 3 cycles of sitagliptin or placebo. Unadjusted analysis showed no statistically significant difference in CFU counts between the groups but this was accounted for by the unanticipated magnitude of interpatient variation in CFU counts. Baseline CFU counts ranged from 1 to 78 colonies per 1500 cells seeded (0.07% to 5.2%, respectively), although only 8 subjects had CFU counts of more than 20 colonies per 1500 cells (>1.3%). When adjusted for baseline CFU count, the mean CFU count in the second biopsy was 51% higher in the sitagliptin group compared to the placebo group. Compared to the baseline biopsy, sitagliptin given for 3 menstrual cycles increased CFU counts on average by 68%. By contrast, there was no significant change in CFU counts in the placebo group, attesting to the robustness of the endometrial response to oral sitagliptin. Notably, participants randomised to the sitagliptin treatment were older when compared to the placebo group. However, in line with a previous study (71), we found no evidence of a significant impact of age on either baseline CFU counts or on the response to sitagliptin. Explorative investigations indicated that the increase in eMSC in response to sitagliptin is biologically meaningful and associated with a significant reduction in senescent decidual cells. Notably, oral sitagliptin (100 mg daily) does not inhibit uterine DPP4 expression or activity. We also found no evidence that sitagliptin impacts directly on the clonal capacity of eMSCs or organoid formation efficacy of epithelial progenitor cells. Taken together, these exploratory observations are compatible with the hypothesis that oral sitagliptin inhibits DPP4-dependent inactivation of SDF-1 in the circulation (72) and that homing and engraftment of BMDC in cycling endometrium is dependent on the level of circulating bioactive SDF-1 (73, 74, 75). Importantly, our feasibility trial also demonstrated the acceptability of pre-pregnancy sitagliptin treatment in RPL patients. Drug compliance was high and no adverse events were reported. Although the trial was not designed or powered to assess to assess pregnancy outcome, only 3 spontaneous miscarriages were reported out of 12 pregnancies in the sigliptin group, two of which were found to be caused by fetal aneuploidies.

The ability of gliptins to enhance regeneration of damaged tissues has been explored in other organs but by and large the clinical results have been disappointing. For example, intracoronary administration of BMDC has been shown to improve recovery of left ventricular contractile function in patients with acute myocardial infarction (76), whereas a combination of granulocyte-CSF-dependent mobilisation of BMDC followed by sitagliptin treatment (100 mg for 28 days) failed to improve cardiac function (77). However, a particular advantage of the endometrium over other tissues, such as heart or kidney, is that DPP4 inhibitors can be initiated prior or during (menstrual) tissue injury and sustained over multiple cycles.

A pharmacological approach to increase endometrial progenitor populations could be useful in the management of other intractable reproductive disorders. For example, in a murine model of thin endometrium, tissue regeneration and pregnancy rates were increased following treatment with either BMDC or SDF-1 (63). A recent non-controlled study reported that autologous cell therapy in conjunction with hormonal replacement therapy temporarily improves endometrium thickness, as well as the volume and duration of menses, in patients with refractory Asherman's syndrome or endometrial atrophy (78). This approach requires mobilization of BMDC using granulocyte-colony stimulating factor, isolation of CD133$^+$ endothelial progenitors through peripheral blood aphaeresis, and finally delivery of cells into the spiral arterioles by catheterization under angiography. Although we found no evidence that sitagliptin increases endometrial thickness during the luteal phase in this study, it should be noted that none of the participants had an abnormally thin midluteal endometrium.

Patient Selection and Drug Dosing and Timing Considerations

Our study raises a number of issues that should be considered in future studies. The first issue relates to selection of RPL patients most likely to benefit from treatment with sitagliptin. Ideally, recruitment in future studies should be based on pre-pregnancy screening for eMSC deficiency and/or excessive decidual senescence. However, it is impractical to use CFU assays in large-scale clinical studies and the use of decidual marker genes for screening purposes requires further validation. Alternatively, patients could be selected on basis of risk factors associated with euploid pregnancy loss, including the number of previous miscarriages (4, 8), a prior history of euploid pregnancy loss (3), and obesity (47). Second, in this study we opted for continuous sitagliptin treatment over 3 cycles based on the assumption that the effect on eMSC may be cumulative over multiple menstrual 'injuries'. It is possible that homing and engraftment of BMDC in the endometrium is physiologically restricted to the proliferative phase of the cycle. This conjecture is supported by murine studies demonstrating that oestradiol coordinates the induction of SDF-1 expression in EnSC with the expression of the SDF-1 receptor, C-X-C motif chemokine receptor 4 (CXCR4), in BMDC (62). This means that DPP4 inhibition needs to be in place prior to menstruation. The National Institute for Health and Care Excellence (NICE) in the UK advises against the use of sitagliptin in pregnancy, hence pre-pregnancy treatment regime is needed. Another consideration relates to the optimal dose of sitagliptin for the purpose of miscarriage prevention in RPL. In this study, we used 100 mg of sitagliptin daily, which is the recommended dose for glycaemic control in type 2 diabetes (79). However, a recent study reported that much higher doses of sitagliptin (up to 600 mg twice daily) result in more sustained plasma DPP4 inhibition and improve engraftment of haematopoietic stem and progenitor cells in bone marrow following umbilical cord blood transplantation in patients with haematological cancers (80). Whilst such large doses might be considered in individuals affected by life threatening conditions such as malignancy they are not something that can be considered in healthy women suffering recurrent pregnancy loss.

REFERENCES

1 Rai, R. & Regan, L. Recurrent miscarriage. *Lancet* 368, 601-611, doi:10.1016/S0140-6736(06)69204-0 (2006).

2 Hardy, K., Hardy, P. J., Jacobs, P. A., Lewallen, K. & Hassold, T. J. Temporal changes in chromosome abnormalities in human spontaneous abortions: Results of 40 years of analysis. *Am J Med Genet* A 170, 2671-2680, doi:10.1002/ajmg.a.37795 (2016).

3 Hassold, T. et al. A cytogenetic study of 1000 spontaneous abortions. *Ann Hum Genet* 44, 151-178 (1980).

4 Ogasawara, M., Aoki, K., Okada, S. & Suzumori, K. Embryonic karyotype of abortuses in relation to the number of previous miscarriages. *Fertility and sterility* 73, 300-304 (2000).

5 Stephenson, M. D., Awartani, K. A. & Robinson, W. P. Cytogenetic analysis of miscarriages from couples with recurrent miscarriage: a case-control study. *Hum Reprod* 17, 446-451 (2002).

6 Sullivan, A. E., Silver, R. M., LaCoursiere, D. Y., Porter, T. F. & Branch, D. W. Recurrent fetal aneuploidy and recurrent miscarriage. *Obstet Gynecol* 104, 784-788, doi: 10.1097/01.AOG.0000137832.86727.e2 (2004).

7 Carp, H. et al. Karyotype of the abortus in recurrent miscarriage. *Fertil Steril* 75, 678-682 (2001).

8 Robberecht, C. et al. Cytogenetic and morphological analysis of early products of conception following hystero-embryoscopy from couples with recurrent pregnancy loss. *Prenat Diagn* 32, 933-942, doi:10.1002/pd.3936 (2012).

9 ESHRE. Recurrent Pregnancy Loss: A Guideline of the European Society of Human Reproduction and Embryology. (2017).

10 Practice Committee of the American Society for Reproductive, M. Evaluation and treatment of recurrent pregnancy loss. *Fertility and Sterility* 5, 1103-1111 (2012).

11 Cha, J., Sun, X. & Dey, S. K. Mechanisms of implantation: strategies for successful pregnancy. *Nature medicine* 18, 1754-1767, doi:10.1038/nm.3012 (2012).

12 Moraes, J. G. N. et al. Uterine influences on conceptus development in fertility-classified animals. *Proc Natl Acad Sci USA* 115, E1749-E1758, doi:10.1073/pnas.1721191115 (2018).

13 Salker, M. S. et al. Disordered IL-33/ST2 activation in decidualizing stromal cells prolongs uterine receptivity in women with recurrent pregnancy loss. *PLoS One* 7, e52252, doi:10.1371/journal.pone.0052252 (2012).

14 Gellersen, B. & Brosens, J. J. Cyclic decidualization of the human endometrium in reproductive health and failure. *Endocrine reviews* 35, 851-905, doi:10.1210/er.2014-1045 (2014).

15 Brighton, P. J. et al. Clearance of senescent decidual cells by uterine natural killer cells in cycling human endometrium. *eLife* 6, doi:10.7554/eLife.31274 (2017).

16 Nancy, P. et al. Chemokine gene silencing in decidual stromal cells limits T cell access to the maternal-fetal interface. *Science* 336, 1317-1321, doi:10.1126/science.1220030 (2012).

17 Macosko, E. Z. et al. Highly Parallel Genome-wide Expression Profiling of Individual Cells Using Nanoliter Droplets. *Cell* 161, 1202-1214, doi:10.1016/j.cell.2015.05.002 (2015).

18 Al-Sabbagh, M. et al. NADPH oxidase-derived reactive oxygen species mediate decidualization of human endometrial stromal cells in response to cyclic AMP signaling. *Endocrinology* 152, 730-740, doi:10.1210/en.2010-0899 (2011).

19 Erkenbrack, E. M. et al. The mammalian decidual cell evolved from a cellular stress response. *PLoS Biol* 16, e2005594, doi:10.1371/journal.pbio.2005594 (2018).

20 Kuroda, K. et al. Elevated periimplantation uterine natural killer cell density in human endometrium is associated with impaired corticosteroid signaling in decidualizing stromal cells. *The Journal of clinical endocrinology and metabolism* 98, 4429-4437, doi:10.1210/jc.2013-1977 (2013).

21 Song, J. J. et al. Role of glutaredoxin in metabolic oxidative stress. Glutaredoxin as a sensor of oxidative stress mediated by H2O2. *J Biol Chem* 277, 46566-46575, doi:10.1074/jbc.M206826200 (2002).

22 Zuo, R. J. et al. Crystallin alphaB acts as a molecular guard in mouse decidualization: regulation and function during early pregnancy. *FEBS Lett* 588, 2944-2951, doi:10.1016/j.febslet.2014.05.045 (2014).

23 Latini, F. R. et al. ABI3 ectopic expression reduces in vitro and in vivo cell growth properties while inducing senescence. *BMC Cancer* 11, 11, doi:10.1186/1471-2407-11-11 (2011).

24 Michishita, E., Garces, G., Barrett, J. C. & Horikawa, I. Upregulation of the KIAA1199 gene is associated with cellular mortality. *Cancer Lett* 239, 71-77, doi:10.1016/j.canlet.2005.07.028 (2006).

25 Petropoulou, C., Trougakos, I. P., Kolettas, E., Toussaint, O. & Gonos, E. S. Clusterin/apolipoprotein J is a novel biomarker of cellular senescence that does not affect the proliferative capacity of human diploid fibroblasts. *FEBS Lett* 509, 287-297 (2001).

26 Trougakos, I. P. The molecular chaperone apolipoprotein J/clusterin as a sensor of oxidative stress: implications in therapeutic approaches—a mini-review. *Gerontology* 59, 514-523, doi:10.1159/000351207 (2013).

27 Bianco, A. C. & Kim, B. W. Deiodinases: implications of the local control of thyroid hormone action. *J Clin Invest* 116, 2571-2579, doi:10.1172/JCI29812 (2006).

28 Altmae, S. et al. Meta-signature of human endometrial receptivity: a meta-analysis and validation study of transcriptomic biomarkers. *Sci Rep* 7, 10077, doi:10.1038/s41598-017-10098-3 (2017).

29 Vento-Tormo, R. et al. Single-cell reconstruction of the early maternal-fetal interface in humans. *Nature* 563, 347-353, doi:10.1038/s41586-018-0698-6 (2018).

30 Drury, J. A., Tang, A. W., Turner, M. A. & Quenby, S. A rapid, reliable method for uNK cell density estimation. *J Reprod Immunol* 97, 183-185, doi:10.1016/j.jri.2012.12.002 (2013).

31 Lucas, E. S. et al. Loss of Endometrial Plasticity in Recurrent Pregnancy Loss. *Stem Cells* 34, 346-356, doi:10.1002/stem.2222 (2016).

32 Ramsey, E. M., Houston, M. L. & Harris, J. W. Interactions of the trophoblast and maternal tissues in three closely related primate species. *American journal of obstetrics and gynecology* 124, 647-652 (1976).

33 Emera, D., Romero, R. & Wagner, G. The evolution of menstruation: a new model for genetic assimilation: explaining molecular origins of maternal responses to fetal invasiveness. *Bioessays* 34, 26-35, doi:10.1002/bies.201100099 (2012).

34 Evans, J. & Salamonsen, L. A. Inflammation, leukocytes and menstruation. *Rev Endocr Metab Disord* 13, 277-288, doi:10.1007/s11154-012-9223-7 (2012).

35 Evans, J. & Salamonsen, L. A. Decidualized human endometrial stromal cells are sensors of hormone withdrawal in the menstrual inflammatory cascade. *Biol Reprod* 90, 14, doi:10.1095/biolreprod.113.108175 (2014).

36 O'Leary, M. A. et al. The placental mammal ancestor and the post-K-Pg radiation of placentals. *Science* 339, 662-667, doi:10.1126/science.1229237 (2013).

37 Marcais, A. et al. The metabolic checkpoint kinase mTOR is essential for IL-15 signaling during the development and activation of NK cells. *Nat Immunol* 15, 749-757, doi:10.1038/ni.2936 (2014).

38 Mokhtar, N. M. et al. Progestin regulates chemokine (C-X-C motif) ligand 14 transcript level in human endometrium. *Molecular human reproduction* 16, 170-177, doi:10.1093/molehr/gap100 (2010).

39 Kane, N., Kelly, R., Saunders, P. T. & Critchley, H. O. Proliferation of uterine natural killer cells is induced by human chorionic gonadotropin and mediated via the mannose receptor. *Endocrinology* 150, 2882-2888, doi:10.1210/en.2008-1309 (2009).

40 Kao, L. C. et al. Global gene profiling in human endometrium during the window of implantation. *Endocrinology* 143, 2119-2138, doi:10.1210/endo.143.6.8885 (2002).

41 Gibson, D. A., Greaves, E., Critchley, H. O. & Saunders, P. T. Estrogen-dependent regulation of human uterine natural killer cells promotes vascular remodelling via secretion of CCL2. *Hum Reprod* 30, 1290-1301, doi:10.1093/humrep/dev067 (2015).

42 Ewington, L. J., Tewary, S. & Brosens, J. J. New insights into the mechanisms underlying recurrent pregnancy loss. *J Obstet Gynaecol Res* 45, 258-265, doi:10.1111/jog.13837 (2019).

43 Santamaria, X., Mas, A., Cervello, I., Taylor, H. & Simon, C. Uterine stem cells: from basic research to advanced cell therapies. *Hum Reprod Update* 24, 673-693, doi:10.1093/humupd/dmy028 (2018).

44 Murakami, K. et al. Deficiency in clonogenic endometrial mesenchymal stem cells in obese women with reproductive failure—a pilot study. *PLoS one* 8, e82582, doi:10.1371/journal.pone.0082582 (2013).

45 Castellana, B. et al. Maternal obesity alters uterine NK activity through a functional KIR2DL1/S1 imbalance. *Immunol Cell Biol* 96, 805-819, doi:10.1111/imcb.12041 (2018).

46 Perdu, S. et al. Maternal obesity drives functional alterations in uterine NK cells. *JCI Insight* 1, e85560, doi:10.1172/jci.insight.85560 (2016).

47 Boots, C. E., Bernardi, L. A. & Stephenson, M. D. Frequency of euploid miscarriage is increased in obese women with recurrent early pregnancy loss. *Fertil Steril* 102, 455-459, doi:10.1016/j.fertnstert.2014.05.005 (2014).

48 Leitao, B. et al. Silencing of the JNK pathway maintains progesterone receptor activity in decidualizing human endometrial stromal cells exposed to oxidative stress signals. *FASEB journal: official publication of the Federation of American Societies for Experimental Biology* 24, 1541-1551 (2010).

49 Leitao, B. B., Jones, M. C. & Brosens, J. J. The SUMO E3-ligase PIAS1 couples reactive oxygen species-dependent JNK activation to oxidative cell death. *FASEB J* 25, 3416-3425, doi:10.1096/fj.11-186346 (2011).

50 Salker, M. S. et al. Deregulation of the serum- and glucocorticoid-inducible kinase SGK1 in the endometrium causes reproductive failure. *Nature medicine* 17, 1509-1513, doi:10.1038/nm.2498 (2011).

51 Kajihara, T. et al. Differential expression of FOXO1 and FOXO3a confers resistance to oxidative cell death upon endometrial decidualization. *Mol Endocrinol* 20, 2444-2455, doi:10.1210/me.2006-0118 (2006).

52 Muter, J. et al. Progesterone-Dependent Induction of Phospholipase C-Related Catalytically Inactive Protein 1 (PRIP-1) in Decidualizing Human Endometrial Stromal Cells. *Endocrinology* 157, 2883-2893, doi:10.1210/en.2015-1914 (2016).

53 Kuroda, K. et al. Elevated periimplantation uterine natural killer cell density in human endometrium is associated with impaired corticosteroid signaling in decidualizing stromal cells. *The Journal of clinical endocrinology and metabolism* 98, 4429-4437, doi:10.1210/jc.2013-1977 (2013).

54 Weyemi, U. et al. ROS-generating NADPH oxidase NOX4 is a critical mediator in oncogenic H-Ras-induced DNA damage and subsequent senescence. *Oncogene* 31, 1117-1129, 10 doi:10.1038/onc.2011.327 (2012).

55 Colombo, A. R., Elias, H. K. & Ramsingh, G. Senescence induction universally activates transposable element expression. *Cell Cycle,* 1-12, doi:10.1080/15384101.2018.1502576 (2018).

56 van Deursen, J. M. The role of senescent cells in ageing. *Nature* 509, 439-446, doi:10.1038/nature13193 (2014).

57 Uhlen, M. et al. Proteomics. Tissue-based map of the human proteome. *Science* 347, 1260419, doi:10.1126/science.1260419 (2015).

58 van Deursen J M. Senolytic therapies for healthy longevity. *Science,* 364, 6441:636-7 (2019).

59 Zhong J, Rajagopalan S. Dipeptidyl Peptidase-4 Regulation of SDF-1/CXCR4 Axis: Implications for Cardiovascular Disease. Front Immunol. 2015; 6:477.

60 Imai K, Maeda M, Fujiwara H, Kariya M, Takakura K, Kanzaki H, et al. Dipeptidyl peptidase IV as a differentiation marker of the human endometrial glandular cells. Hum Reprod. 1992; 7(9):1189-94.

61 Suhorutshenko M, Kukushkina V, Velthut-Meikas A, Altmae S, Peters M, Magi R, et al. Endometrial receptivity revisited: endometrial transcriptome adjusted for tissue cellular heterogeneity. Hum Reprod. 2018; 33(11):2074-86.

62 Wang X, Mamillapalli R, Mutlu L, Du H, Taylor H S. Chemoattraction of bone marrow-derived stem cells towards human endometrial stromal cells is mediated by estradiol regulated CXCL12 and CXCR4 expression. Stem Cell Res. 2015; 15(1):14-22.

63 Yi K W, Mamillapalli R, Sahin C, Song J, Tal R, Taylor H S. Bone marrow-derived cells or C-X-C motif chemokine 12 (CXCL12) treatment improve thin endometrium in a mouse model. Biol Reprod. 2018.

64 Deacon C F. A review of dipeptidyl peptidase-4 inhibitors. Hot topics from randomized controlled trials. Diabetes Obes Metab. 2018; 20 Suppl 1:34-46.

65 Barros F S, Brosens, J. J., Brighton, P. J. Isolation and Primary Culture of Various Cell Types from Whole Human Endometrial Biopsies. Bio-protocol. 2016; 6:e2028.

66 Masuda H, Anwar S S, Buhring H J, Rao J R, Gargett C E. A novel marker of human endometrial mesenchymal stem-like cells. Cell Transplant. 2012; 21(10):2201-14.

67 Lucas E S, Dyer N P, Murakami K, Lee Y H, Chan Y W, Grimaldi G, et al. Loss of Endometrial Plasticity in Recurrent Pregnancy Loss. Stem Cells. 2016; 34(2):346-56.

68 Pfaffl M W. A new mathematical model for relative quantification in real-time RT-PCR. Nucleic Acids Res. 2001; 29(9):e45.

69 Turco M Y, Gardner L, Hughes J, Cindrova-Davies T, Gomez M J, Farrell L, et al. Long-term, hormone-responsive organoid cultures of human endometrium in a chemically defined medium. Nat Cell Biol. 2017.

70 Lash G E, Bulmer J N, Li T C, Innes B A, Mariee N, Patel G, et al. Standardisation of uterine natural killer (uNK) cell measurements in the endometrium of women with recurrent reproductive failure. J Reprod Immunol. 2016; 116:50-9.

71 Murakami K, Bhandari H, Lucas E S, Takeda S, Gargett C E, Quenby S, et al. Deficiency in clonogenic endometrial mesenchymal stem cells in obese women with reproductive failure—a pilot study. PLoS One. 2013; 8(12):e82582.

72 Wang W, Choi B K, Li W, Lao Z, Lee A Y, Souza S C, et al. Quantification of intact and truncated stromal cell-derived factor-Ialpha in circulation by immunoaffinity enrichment and tandem mass spectrometry. J Am Soc Mass Spectrom. 2014; 25(4):614-25.

73 Du H, Taylor H S. Contribution of bone marrow-derived stem cells to endometrium and endometriosis. Stem Cells. 2007; 25(8):2082-6.

74 Morelli S S, Rameshwar P, Goldsmith L T. Experimental evidence for bone marrow as a source of nonhematopoietic endometrial stromal and epithelial compartment cells in a murine model. Biol Reprod. 2013; 89(1):7.

75 Taylor H S. Endometrial cells derived from donor stem cells in bone marrow transplant recipients. JAMA. 2004; 292(1):81-5.

76 Schachinger V, Erbs S, Elsasser A, Haberbosch W, Hambrecht R, Holschermann H, et al. Intracoronary bone marrow-derived progenitor cells in acute myocardial infarction. N Engl J Med. 2006; 355(12):1210-21.

77 Brenner C, Adrion C, Grabmaier U, Theisen D, von Ziegler F, Leber A, et al. Sitagliptin plus granulocyte colony-stimulating factor in patients suffering from acute myocardial infarction: A double-blind, randomized placebo-controlled trial of efficacy and safety (SITAGRAMI trial). Int J Cardiol. 2016; 205:23-30.

78 Santamaria X, Cabanillas S, Cervello I, Arbona C, Raga F, Ferro J, et al. Autologous cell therapy with CD133+ bone marrow-derived stem cells for refractory Asherman's syndrome and endometrial atrophy: a pilot cohort study. Hum Reprod. 2016; 31(5):1087-96.

79 Alba M, Sheng D, Guan Y, Williams-Herman D, Larson P, Sachs J R, et al. Sitagliptin 100 mg daily effect on DPP-4 inhibition and compound-specific glycemic improvement. Curr Med Res Opin. 2009; 25(10):2507-14.

80 Farag S S, Nelson R, Cairo M S, O'Leary H A, Zhang S, Huntley C, et al. High-dose sitagliptin for systemic inhibition of dipeptidylpeptidase-4 to enhance engraftment of single cord umbilical cord blood transplantation. Oncotarget. 2017; 8(66):110350-7.

The invention claimed is:

1. A method of treating a reproductive disorder in a female individual, the method comprising administering an agent to, and/or carrying out a treatment regimen on, the individual who is positively diagnosed or assessed as being at risk of a reproductive disorder, to treat the reproductive disorder;

wherein the individual is positively diagnosed or assessed as being at risk of a reproductive disorder, by having an increased level of DIO2, and/or by having a decreased level of SCARA5 as compared with a reference sample or level which represents the sample or the level from an individual or multiple individuals known to not have any reproductive disorder;

wherein the agent is a dipeptidyl-peptidase IV (DPP4) inhibitor;

wherein the treatment regimen comprises endometrial scratching; and wherein administration of the agent to or carrying out the treatment regimen on the individual is prior to pregnancy.

2. The method according to claim 1, wherein the treatment regimen is endometrial scratching and/or the agent is a DPP4 inhibitor which is selected from sitagliptin, vildagliptin, saxagliptin, linagliptin, gemigliptin, anagliptin, teneligliptin, alogliptin, trelagliptin, omarigliptin, evogliptin, gosogliptin, or dutogliptin.

3. The method according to claim 2, wherein the DPP4 inhibitor is sitagliptin.

4. The method according to claim 1, wherein DPP4 inhibitor is administered to the individual in a daily dose from about 50 mg/day to about 2000 mg/day.

5. The method according to claim 1, wherein the individual is positively diagnosed or assessed as being at risk of a reproductive disorder by having both: (i) said increased level of DIO2, and/or said decreased level of SCARA5 as compared with a reference sample or level which represents the sample or the level from an individual or multiple individuals known to not have any reproductive disorder; and (ii) a decreased level of UNK cells or uNK cell gene markers as compared with a reference sample or level.

6. The method according to claim 1, wherein the agent or treatment regimen increases a level of decidual cells and/or uNK cells, and/or decreases a level of decidual senescent cells in the individual.

7. The method according to claim 1, wherein administration of the agent to or the carrying out of the treatment regimen on the individual is prior to menstruation.

8. The method according to claim 1, wherein the method further comprises administering progesterone and/or progestogen.

9. The method according to claim 1, wherein the marker genes or their respective expression products are detected and/or quantified using ELISA, Western blotting, immunohistochemistry, immunoassays, enzymatic assays or sequencing methods.

10. The method according to claim 9, wherein the sequencing methods include qPCR, Taqman-PCR, multiplex Taqman-PCR, Nanostring, targeted sequencing or digital PCR.

11. The method according to claim 1, wherein the reproductive disorder is embryo implantation failure, miscarriage, recurrent pregnancy loss, or a placental disorder.

12. A method of treating a reproductive disorder in a female individual, the method comprising diagnosing the reproductive disorder, wherein the individual is positively diagnosed or assessed as being at risk of a reproductive disorder by having an increased level of DIO2 and by having a decreased level of SCARA5 as compared with a reference sample or level which represents the sample or the level from an individual or multiple individuals known to have to not have any reproductive disorder;

administering an agent and/or carrying out a treatment regimen effective to the individual who is positively diagnosed or assessed as being at risk of a reproductive disorder, to treat the reproductive disorder;

wherein the agent is a dipeptidyl-peptidase IV (DPP4) inhibitor;

wherein the treatment regimen involves endometrial scratching; and wherein administration of the agent to or carrying out the treatment regimen on the individual is prior to pregnancy.

*    *    *    *    *